United States Patent
Pyo et al.

(10) Patent No.: US 10,790,450 B2
(45) Date of Patent: Sep. 29, 2020

(54) ORGANIC LIGHT-EMITTING DIODE WITH HIGH EFFICIENCY AND LONG LIFETIME

(71) Applicant: SFC CO., LTD., Cheongju (KR)

(72) Inventors: Sung-Wan Pyo, Daejeon (KR); So Young Shim, Daejeon (KR); Se Jin Yu, Gyeongsan (KR)

(73) Assignee: SFC CO., LTD., Cheongju (KR)

( * ) Notice: Subject to any disclaimer, the term of this patent is extended or adjusted under 35 U.S.C. 154(b) by 0 days.

(21) Appl. No.: 15/201,995

(22) Filed: Jul. 5, 2016

(65) Prior Publication Data
US 2017/0012214 A1   Jan. 12, 2017

(30) Foreign Application Priority Data

Jul. 9, 2015   (KR) .................. 10-2015-0097992

(51) Int. Cl.
| | | |
|---|---|---|
| H01L 51/00 | (2006.01) | |
| C09K 11/02 | (2006.01) | |
| C07D 495/10 | (2006.01) | |
| C07D 493/10 | (2006.01) | |

(Continued)

(52) U.S. Cl.
CPC ........ *H01L 51/0061* (2013.01); *C07D 493/04* (2013.01); *C07D 493/10* (2013.01); *C07D 495/10* (2013.01); *C09K 11/025* (2013.01); *C09K 11/06* (2013.01); *H01L 51/006* (2013.01); *H01L 51/0052* (2013.01); *H01L 51/0054* (2013.01); *H01L 51/0058* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/0094* (2013.01); *C09K 2211/1007* (2013.01);

(Continued)

(58) Field of Classification Search
None
See application file for complete search history.

(56) References Cited

U.S. PATENT DOCUMENTS

| | | | | |
|---|---|---|---|---|
| 2015/0034919 A1* | 2/2015 | Kim | ............... | H01L 51/0058 257/40 |
| 2016/0190466 A1* | 6/2016 | Pfister | ............. | H01L 51/0056 252/500 |

(Continued)

FOREIGN PATENT DOCUMENTS

| | | | |
|---|---|---|---|
| CN | 104629721 A | * | 5/2015 |
| KR | 1020077029742 | | 2/2008 |

(Continued)

OTHER PUBLICATIONS

Office Action from China National Intellectual Property Administration, dated Dec. 18, 2018.

(Continued)

*Primary Examiner* — Jay Yang
(74) *Attorney, Agent, or Firm* — STIP Law Group, LLC

(57) ABSTRACT

Disclosed herein is an organic light-emitting diode, comprising: an organic light-emitting diode, comprising: a first electrode; a second electrode facing the first electrode; a light-emitting layer intercalated between the first electrode and the second electrode, wherein the light-emitting layer comprises at least one of the amine compounds represented by Chemical Formula A or B, and at least one of the anthracene compounds represented by Chemical Formula C.

14 Claims, 1 Drawing Sheet

(51) Int. Cl.
*C07C 15/28* (2006.01)
*C09K 11/06* (2006.01)
*C07D 493/04* (2006.01)
*H01L 51/50* (2006.01)

(52) U.S. Cl.
CPC ............... *C09K 2211/1011* (2013.01); *C09K 2211/1014* (2013.01); *C09K 2211/1029* (2013.01); *C09K 2211/1044* (2013.01); *C09K 2211/1088* (2013.01); *C09K 2211/1092* (2013.01); *C09K 2211/1096* (2013.01); *H01L 51/5012* (2013.01)

(56) References Cited

U.S. PATENT DOCUMENTS

2016/0351818 A1* 12/2016 Kim .................. C09K 11/06
2017/0207395 A1* 7/2017 Hayashi ............... C07D 307/94

FOREIGN PATENT DOCUMENTS

| | | |
|---|---|---|
| KR | 1020100109425 | 5/2012 |
| KR | 1020150043020 A | 1/2014 |
| KR | 1020140108926 A | 9/2014 |
| KR | 1020150043020 | 4/2015 |
| KR | 1020160141359 A | 12/2016 |
| KR | 1020160141360 A | 12/2016 |
| WO | WO2014010910 A1 | 1/2014 |
| WO | WO-2015/022051 A1 * | 2/2015 |
| WO | WO2015022051 A1 | 2/2015 |
| WO | WO-2016/013184 A1 * | 1/2016 |

OTHER PUBLICATIONS

Office Action from Korean Intellectual Property Office of 10-2016-0059750, dated Oct. 4, 2018.

* cited by examiner

| 80 |
|----|
| 70 |
| 60 |
| 50 |
| 40 |
| 30 |
| 20 |
| 10 |

ORGANIC LIGHT-EMITTING DIODE WITH HIGH EFFICIENCY AND LONG LIFETIME

CROSS REFERENCE TO RELATED APPLICATION

The present application claims the benefit of Korean Patent Application No. 10-2015-0097992 filed in the Korean Intellectual Property Office on Jul. 9, 2015, the entire contents of which are incorporated herein by reference.

PARTIES TO A JOINT RESEARCH AGREEMENT

The subject matter of the present invention is the result of a joint research agreement between SFC CO., LTD. and HODOGAYA CHEMICAL CO., LTD.

BACKGROUND OF THE INVENTION

1. Field of the Disclosure

The present disclosure relates to an organic light-emitting diode with high efficiency and a long lifetime. More particularly, the present disclosure relates to an organic light-emitting diode wherein host and dopant materials of specific structures are used in a light-emitting layer.

2. Description of the Related Art

Organic light emitting diodes (OLEDs), based on self-luminescence, are used to create digital displays with the advantage of being able to be thinner and lighter than liquid crystal displays (LCDs). In addition, an OLED display exhibits a much faster response time than an LCD. Accordingly, organic light emitting diodes find applications in the illumination field as well as the full-color display field.

Materials used as the organic layers in organic light emitting diodes may be divided into luminescent materials and charge carrier materials, for example, a hole injection material, a hole transport material, an electron injection material, and an electron transport material. According to the luminescent materials, there are two main families of OLED: those based on small molecules and those employing polymers. The light emitting mechanisms allows the luminescent materials to be classified as fluorescent and phosphorescent materials, which use excitons in singlet and triplet states, respectively. Further, luminescent materials may be divided into blue, green, and red light-emitting materials according to colors. Further, yellow and reddish yellow light-emitting materials were developed in order to achieve more natural colors.

Meanwhile, when a single material is employed as the luminescent material, intermolecular actions cause the maximum luminescence wavelength to shift toward a longer wavelength, resulting in a reduction in color purity and light emitting efficiency. In this regard, a host-dopant system may be used as a luminescent material so as to increase the color purity and the light emitting efficiency through energy transfer.

This is based on the principle that, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of the dopant because the wavelength of the host moves to a wavelength range of the dopant.

With regard to related arts of dopant compounds in the light-emitting layer, reference may be made to Korean Unexamined Patent Application Publication No. 10-2008-0015865 (Feb. 20, 2008), which describes an organic light emitting device using an arylamine-coupled indenofluorene derivative, and Korean Unexamined Patent Application Publication No. 10-2012-0047706 (May 14, 2012), which describes an organic photoelectric device using a compound in which dibenzofuran or dibenzothiophene coexists with fluorene or carbazole.

As a related art for using a host compound in a light-emitting layer, mention may be made of Korean Unexamined Patent Application Publication No. 10-2015-0043020 (Apr. 22, 2015), which describes an organic light-emitting diodes employing anthracene derivatives as fluorescent hosts.

However, there is still a continued need to develop organic light-emitting diodes exhibiting higher efficiency and a longer lifetime.

RELATED ART DOCUMENT

Korean Unexamined Patent Application Publication No. 10-2008-0015865 (Feb. 20, 2008)
Korean Unexamined Patent Application Publication No. 10-2012-0047706 (May 14, 2012)
Korean Unexamined Patent Application Publication No. 10-2015-0043020 (Apr. 22, 2015)

SUMMARY OF THE DISCLOSURE

Therefore, the present disclosure aims to provide a novel organic light-emitting diode (OLED) with high efficiency and a long lifetime, wherein dopant and host materials of specific structures are employed.

In accordance with an aspect thereof, the present disclosure provides an organic light-emitting diode, comprising: a first electrode; a second electrode facing the first electrode; a light-emitting layer intercalated between the first electrode and the second electrode, wherein the light-emitting layer comprises at least one of the amine compounds represented by the following Chemical Formula A or B, and at least one of the anthracene compounds represented by the following Chemical Formula C:

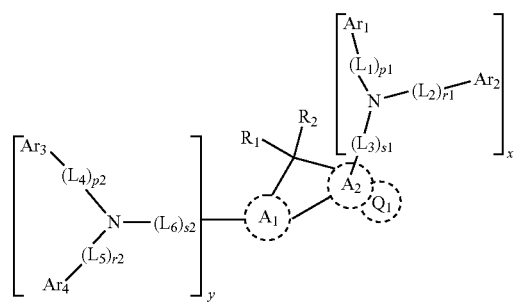

[Chemical Formula A]

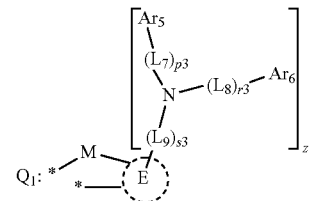

[Chemical Formula B]

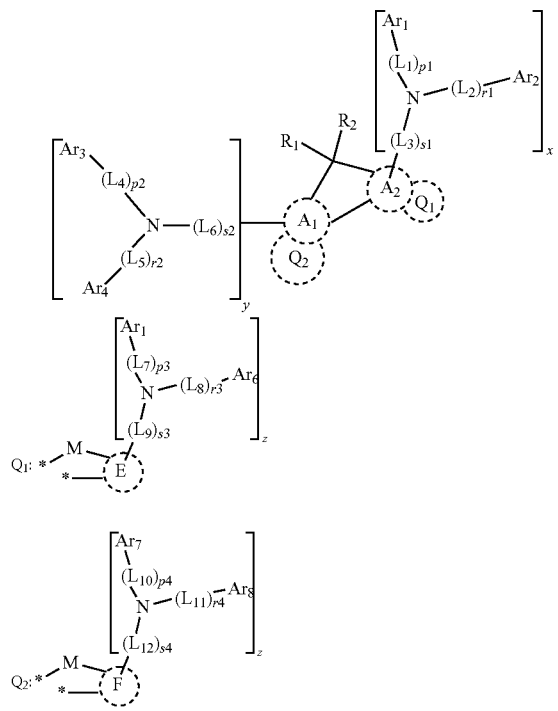

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ together may form a mono- or polycyclic aliphatic or aromatic ring that may be a heterocyclic ring containing a heteroatom selected from among N, O, P, Si, S, Ge, Se, and Te as a ring member;

p1 to p4, $R_1$ to $R_4$, and s1 to s4 are each independently an integer of 1 to 3, with the proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, two adjacent carbon atoms of the $A_1$ ring moiety of Chemical Formula B may occupy respective positions * of structural Formula $Q_2$ to form a fused ring,

[Chemical Formula C]

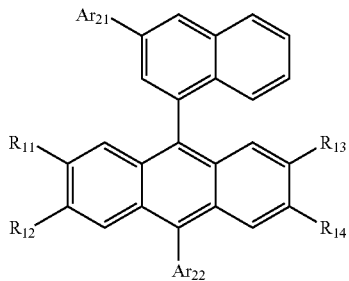

wherein, $Ar_{21}$ and $Ar_{22}$ may be the same or different and are each independently selected from among a substituted or unsubstituted aryl of 6 to 50 carbon atoms, and a substituted or unsubstituted heteroaryl of 3 to 50 carbon atoms containing O, N or S as a heteroatom, $R_{11}$ to $R_{14}$ may be the same or different and are each independently selected from the group consisting of hydrogen, deuterium, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 30 carbon atoms containing O, N or S as a heteroatom, a substituted or unsubstituted silicon, a substituted or unsubstituted boron, a substituted or unsubstituted silane, a carbonyl, a phosphoryl, an amino, a nitrile, a hydroxy, a nitro, a halogen, an amide, and an ester, with the proviso that a hydrogen atom is positioned on each of the aromatic ring carbon atoms to which none of the substituents $Ar_{21}$, $Ar_{22}$, and $R_{11}$ to $R_{14}$ are bonded, $R_{11}$ and $R_{12}$ may be bonded to each other to form a saturated or unsaturated ring, and $R_{13}$ and $R_{14}$ may being bonded to each other to form a saturated or unsaturated ring.

BRIEF DESCRIPTION OF THE DRAWINGS

The above and other objects, features and advantages of the present disclosure will be more clearly understood from the following detailed description taken in conjunction with the accompanying drawing, in which:

The FIGURE is a schematic cross-sectional view of the structure of an organic light-emitting diode according to some embodiments of the present disclosure.

DESCRIPTION OF THE PREFERRED EMBODIMENTS

Below, a detailed description will be given of the present disclosure.

In accordance with an aspect thereof, the present disclosure provides an organic light-emitting diode, comprising: a first electrode; a second electrode facing the first electrode; a light-emitting layer intercalated between the first electrode and the second electrode, wherein the light-emitting layer comprises at least one of the amine compounds represented by the following Chemical Formula A or B, and at least one of the anthracene compounds represented by the following Chemical Formula C:

[Chemical Formula A]

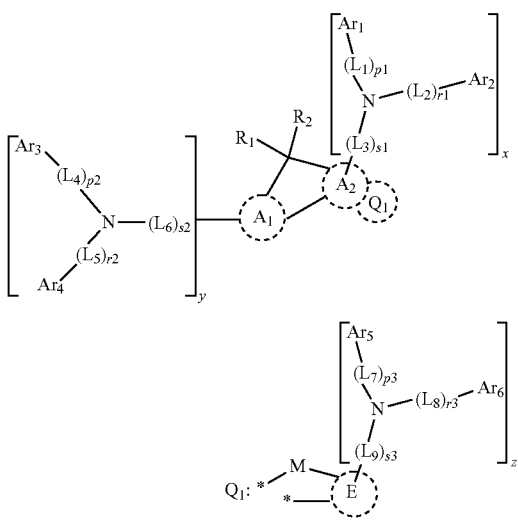

[Chemical Formula B]

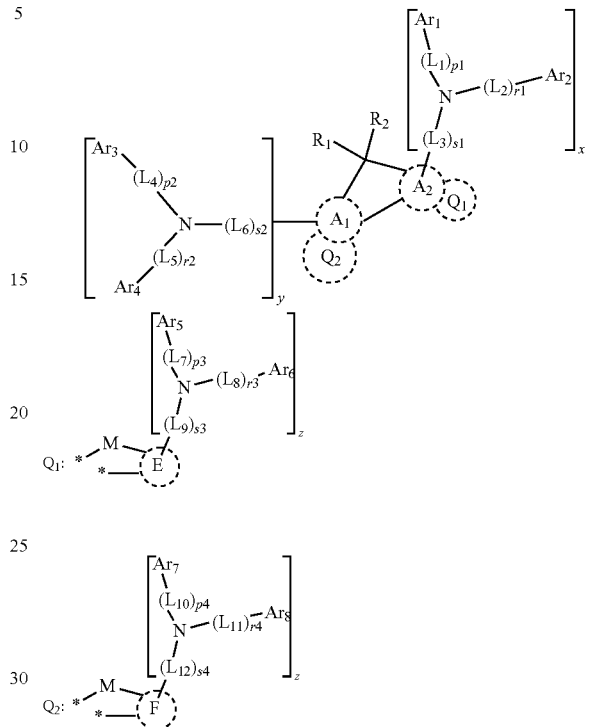

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ together may form a mono- or polycyclic aliphatic or aromatic ring that may be a heterocyclic ring containing a heteroatom selected from among N, O, P, Si, S, Ge, Se, and Te as a ring member;

p1 to p4, $R_1$ to $R_4$, and s1 to s4 are each independently an integer of 1 to 3, with the proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, two adjacent carbon atoms of the $A_1$ ring moiety of Chemical Formula B may occupy respective positions * of structural Formula $Q_2$ to form a fused ring,

[Chemical Formula C]

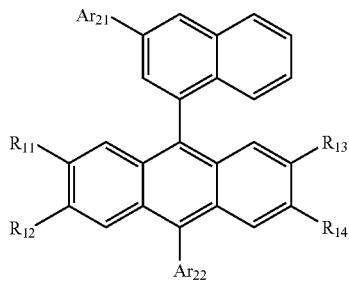

wherein, $Ar_{21}$ and $Ar_{22}$ may be the same or different and are each independently selected from among a substituted or unsubstituted aryl of 6 to 50 carbon atoms, and a substituted or unsubstituted heteroaryl of 3 to 50 carbon atoms containing O, N or S as a heteroatom, $R_{11}$ to $R_{14}$ may be the same or different and are each independently selected from the group consisting of hydrogen, deuterium, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 30 carbon atoms containing O, N or S as a heteroatom, a substituted or unsubstituted silicon, a substituted or unsubstituted boron, a substituted or unsubstituted silane, a carbonyl, a phosphoryl, an amino, a nitrile, a hydroxy, a nitro, a halogen, an amide, and an ester, with the proviso that a hydrogen atom is positioned on each of the aromatic ring carbon atoms to which none of the substituents $Ar_{21}$, $Ar_{22}$, and $R_{11}$ to $R_{14}$ are bonded, $R_{11}$ and $R_{12}$ may be bonded to each other to form a saturated or unsaturated ring, and $R_{13}$ and $R_{14}$ may being bonded to each other to form a saturated or unsaturated ring, wherein the term 'substituted' in the expression 'substituted or unsubstituted' means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

The expression for a number of carbon atoms such as in "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an organic radical, derived from an aromatic hydrocarbon by removing one hydrogen atom, including a mono- or fused ring system consisting of 5 to 7 members and preferably 5 or 6 members. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom on which may be substituted by a deuterium atom, a halogen atom, a hydroxy, a nitro, a cyano, a silyl, an amino (—$NH_2$, —NH(R), —N(R') (R'') wherein R' and R'' are each independently an alkyl of 1 to 10 alkyl, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atom of the silyl may be substituted by the same substituent as in the aryl.

The amine compound represented by Chemical Formula A or B used in the present disclosure is characterized by the structure in which the moiety of Chemical Formula $Q_1$ in Chemical Formula A is connected to the ring $A_1$ while an amine moiety containing both $Ar_1$ and $Ar_2$ is bonded to the ring $A_2$ or in which the moieties of Chemical Formulas $Q_2$ and $Q_1$ are respectively connected to the rings $A_1$ and $A_2$ while an amine moiety containing both $Ar_1$ and $Ar_2$ is bonded to the ring $A_2$.

In addition, the anthracene compound of Chemical Formula C is characterized by the structure in which an naphthyl group is bonded to the carbon atom at position 9 of an anthracenyl skeleton, and has an substituted or unsubstituted aryl of 6 to 50 carbon atoms or a substituted or unsubstituted heteroayl of 3 to 50 carbon atoms containing O, N or S as a heteroatom on the carbon atom at position 3 of the naphthyl group.

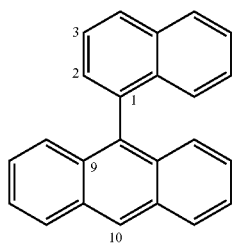 [SMILES: c1ccc2c(-c3c4ccccc4cc4ccccc34)cccc2c1]

The light-emitting layer of the organic light-emitting diode according to the present disclosure comprises a host as which and a dopant, wherein an amine compound represented by Chemical Formula A or B is used as the dopant while the compound represented by Chemical Formula C is used as the host, thus bringing about an improvement in luminance efficiency and lifetime.

In Chemical Formula C, $Ar_{21}$ and $Ar_{22}$ may be the same or different and are each independently a substituted or unsubstituted aryl of 6 to 50 carbon atoms. In this case, $Ar_{21}$ may be a substituted or unsubstituted aryl of 6 to 18 carbon atoms.

In Chemical Formulas A and B, $A_1$, $A_2$, E, and F in Chemical Formula A may be the same or different and may be each independently a substituted or unsubstituted aromatic hydrocarbon ring of 6 to 50 carbon atoms.

When $A_1$, $A_2$, E, and F in Chemical Formula A or B are each independently a substituted or unsubstituted aromatic hydrocarbon ring of 6 to 50 carbon atoms, the substituted or unsubstituted aromatic hydrocarbon ring moieties of 6 to 50 carbon atoms may be each independently any one selected from among [Structural Formula 10] to [Structural Formula 21].

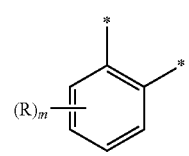
[10]

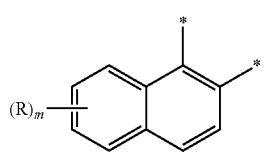
[11]

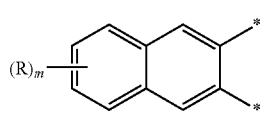
[12]

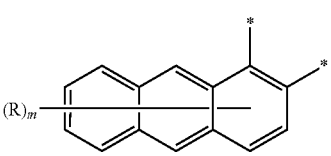
[13]

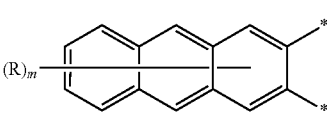
[14]

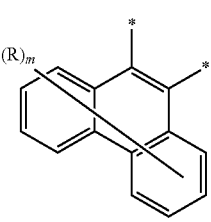
[15]

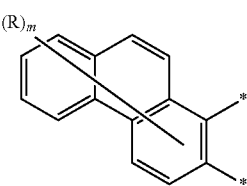
[16]

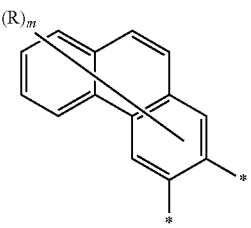
[17]

-continued

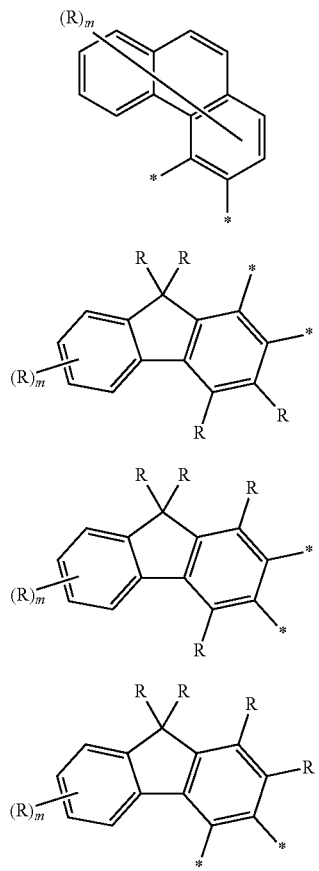

[18]

[19]

[20]

[21]

wherein,

"-*" for moiety $A_1$ or $A_2$ denotes a bonding site for forming a 5-membered ring containing the carbon atom connected to both the substituents $R_1$ and $R_2$, and "-*" for moiety E or F denotes a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R's are the same as above defined for $R_1$ and $R_2$, m is an integer of 1 to 8, with a proviso that when m is 2 or greater or R is 2 or greater, the corresponding R's may be the same or different.

In a particular embodiment, linkers $L_1$ to $L_{12}$ may be a direct bond, or any one selected from the following [Structural Formula 22] to [Structural Formula 30], p1 to p4, $R_1$ to $R_4$, and s1 to s4 may each be 1 or 2, and x may be 1:

In a particular embodiment, linkers $L_1$ to $L_{12}$ may each be a single bond, or any one selected from the following [Structural Formula 22] to [Structural Formula 30], p1 to p4, $R_1$ to $R_4$, and s1 to s4 may each be 1 or 2, and x may be 1:

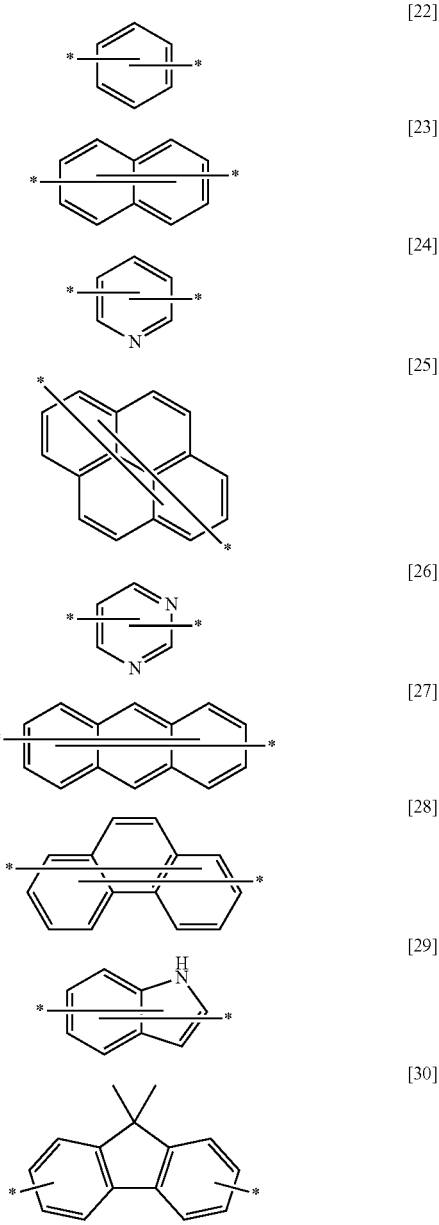

[22]

[23]

[24]

[25]

[26]

[27]

[28]

[29]

[30]

In the linker, each of the unsubstituted carbon atoms of the aromatic ring moiety is bound with a hydrogen atom or a deuterium atom.

In this case, x and y may each be 1, and z may be 0 or 1.

According to a specific embodiment of the present disclosure, $R_1$ to $R_9$, and $Ar_1$ to $Ar_8$ in the amine compound represented by Chemical Formula A or B may be the same or different and may each be independently any one selected from among hydrogen, deuterium, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms containing at least one heteroatom selected from among O, N, S, and Si, a cyano, and a halogen.

In the amine moieties of Chemical Formula A or B according to some embodiments of the present disclosure, $A_1$, $A_2$, E, F, $Ar_1$ to $Ar_8$, $L_1$ to $L_{12}$, $R_1$ to $R_9$ may have as a substituent any one selected from the group consisting of a cyano, a halogen, an alkyl of 1 to 6 carbon atoms, an aryl of 6 to 18 carbon atoms, an arylalkyl of 7 to 18 carbon atoms, a heteroaryl of 3 to 18 carbon atoms, an alkylsilyl of 1 to 12 carbon atoms, and an arylsilyl of 6 to 18 carbon atoms.

The compound represented by Chemical Formula A or B, useful in the organic light-emitting diode of the present disclosure, may be selected from compounds represented by the following [Chemical Formula 1] to [Chemical Formula 239].

<1>

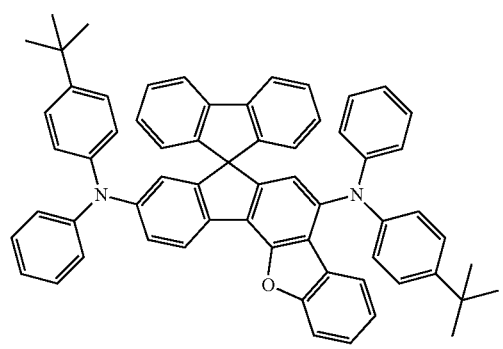

<2>

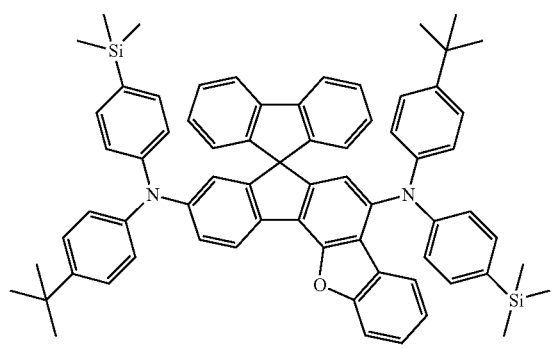

<3>

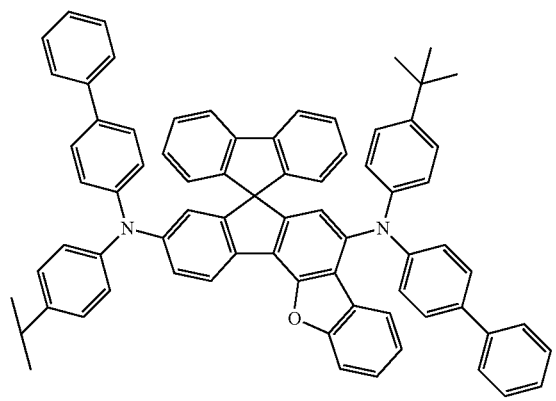

<4>

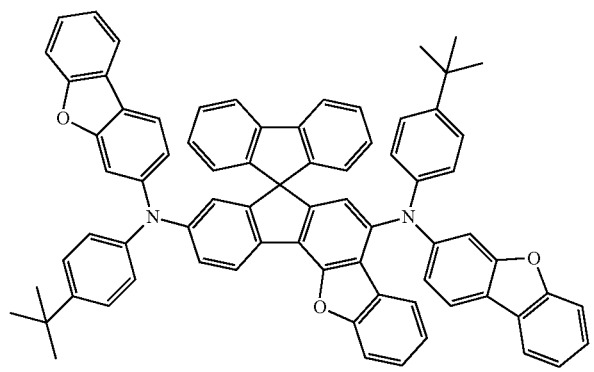

<5>

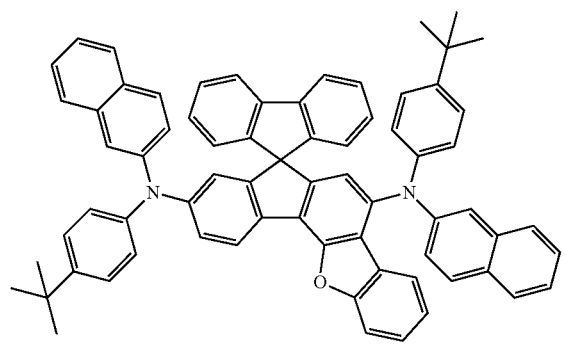

<6>

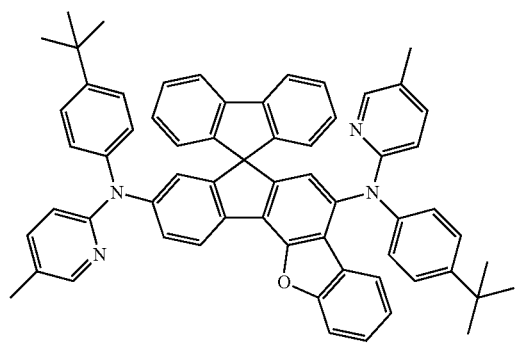

<7>

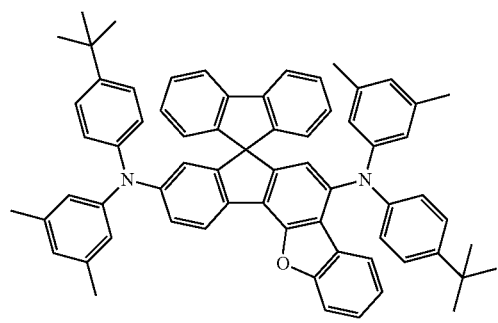

<8>

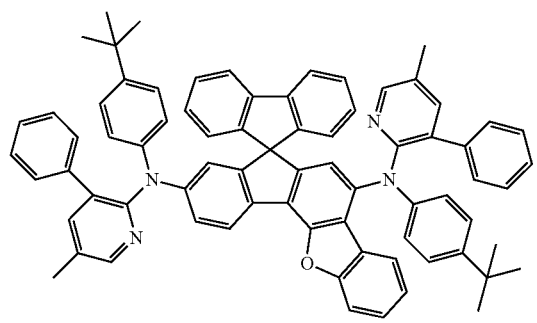

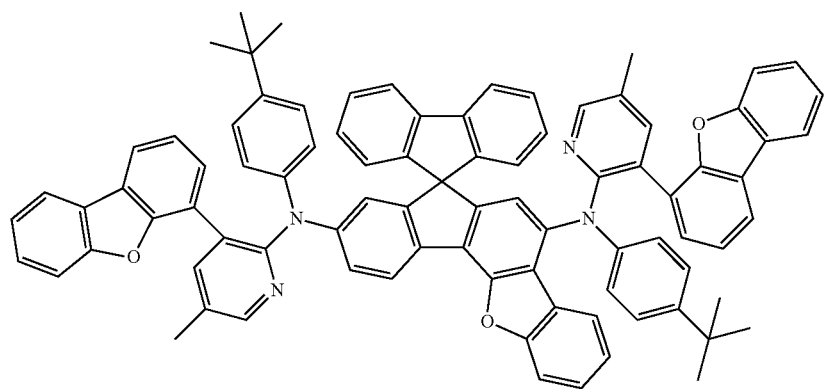
<9>
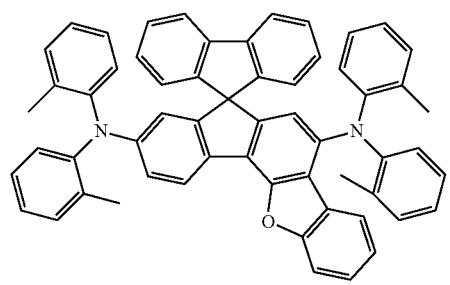
<10>
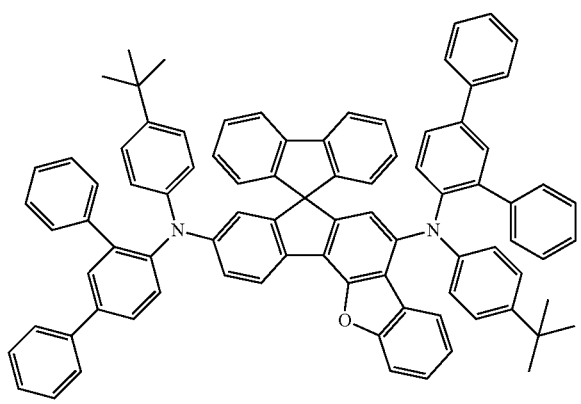
<11>
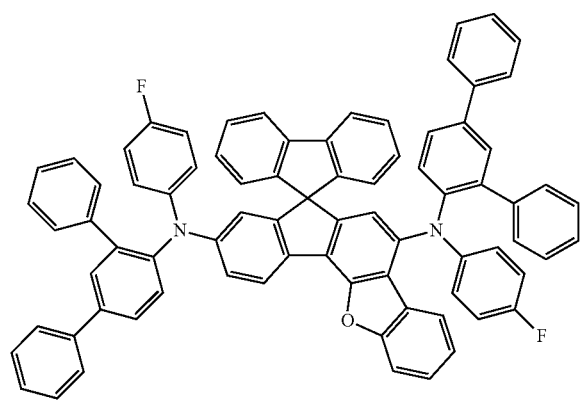
<12>
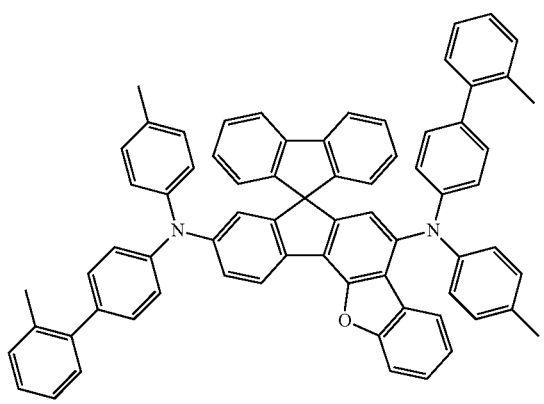
<13>

-continued
<14>
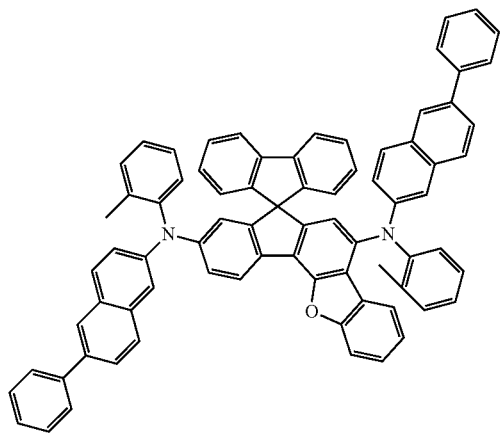
<15>
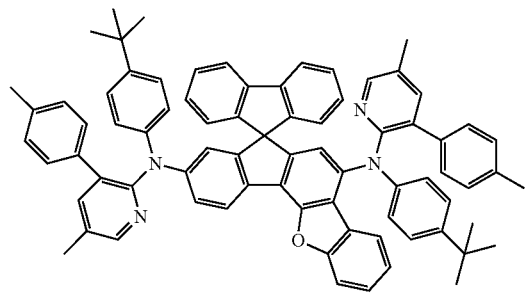
<16>
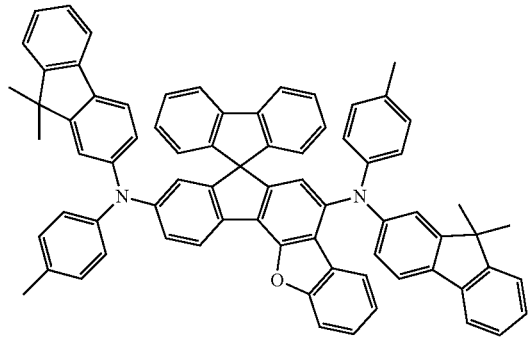
<17>
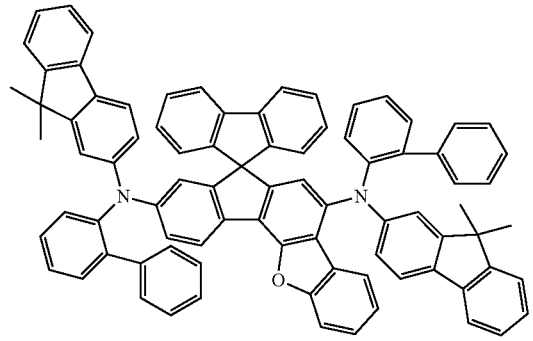
<18>
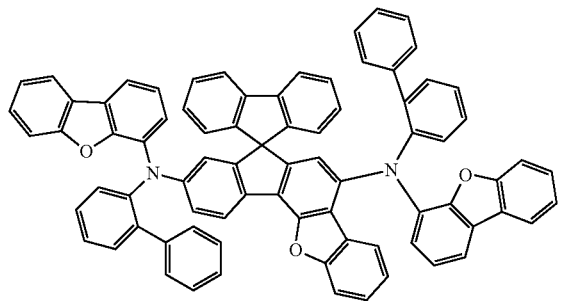
<19>
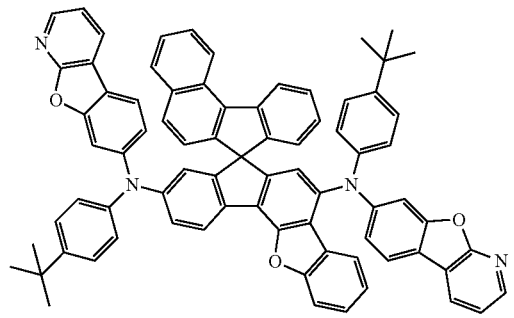
<20>
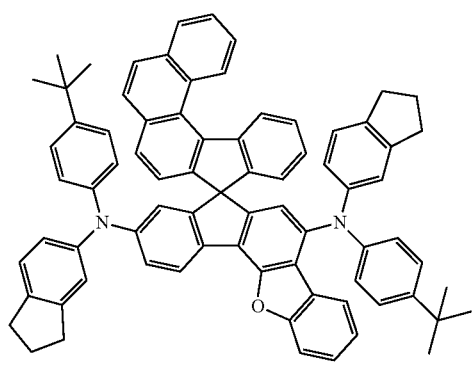
<21>
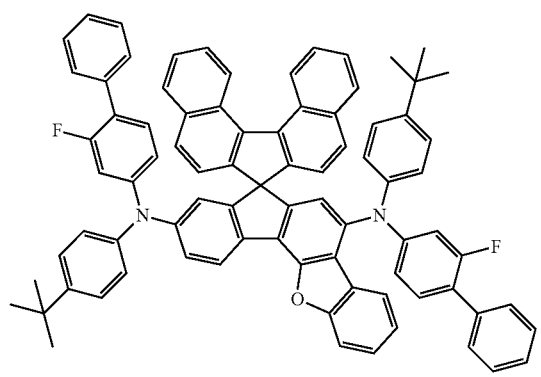

-continued
<22>
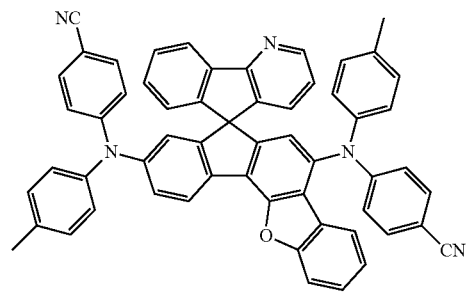
<23>
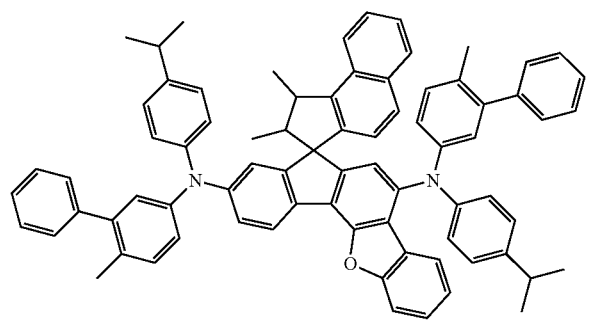
<24>
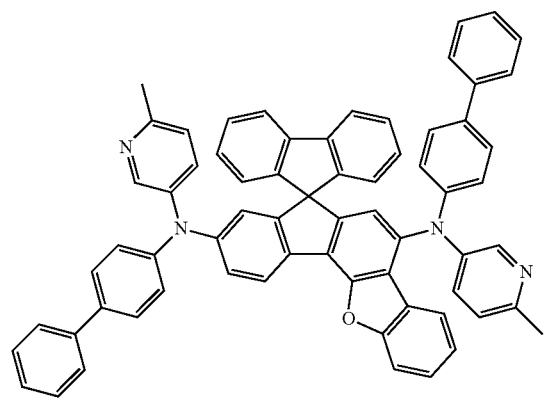
<25>
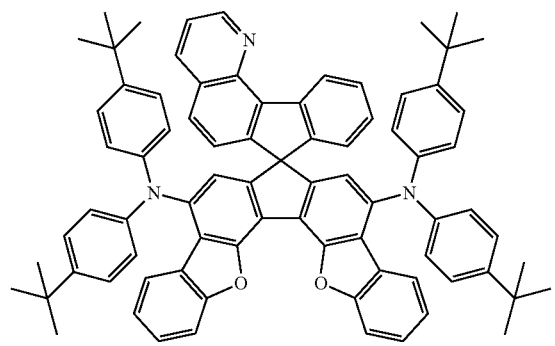
<26>
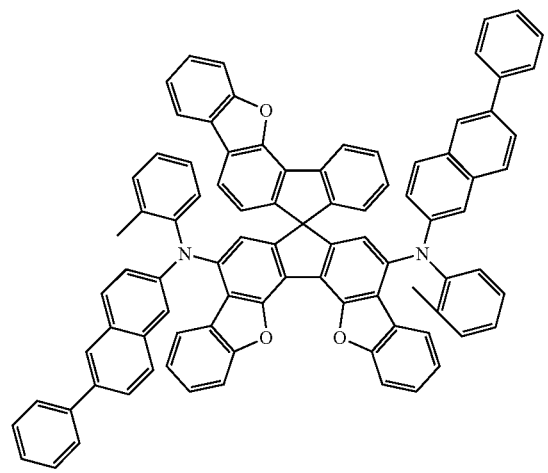
<27>
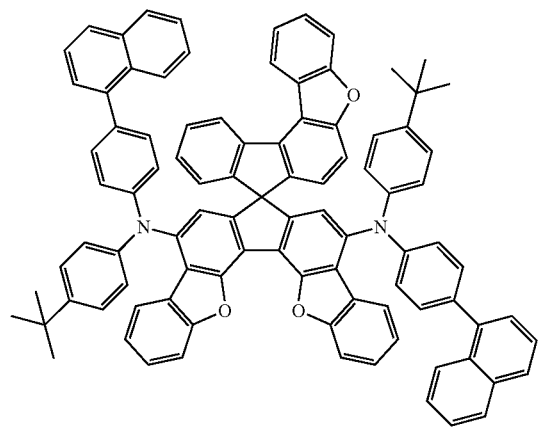
<28>
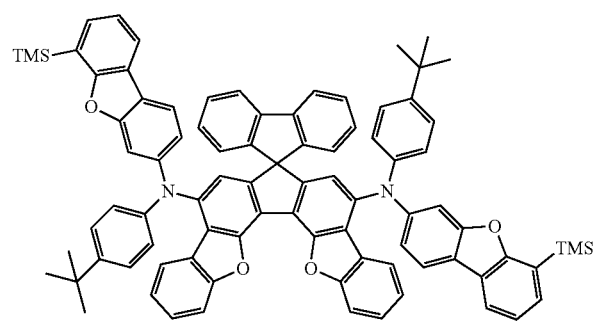
<29>
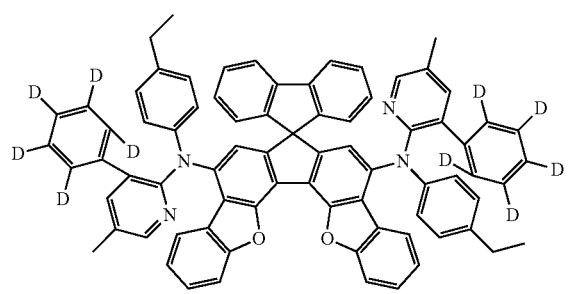

-continued
<30>
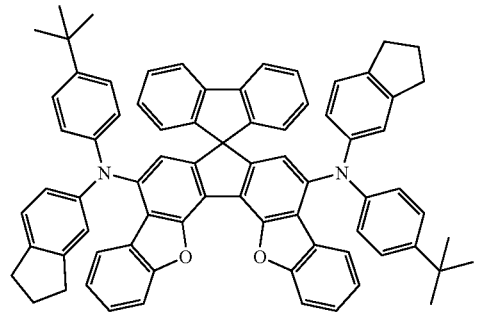
<31>
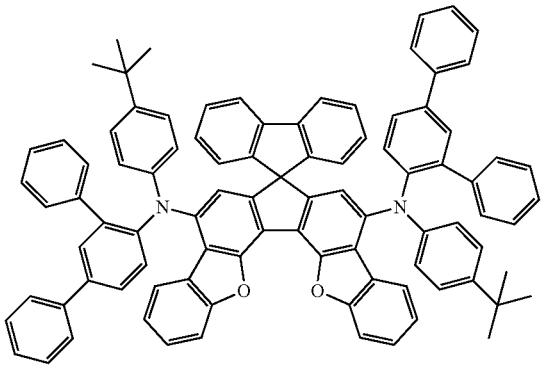
<32>
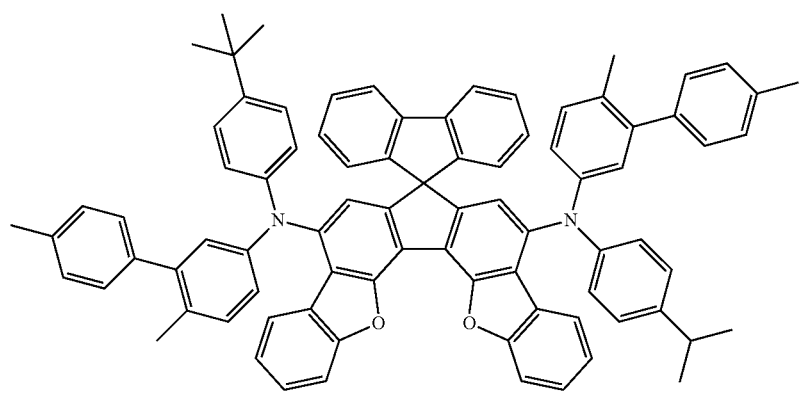
<33>
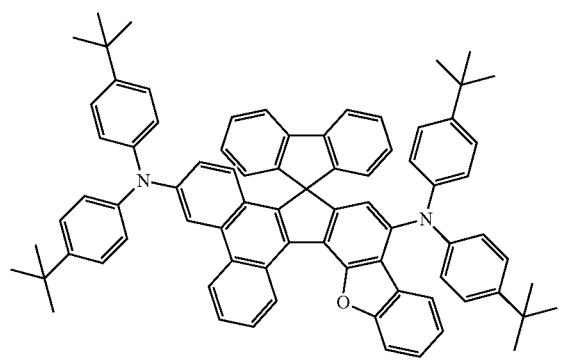
<34>
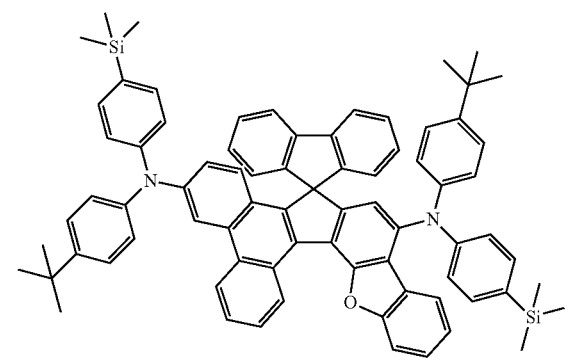
<35>
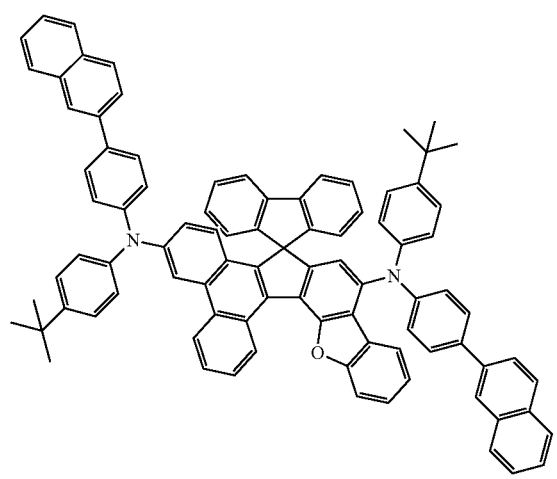
<36>
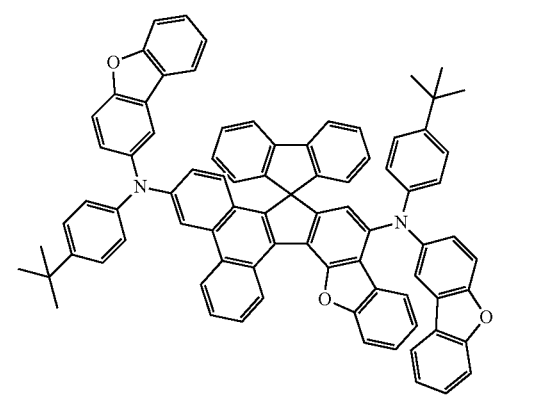

-continued
<37>
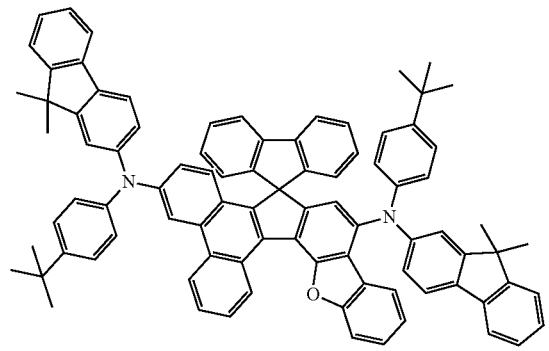
<38>
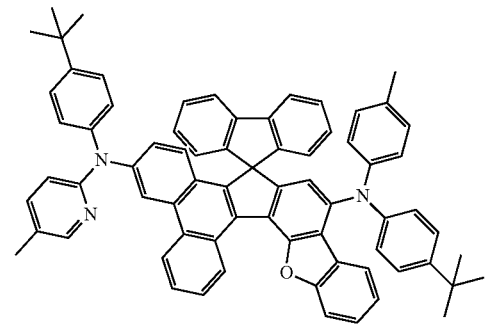
<39>
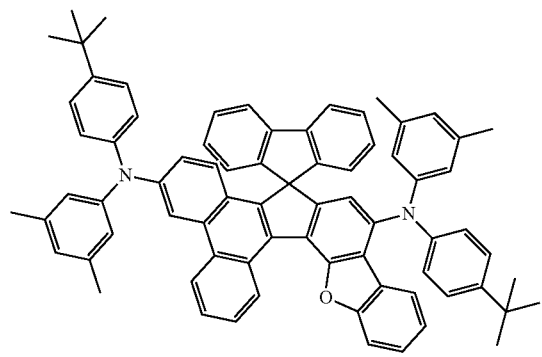
<40>
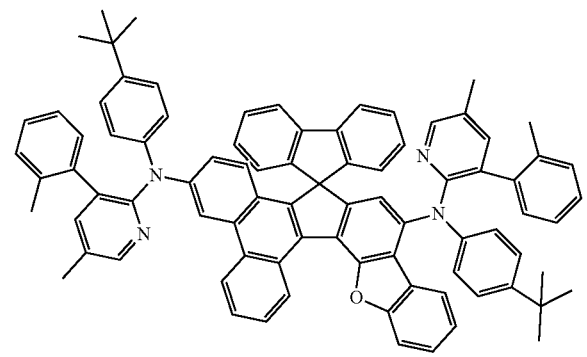
<41>
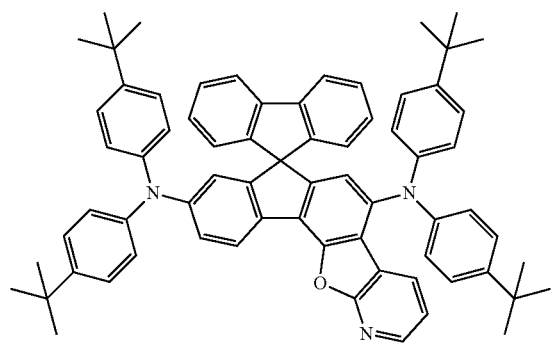
<42>
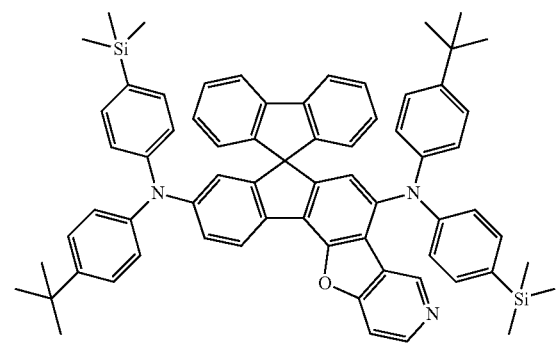
<43>
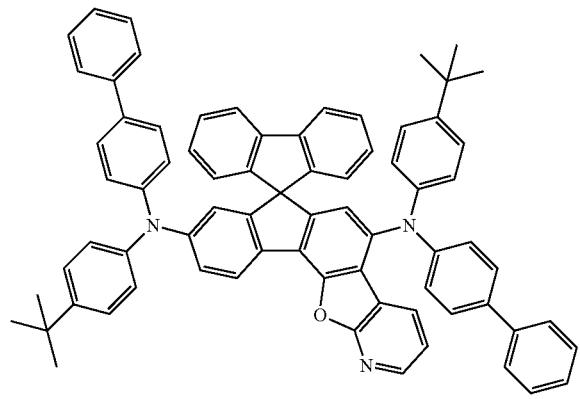
<44>
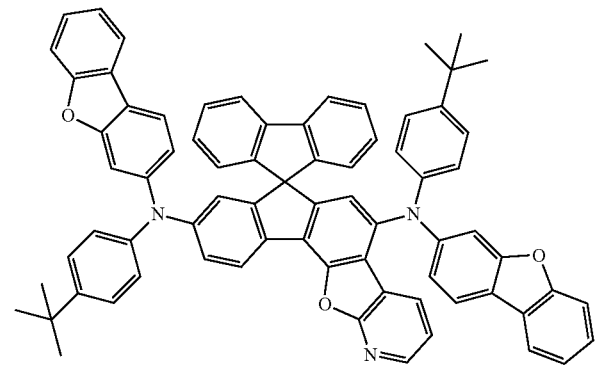

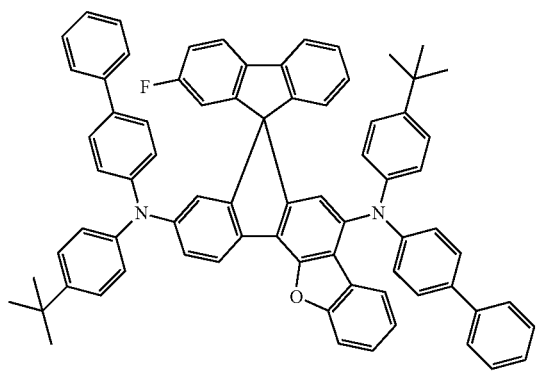
<45>
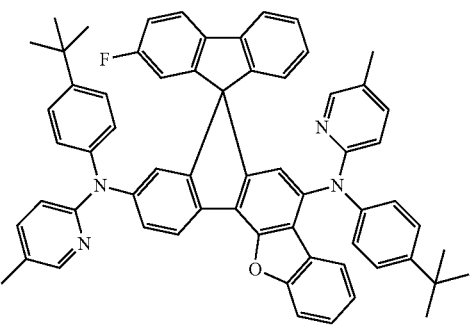
<46>
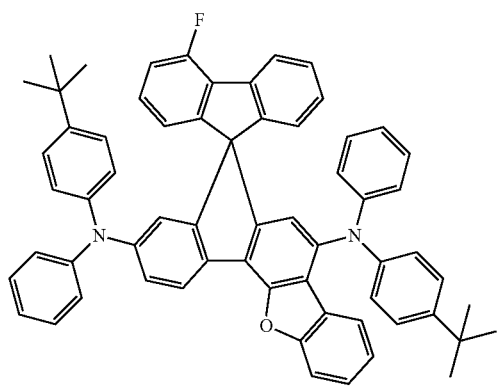
<47>
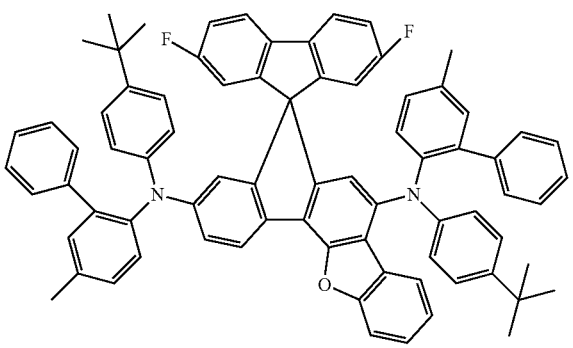
<48>
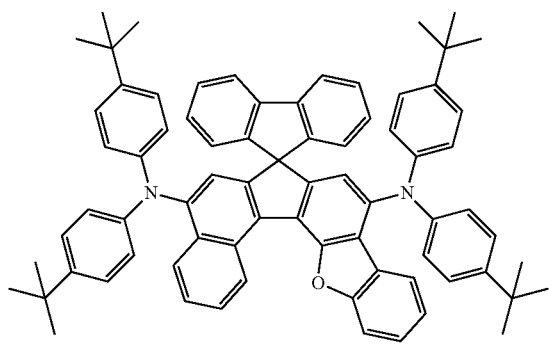
<49>
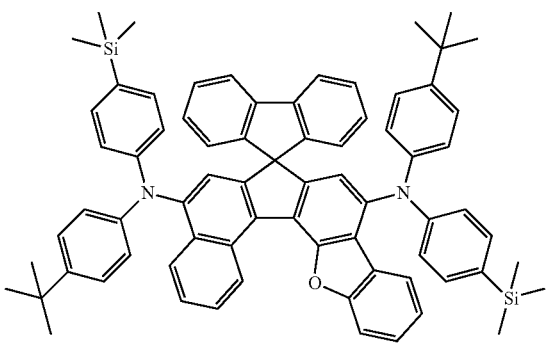
<50>
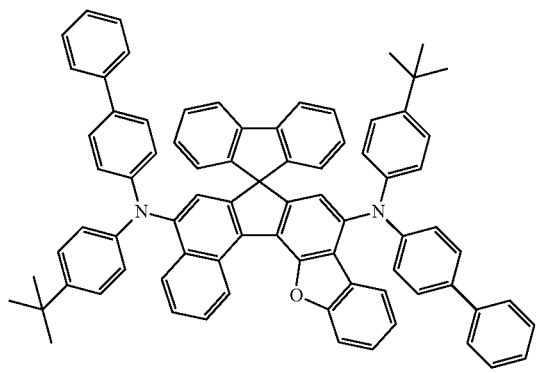
<51>
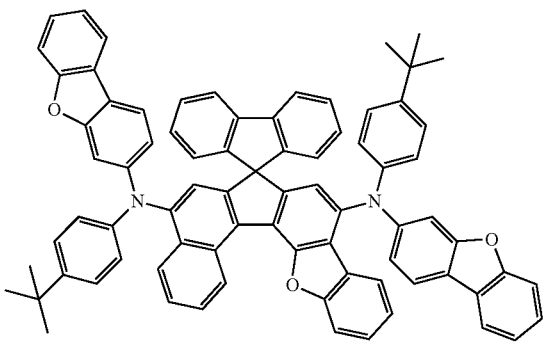
<52>

-continued
<53>
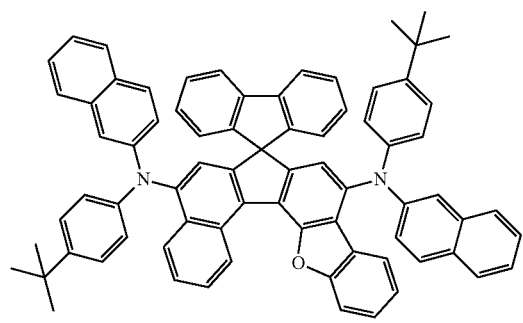
<54>
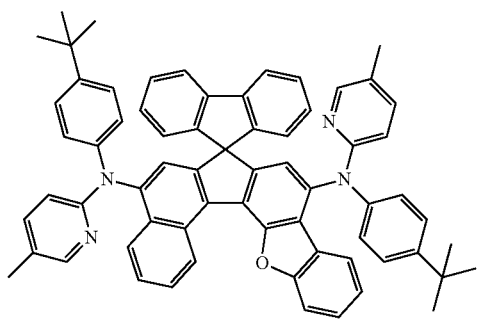
<55>
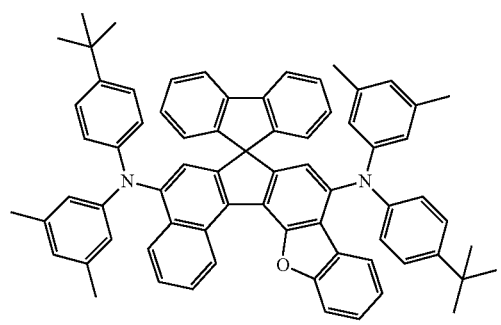
<56>
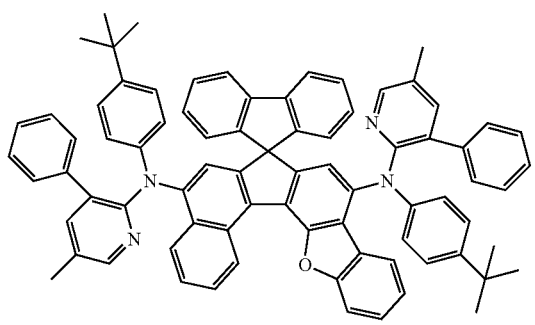
<57>
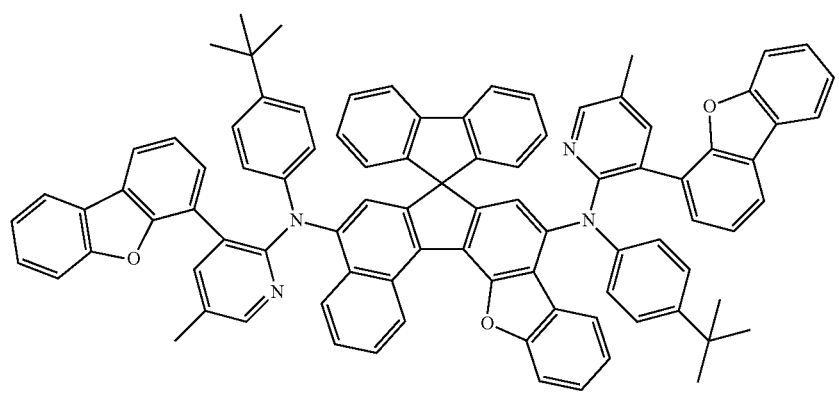
<58>
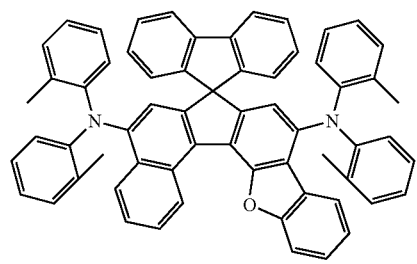
<59>
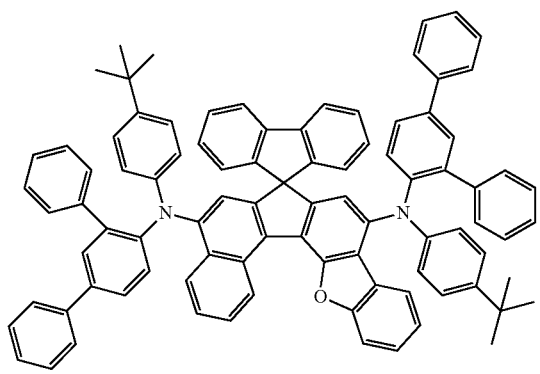

-continued
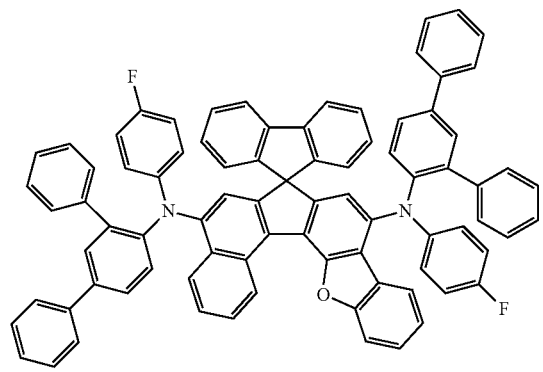
<60>
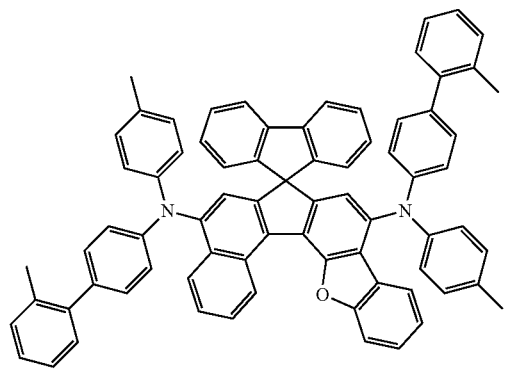
<61>
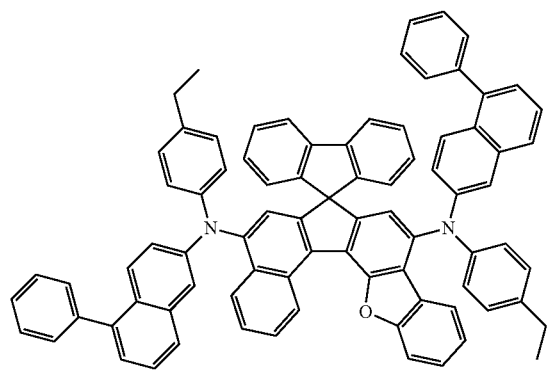
<62>
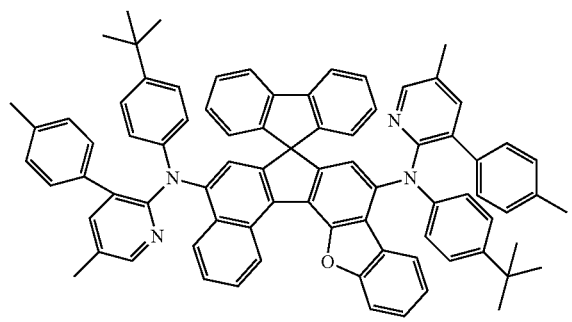
<63>
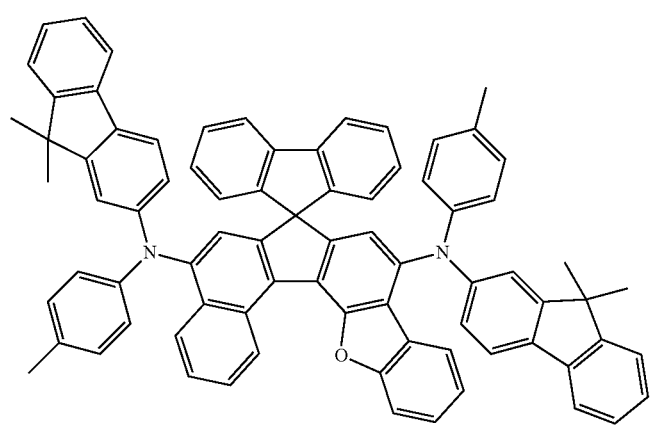
<64>

-continued
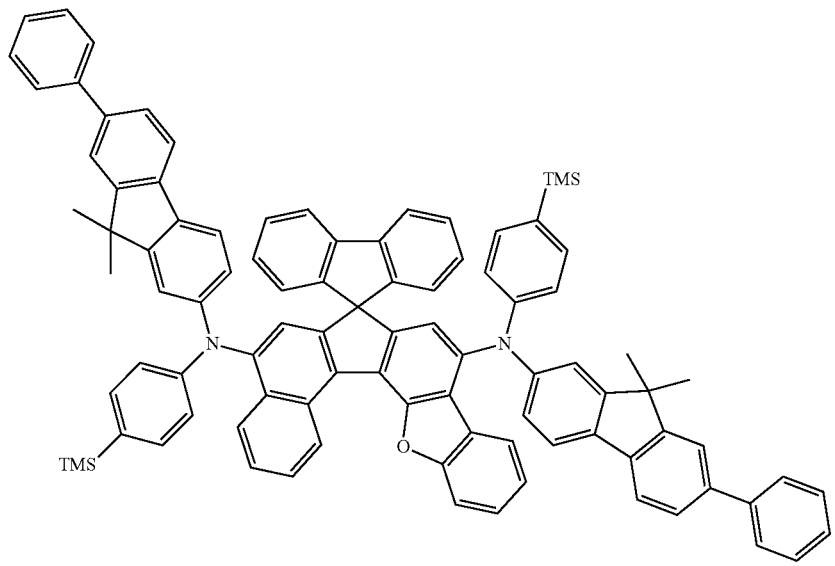
<65>
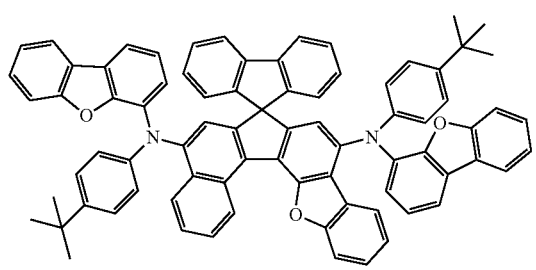
<66>
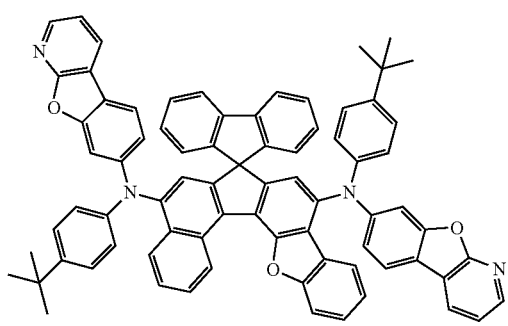
<67>
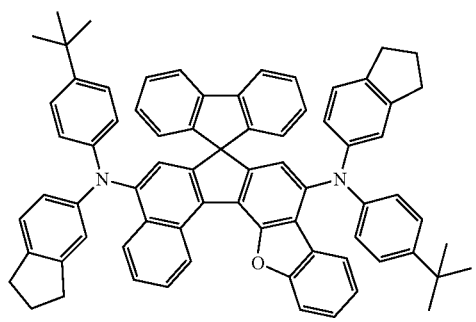
<68>
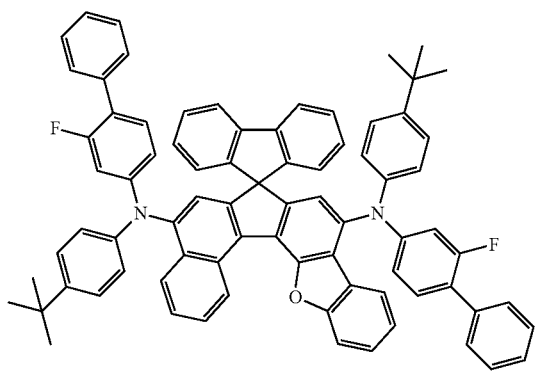
<69>
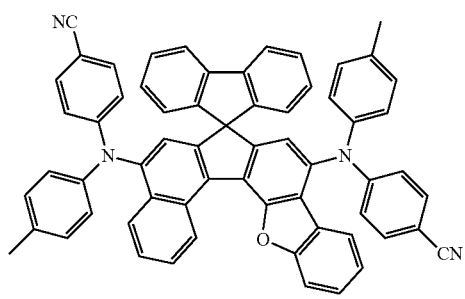
<70>
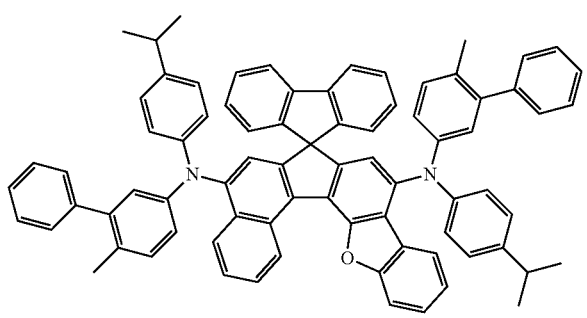
<71>

-continued
<72>
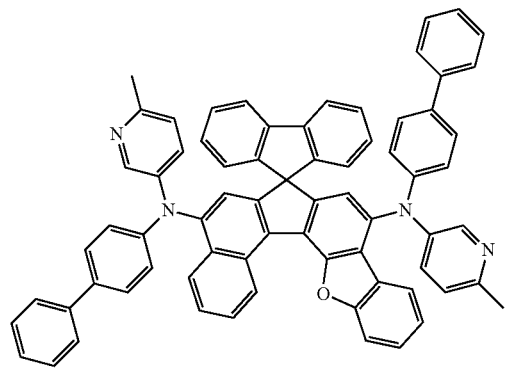
<73>
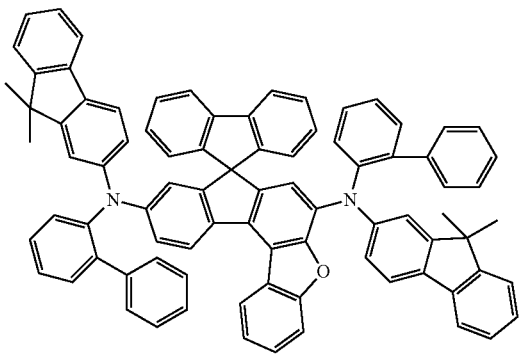
<74>
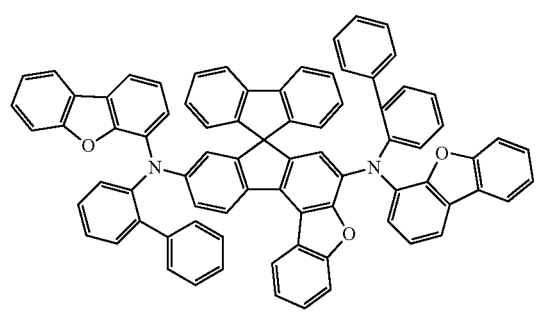
<75>
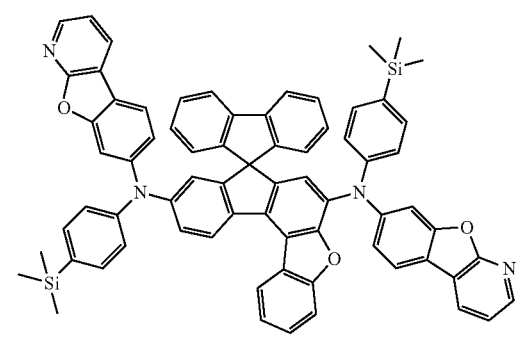
<76>
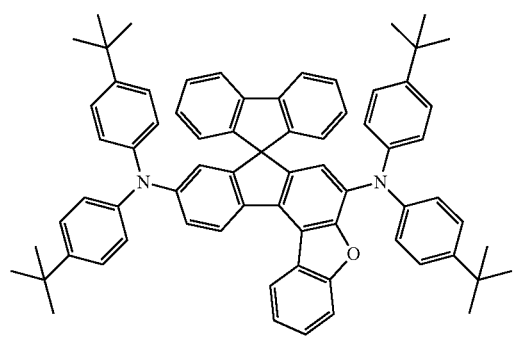
<77>
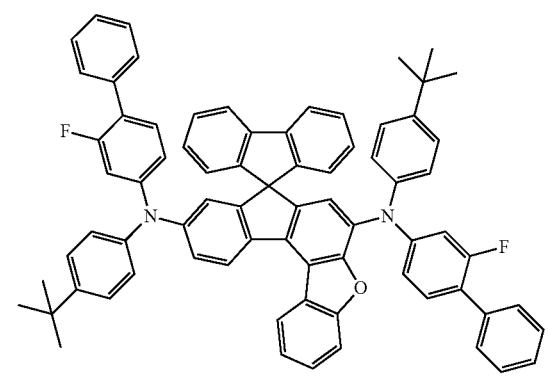
<78>
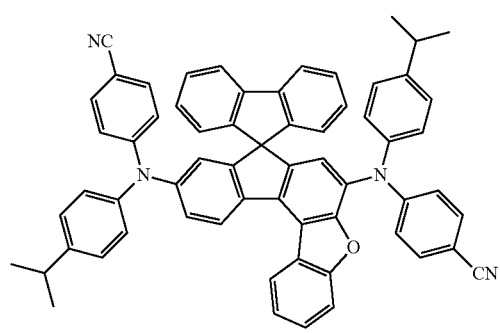
<79>
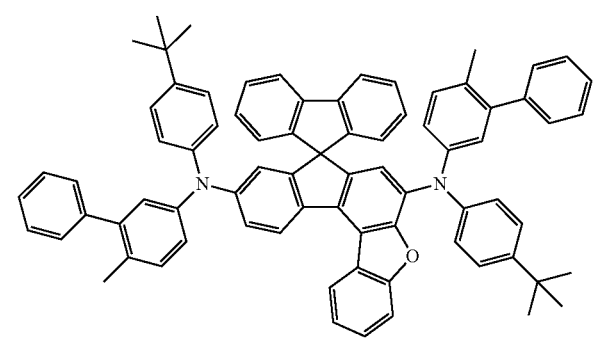

-continued
<80>
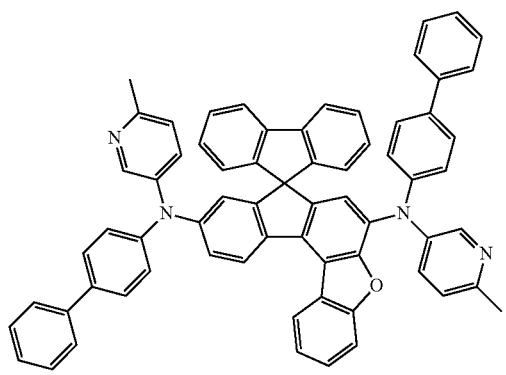
<81>
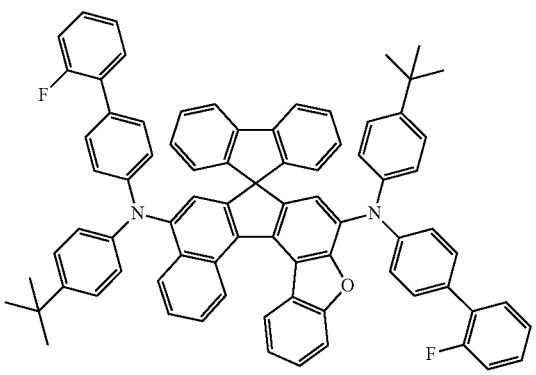
<82>
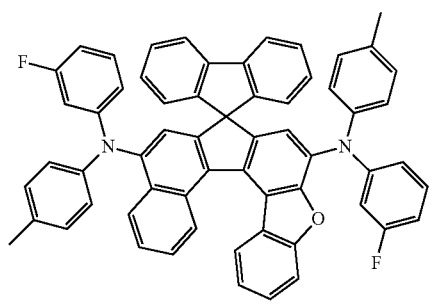
<83>
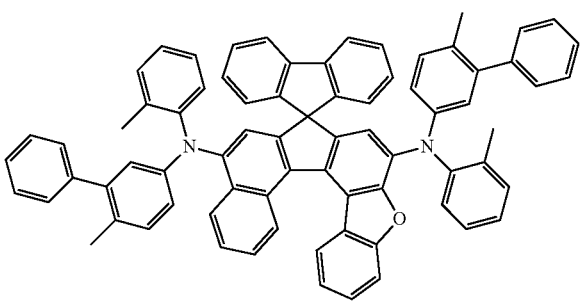
<84>
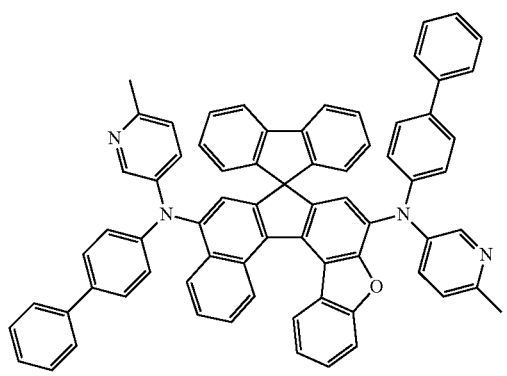
<85>
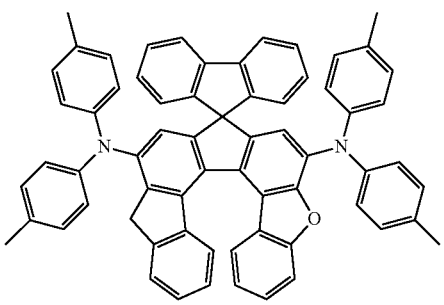
<86>
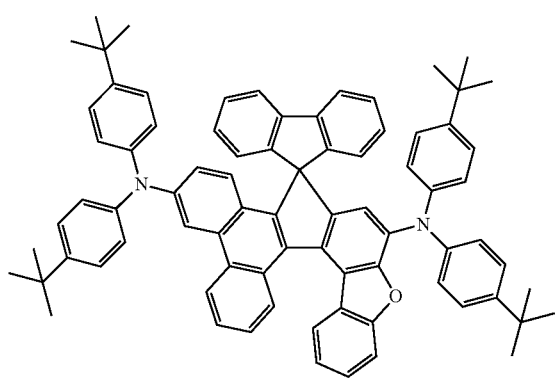
<87>
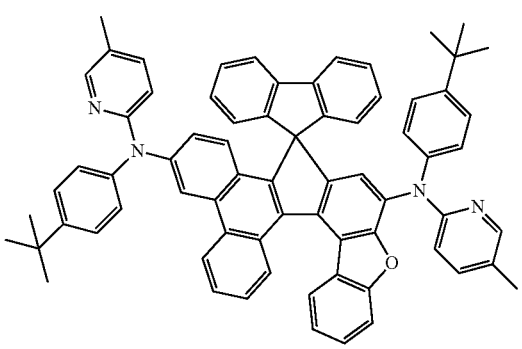

-continued
<88>
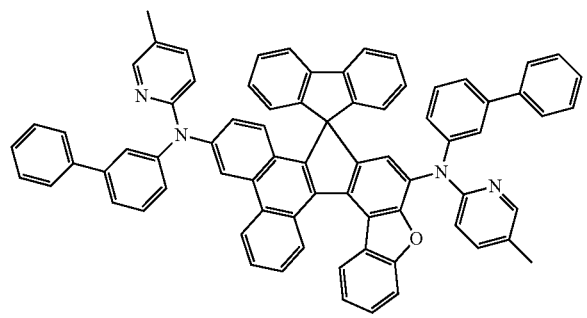
<89>
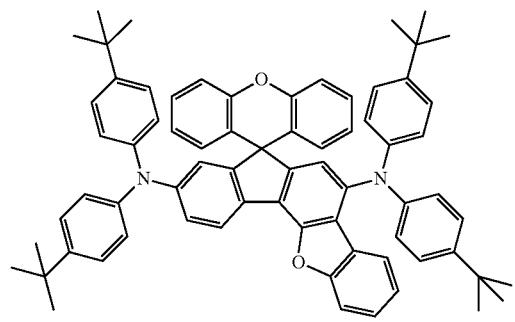
<90>
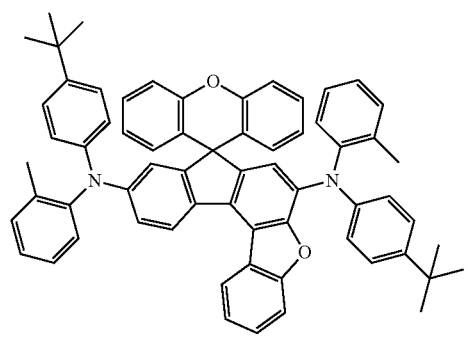
<91>
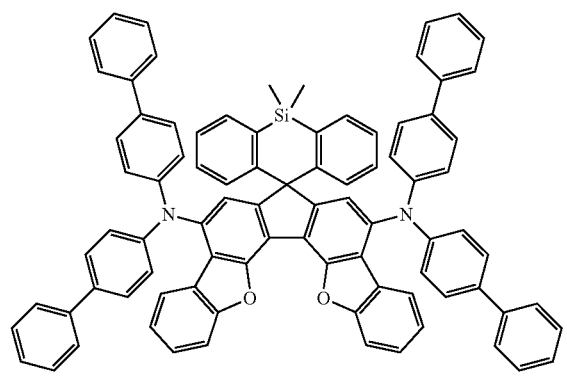
<92>
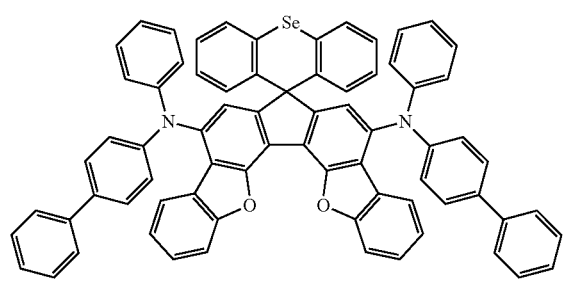
<93>
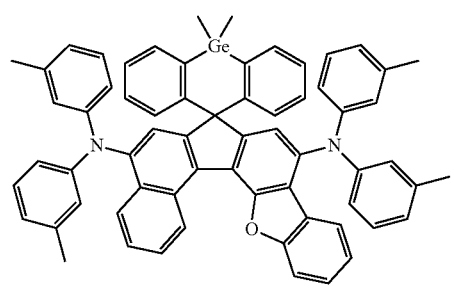
<94>
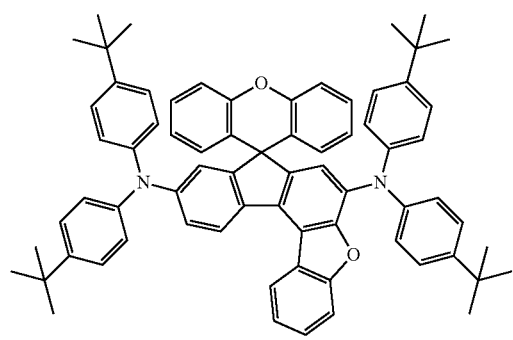
<95>
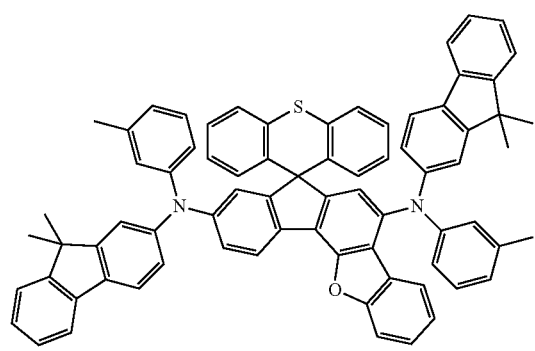

-continued
<96>
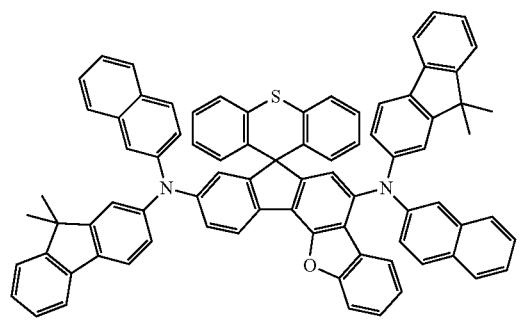
<97>
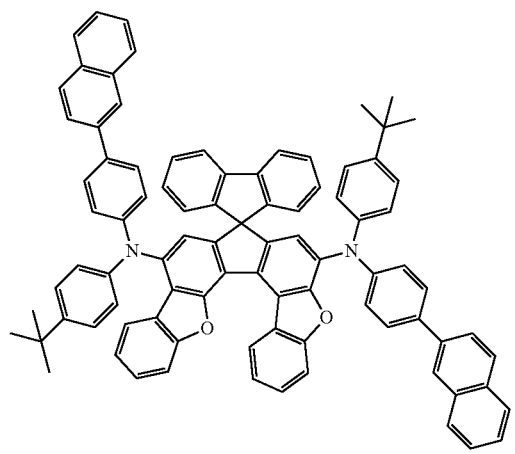
<98>
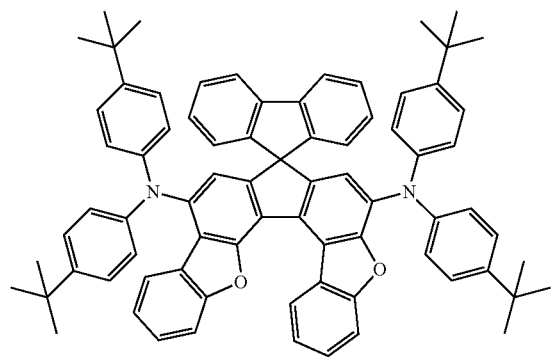
<99>
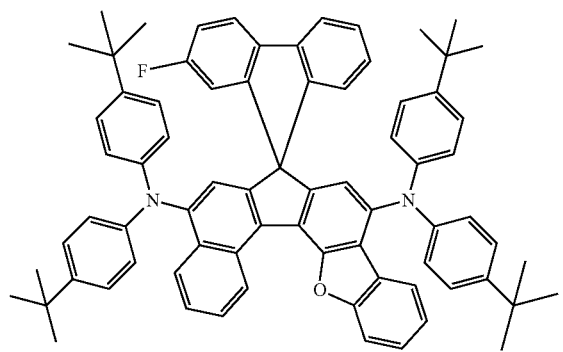
<100>
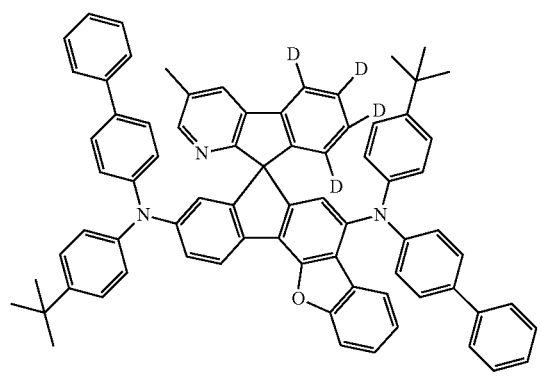
<101>
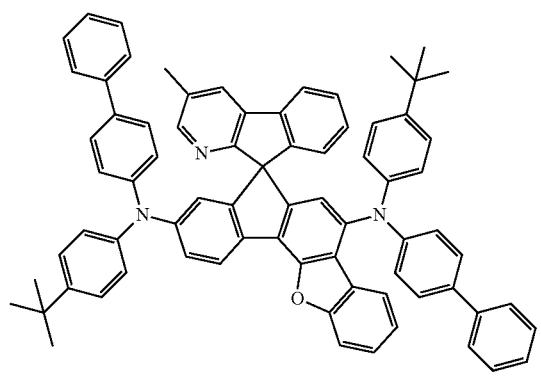

-continued
<102>
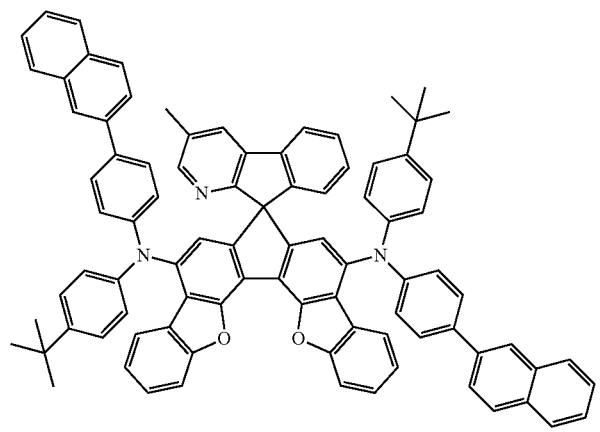
<103>
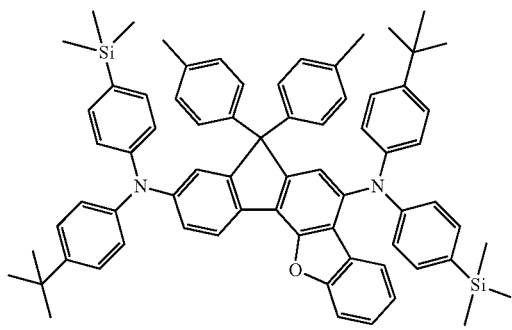
<104>
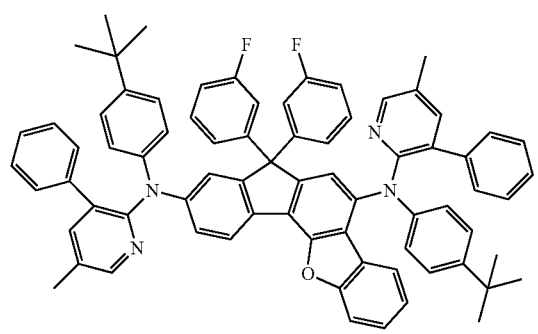
<105>
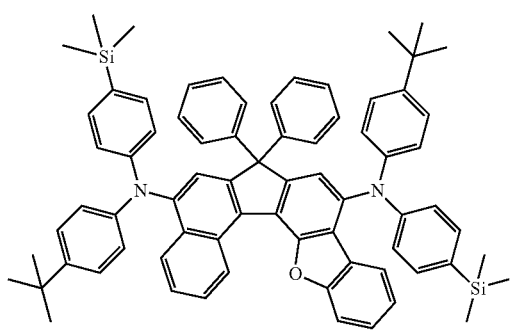
<106>
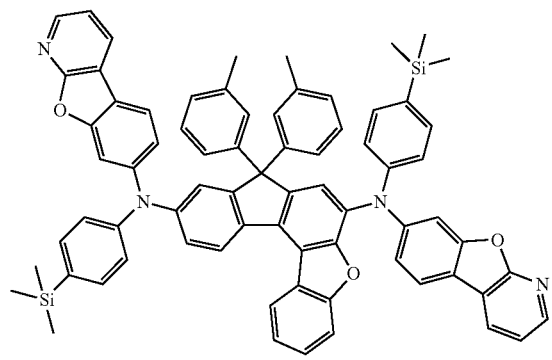
<107>
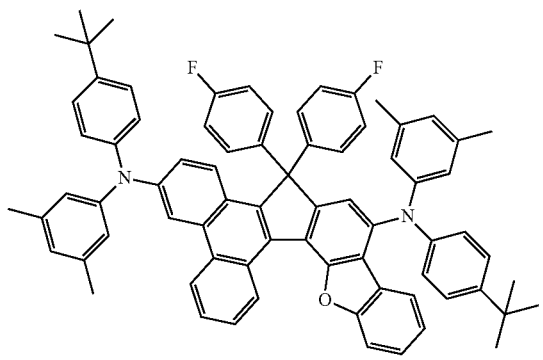
<108>
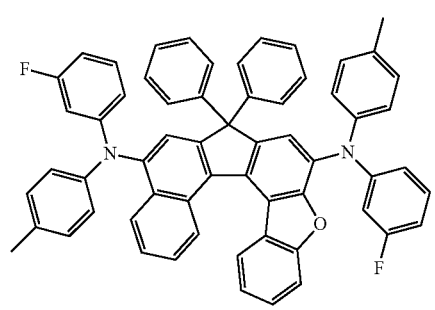
<109>
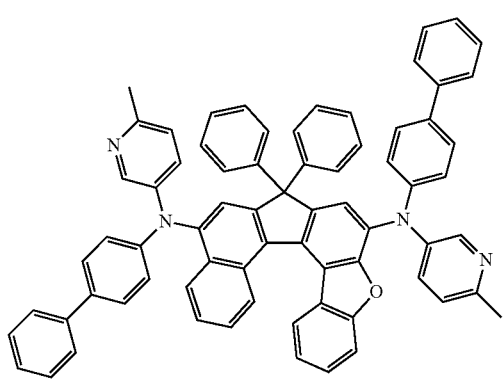

-continued
<110>
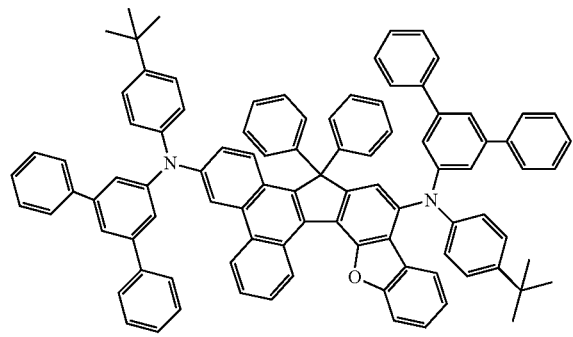
<111>
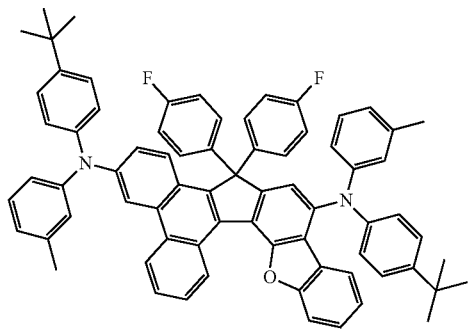
<112>
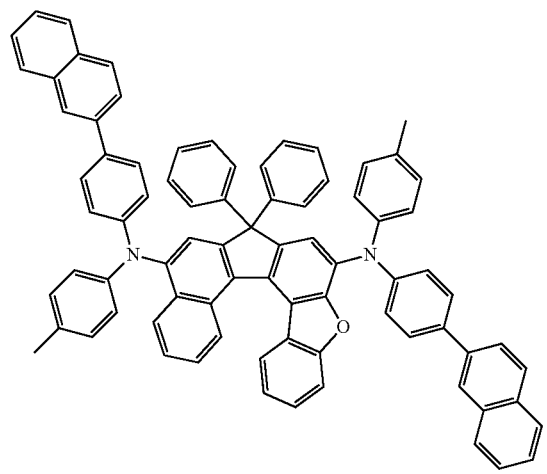
<113>
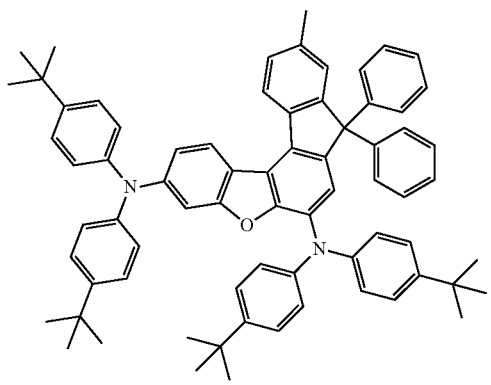
<114>
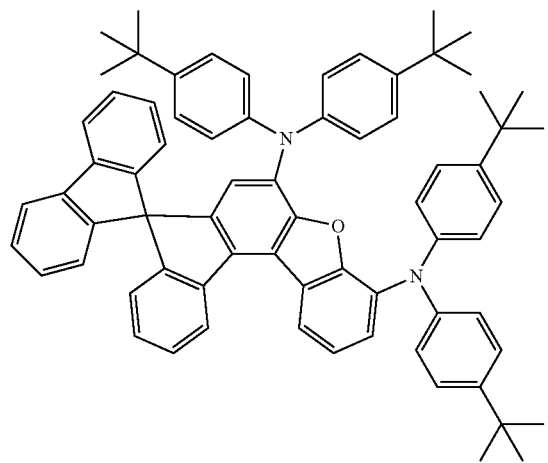
<115>
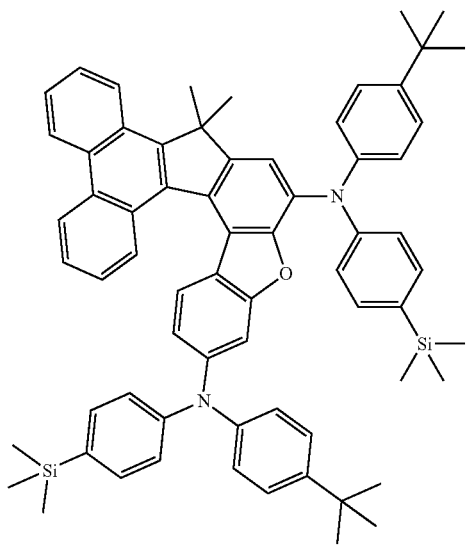

-continued
<116>
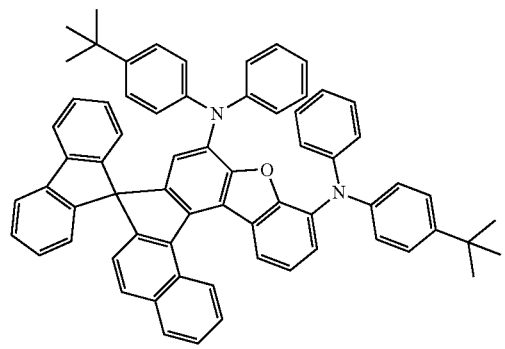
<117>
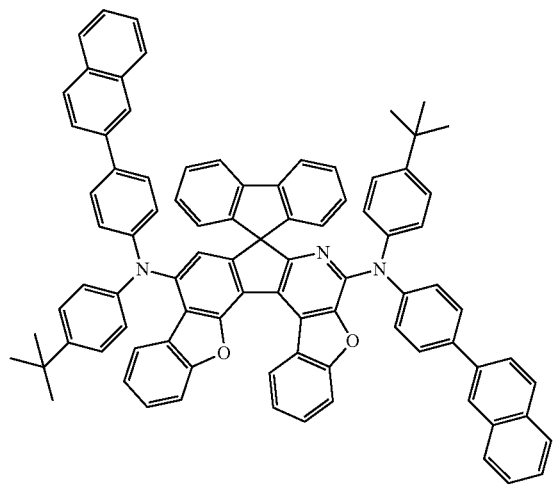
<118>
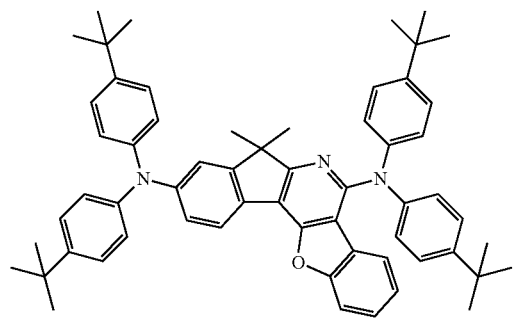
<119>
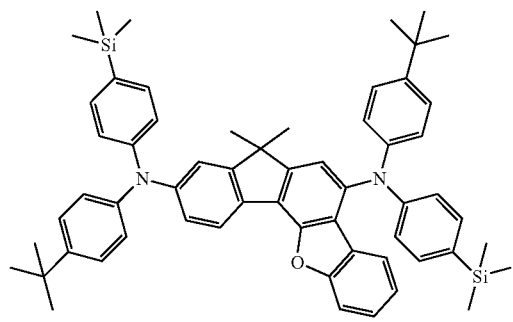
<120>
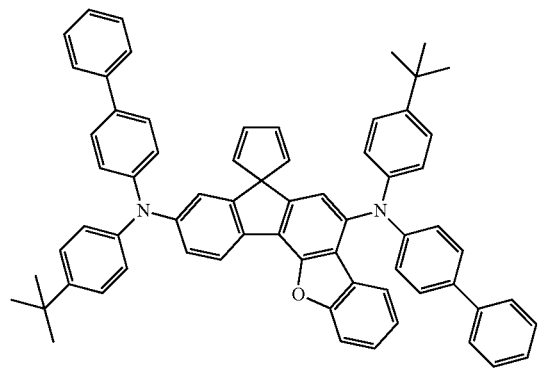
<121>
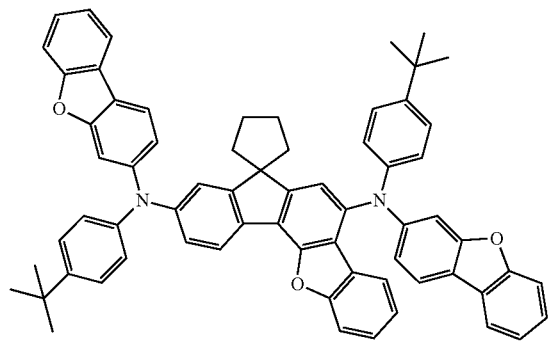
<122>
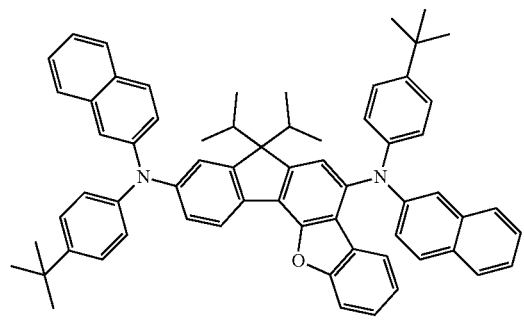
<123>
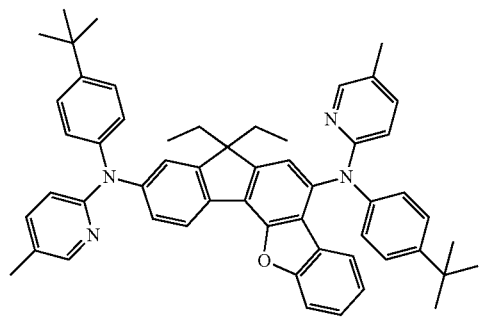

-continued
<124>
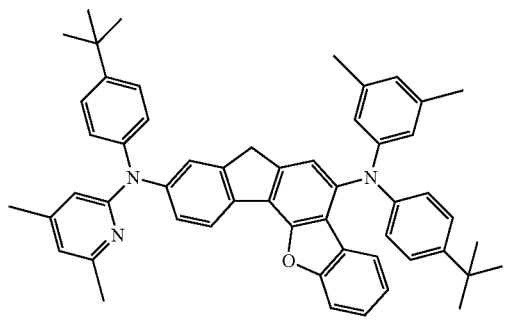
<125>
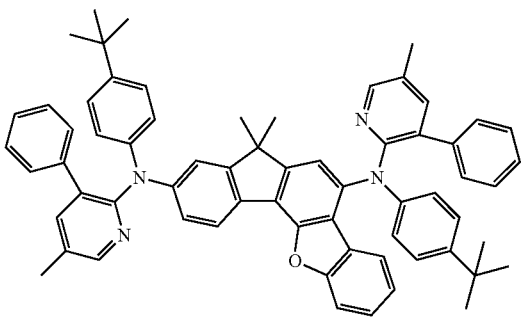
<126>
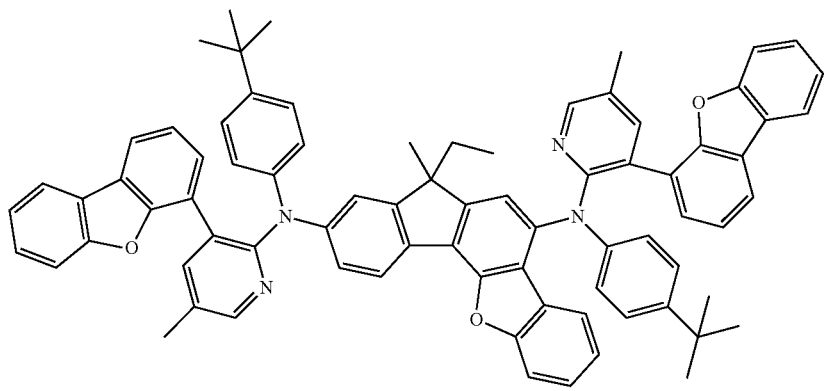
<127>
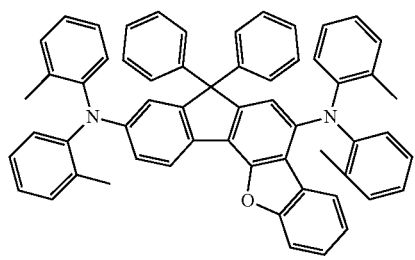
<128>
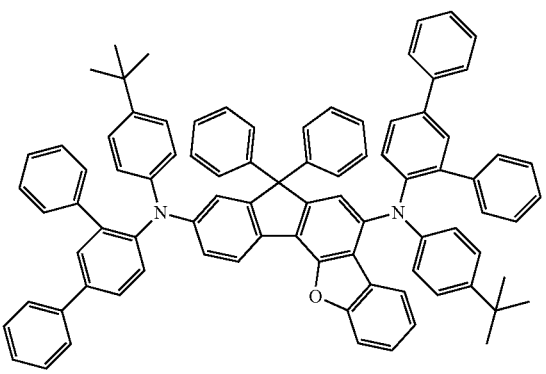
<129>
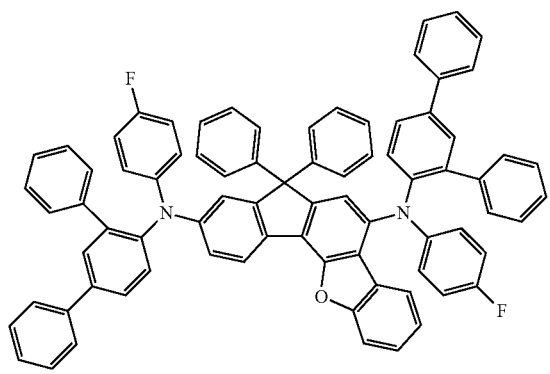
<130>
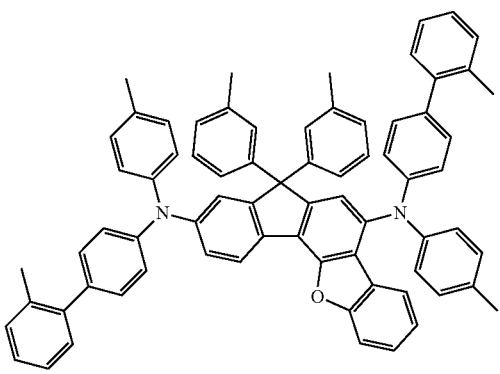

-continued
<131>
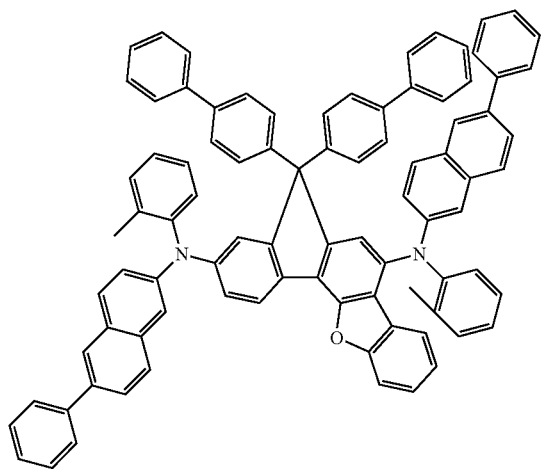
<132>
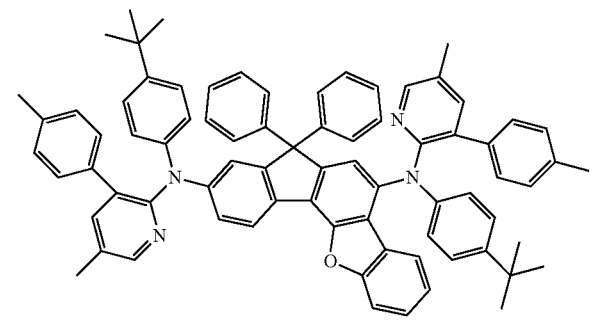
<133>
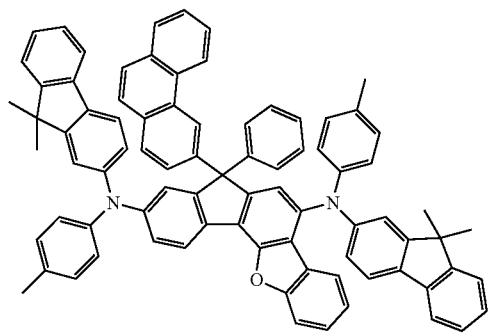
<134>
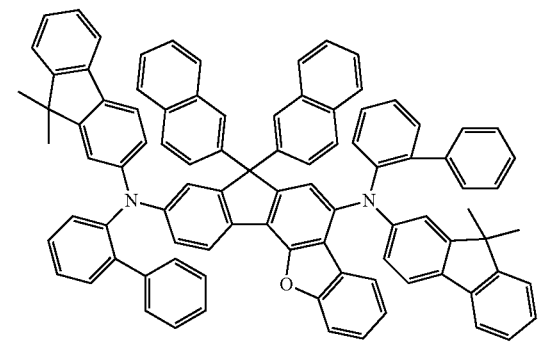
<135>
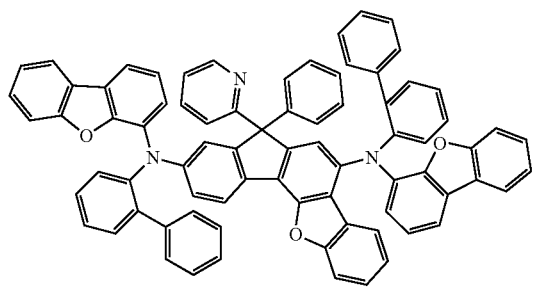
<136>
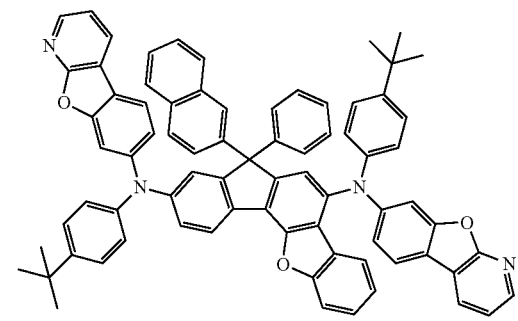
<137>
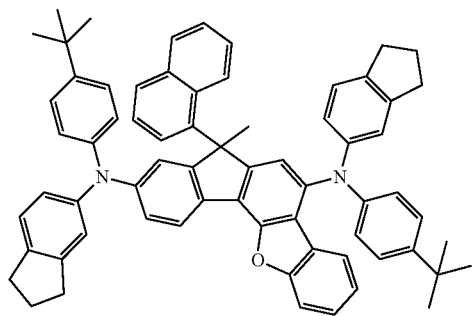
<138>
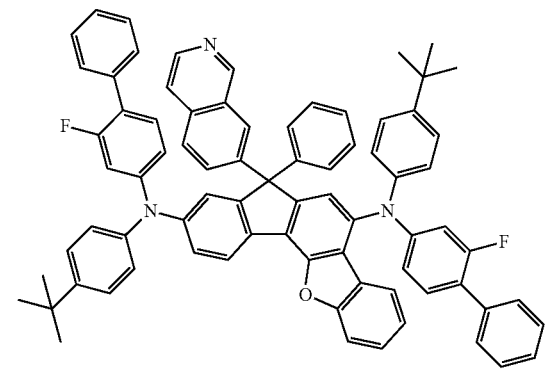

-continued
<139>
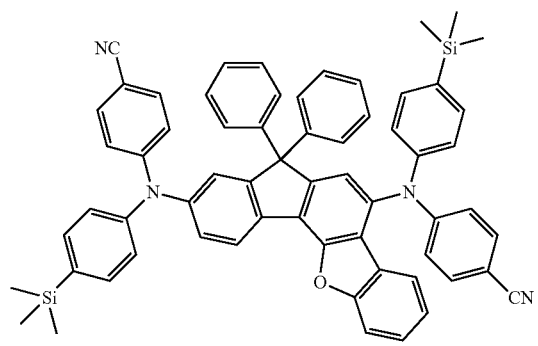
<140>
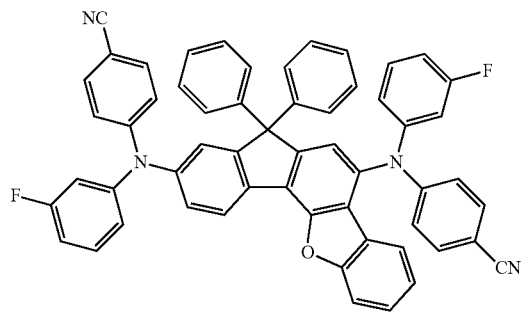
<141>
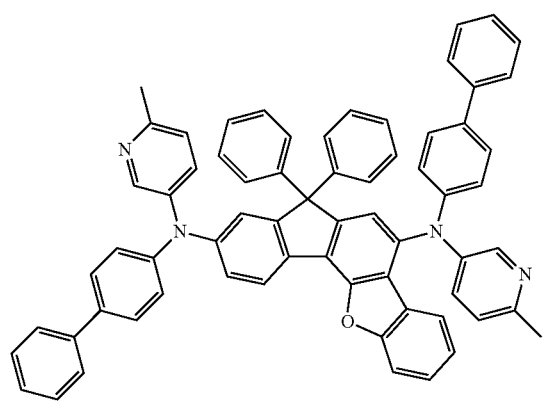
<142>
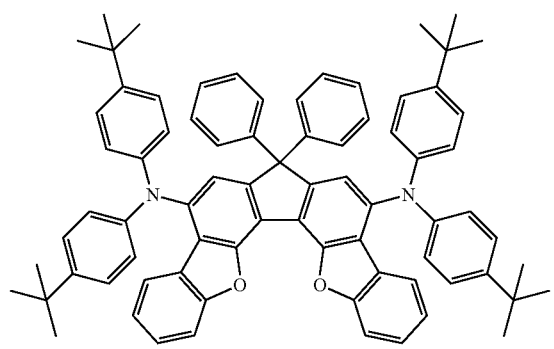
<143>
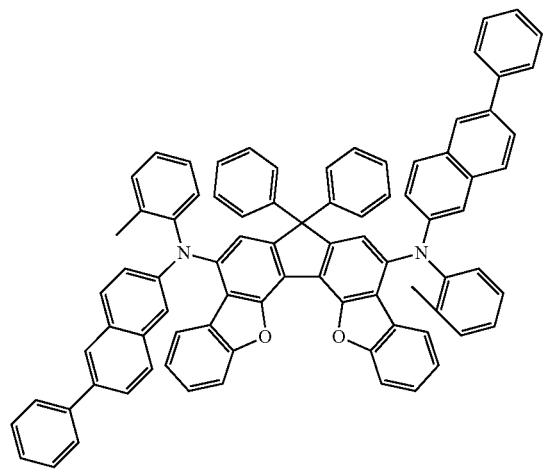
<144>
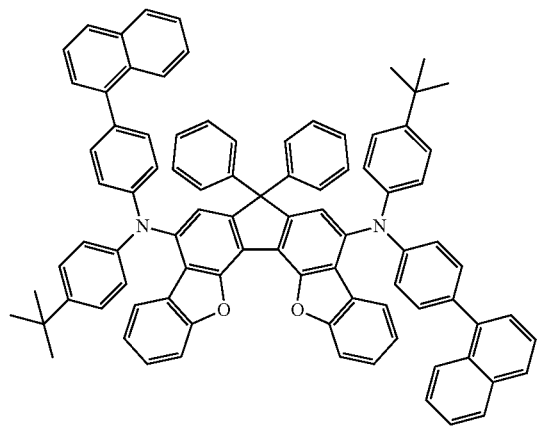
<145>
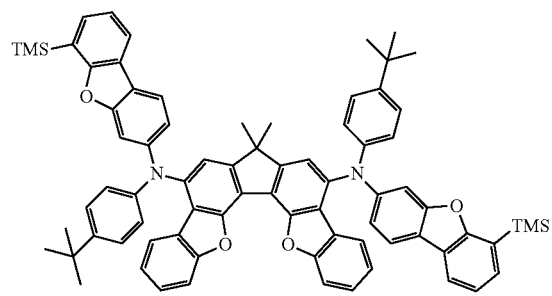
<146>
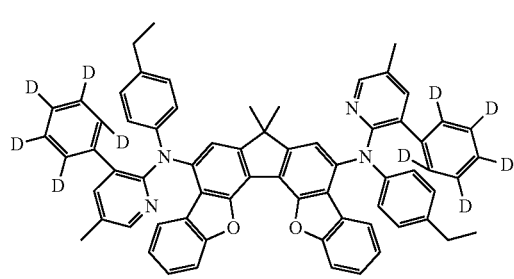

-continued
<147>
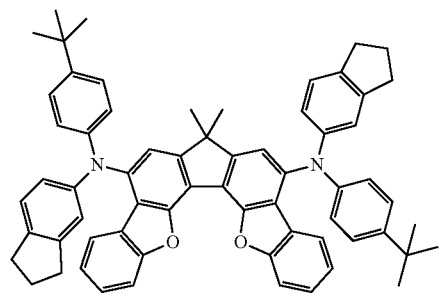
<148>
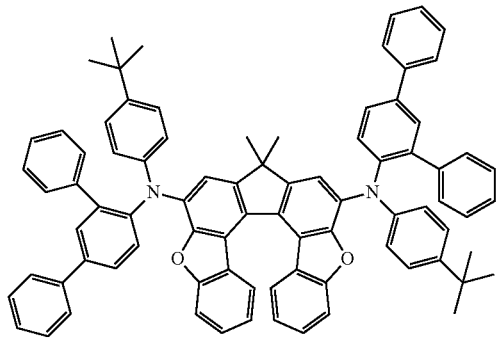
<149>
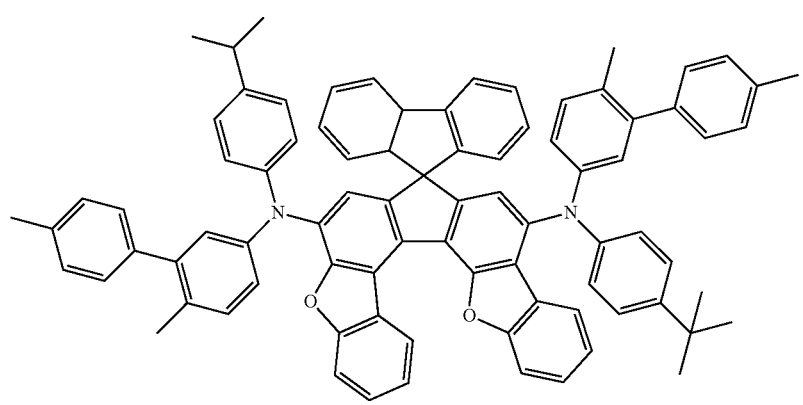
<150>
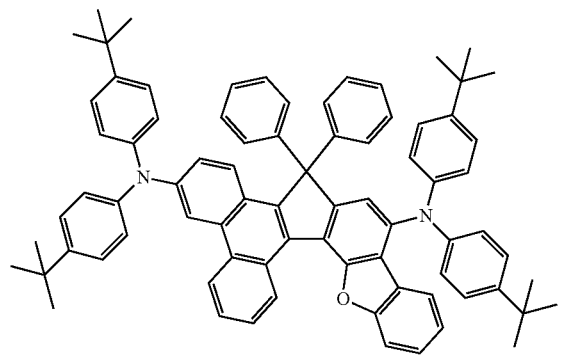
<151>
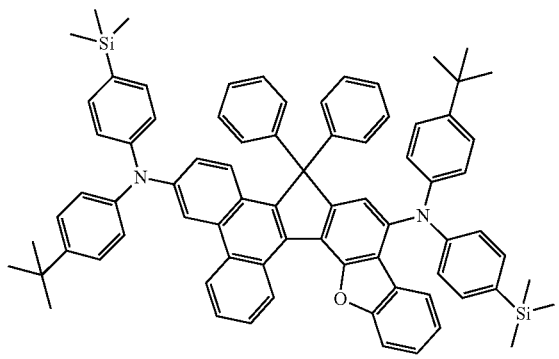
<152>
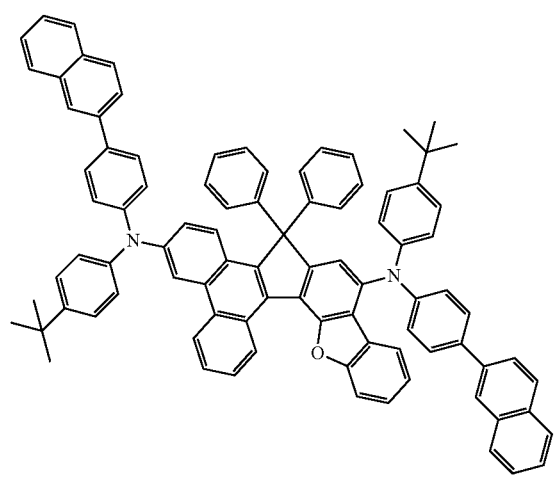
<153>
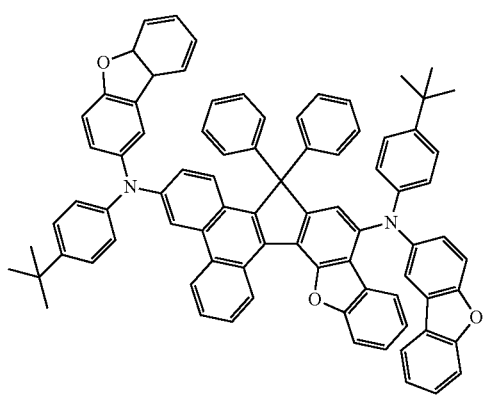

-continued
<154>
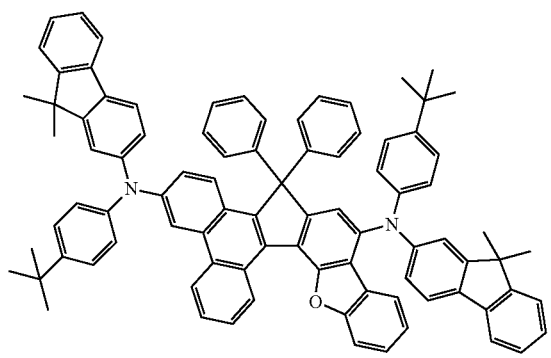
<155>
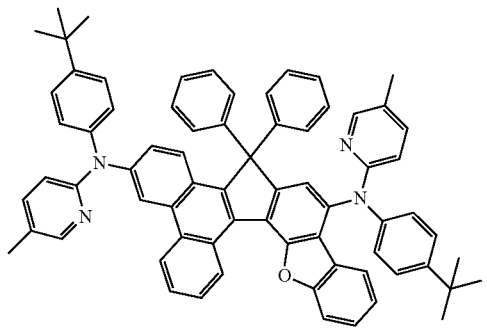
<156>
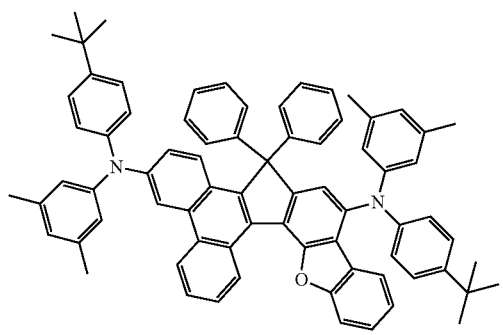
<157>
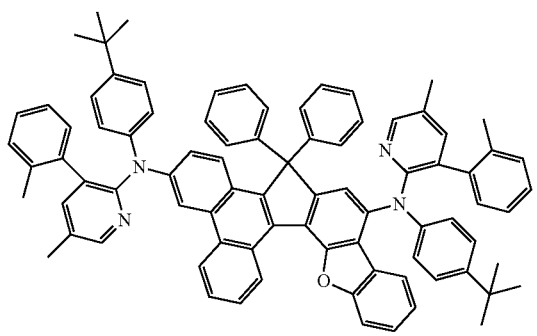
<158>
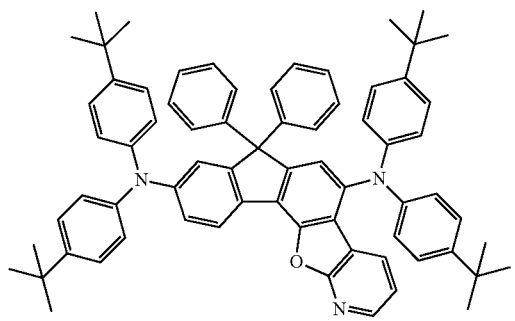
<159>
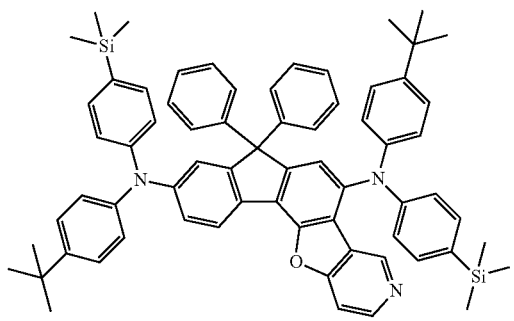
<160>
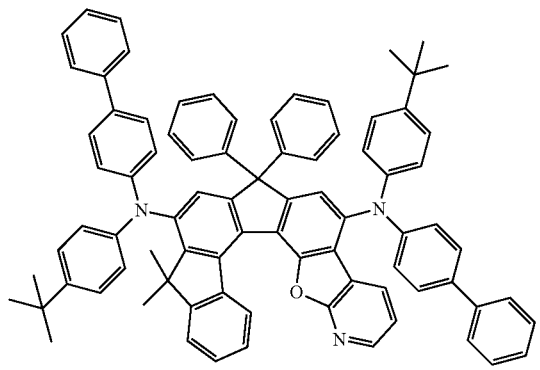
<161>
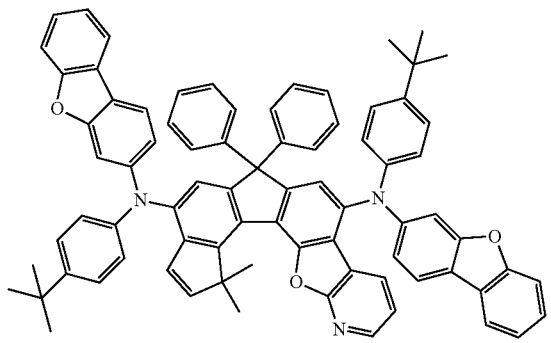

-continued
<162>
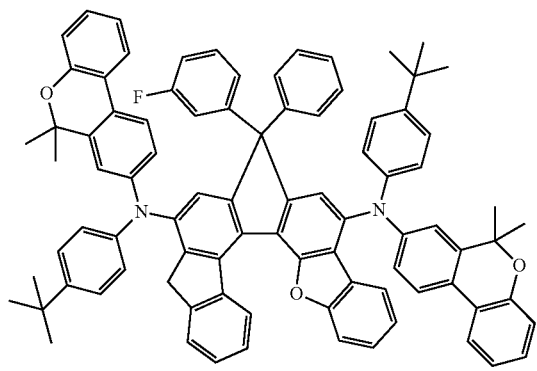
<163>
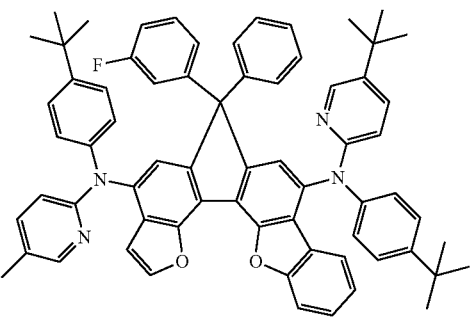
<164>
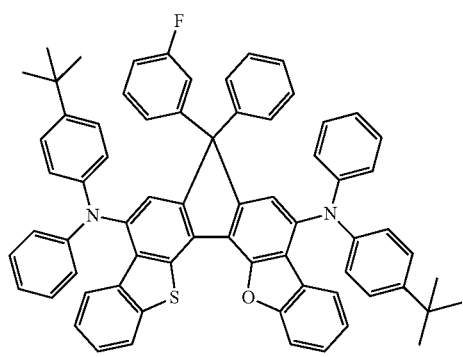
<165>
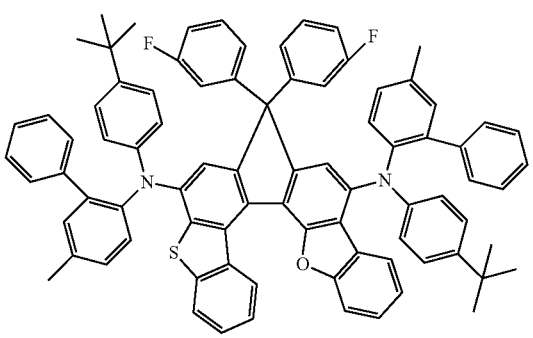
<166>
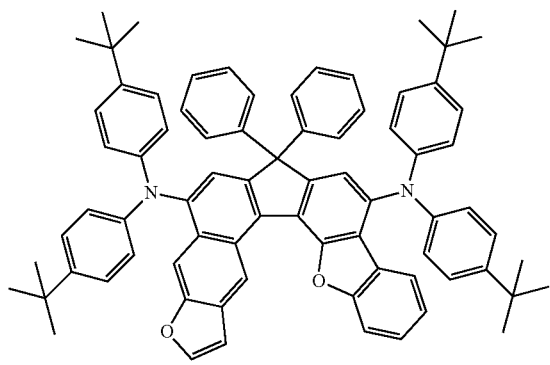
<167>
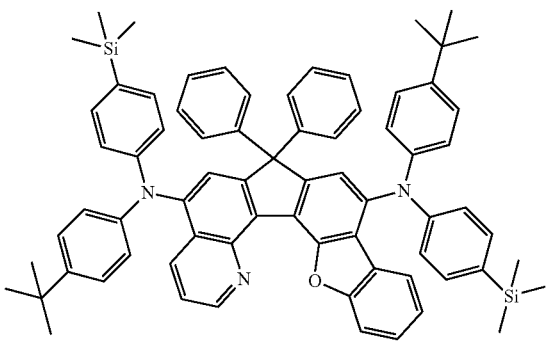
<168>
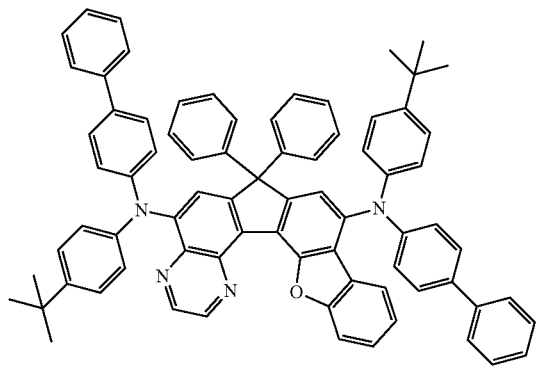
<169>
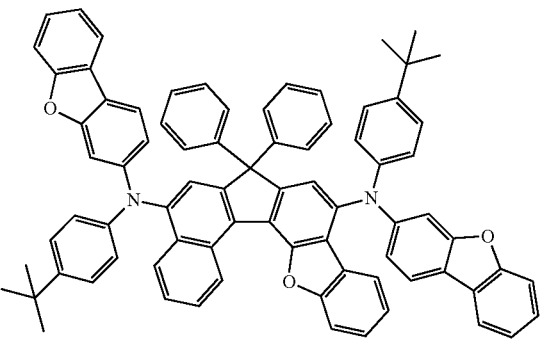

-continued
<170>
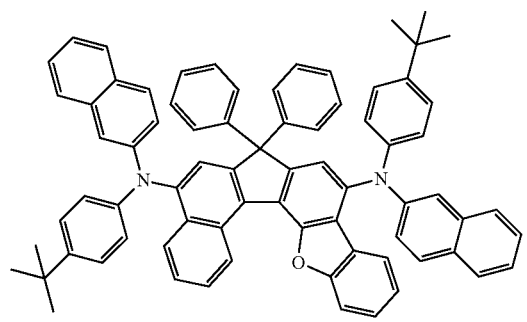
<171>
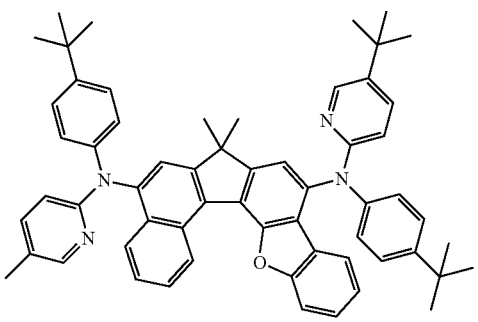
<172>
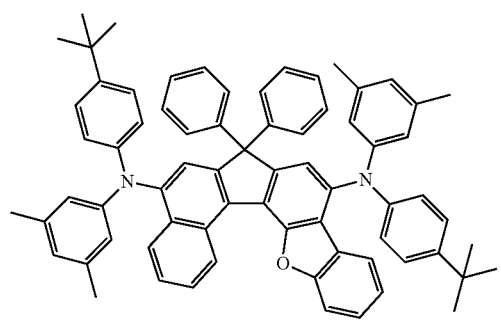
<173>
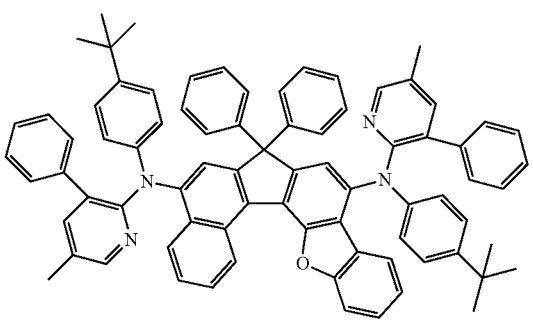
<174>
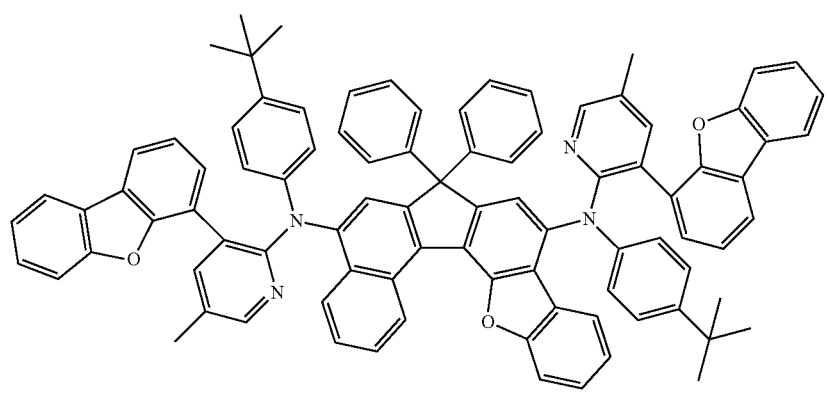
<175>
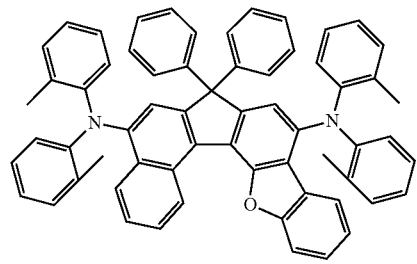
<176>
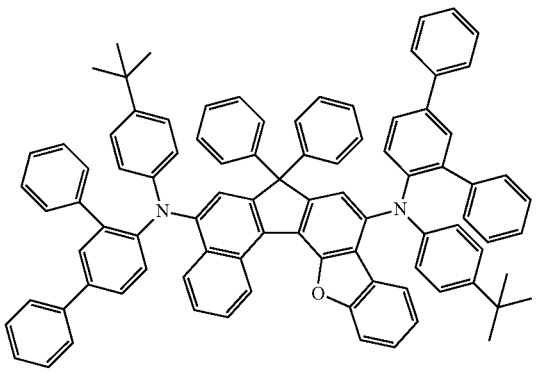

-continued
<177>
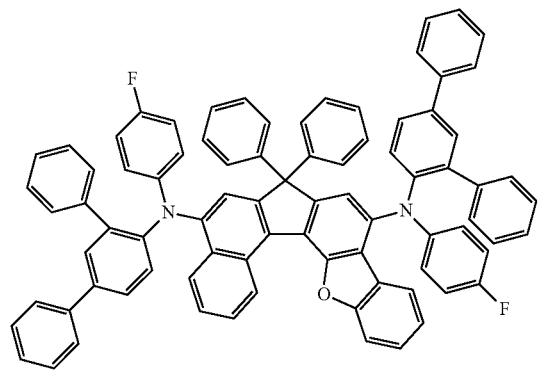
<178>
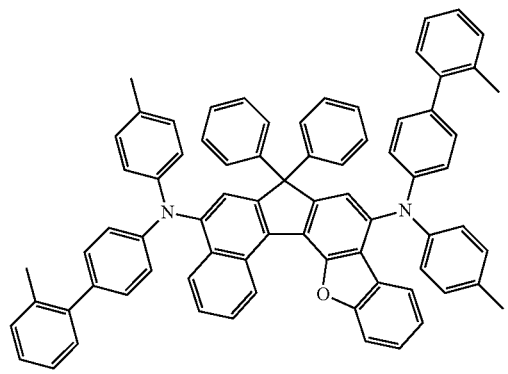
<179>
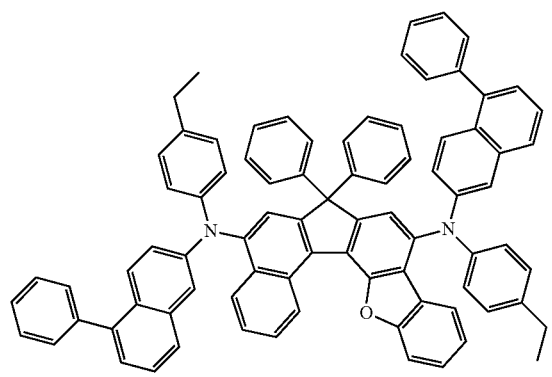
<180>
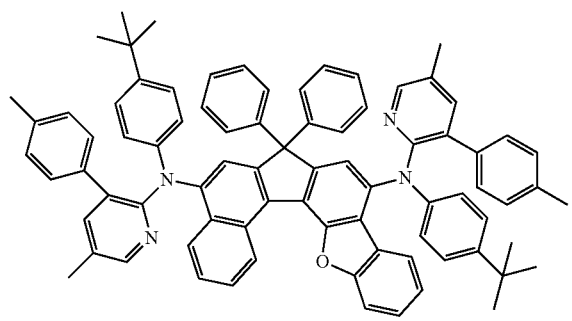
<181>
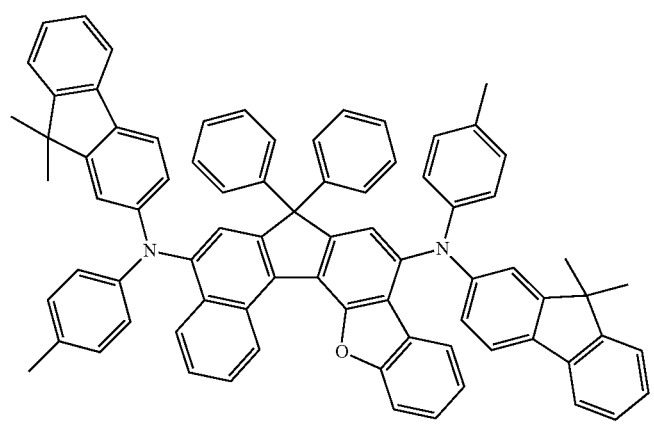

-continued
<182>
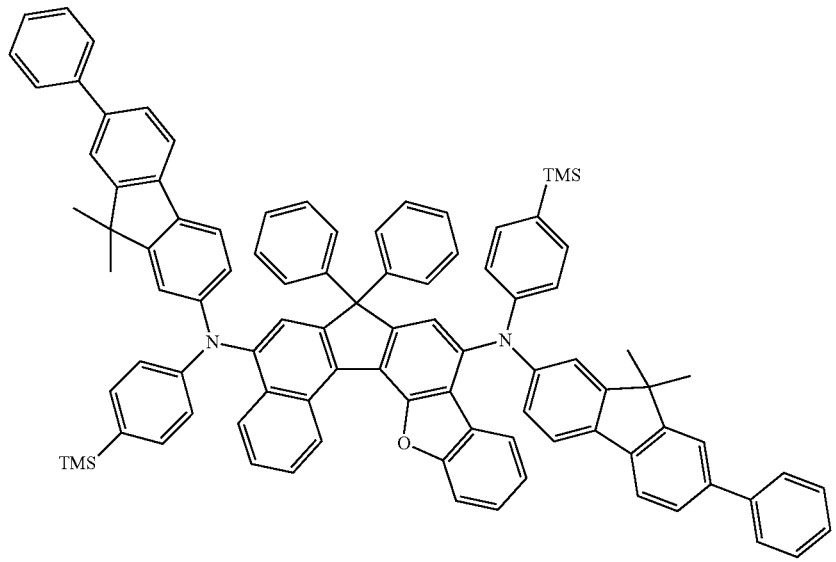
<183>
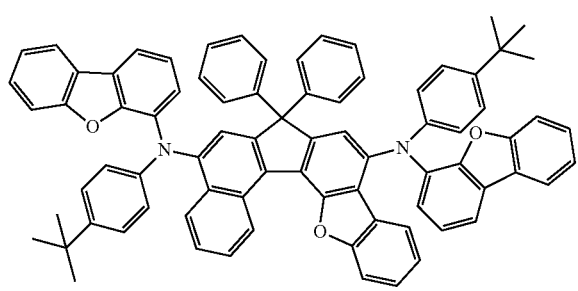
<184>
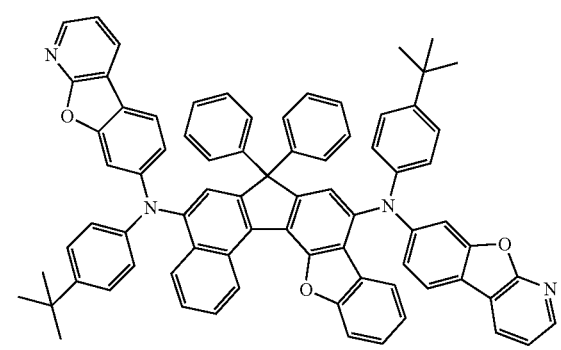
<185>
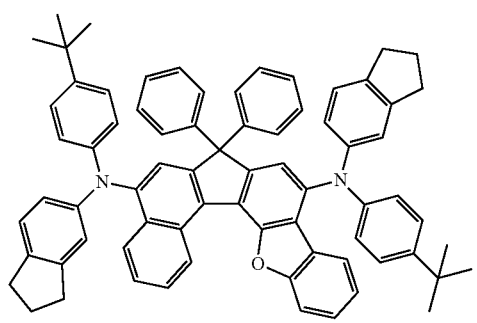
<186>
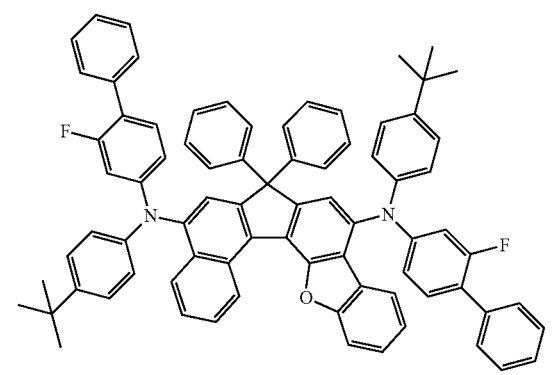
<187>
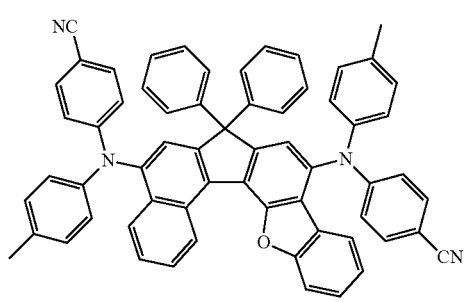
<188>
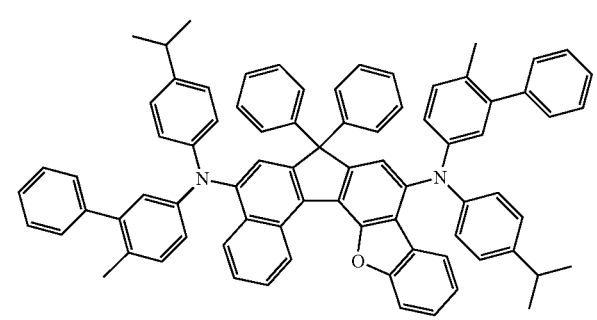

-continued
<189>
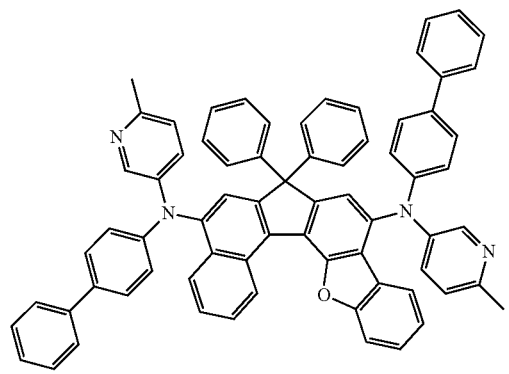
<190>
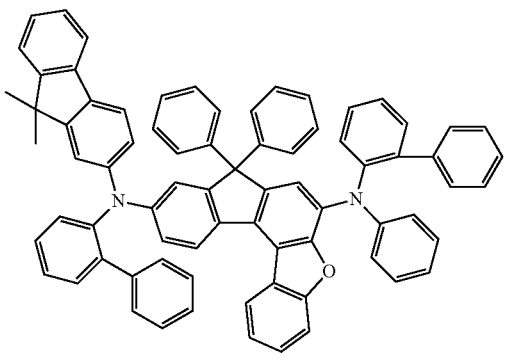
<191>
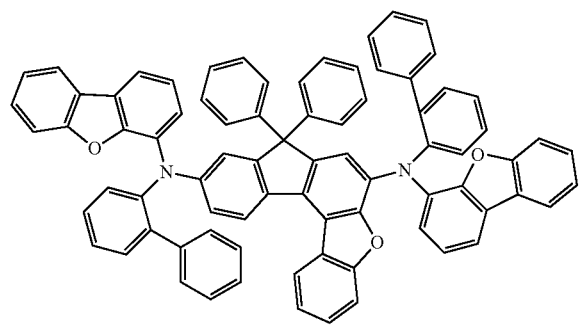
<192>
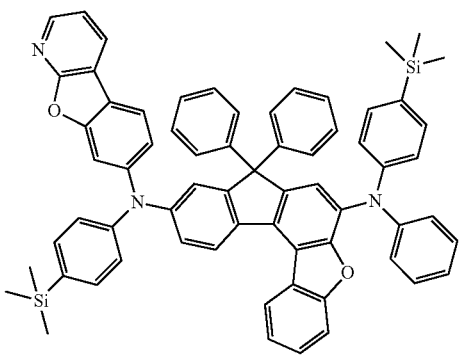
<193>
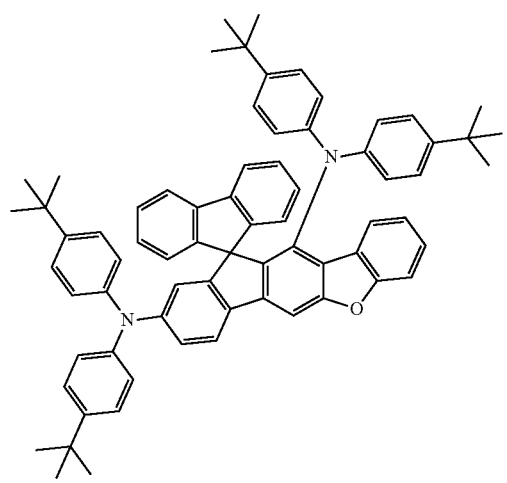
<194>
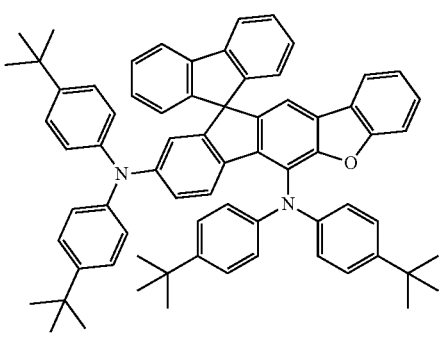

<195>
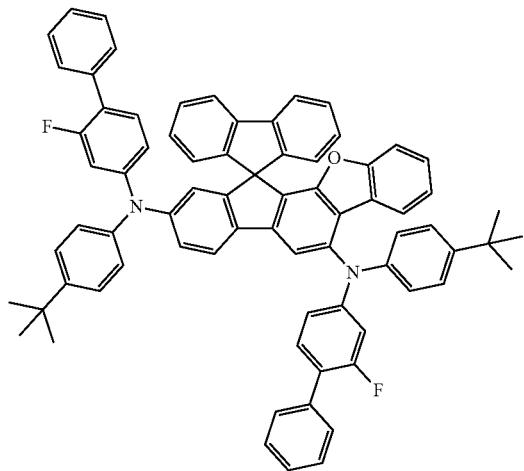
<196>
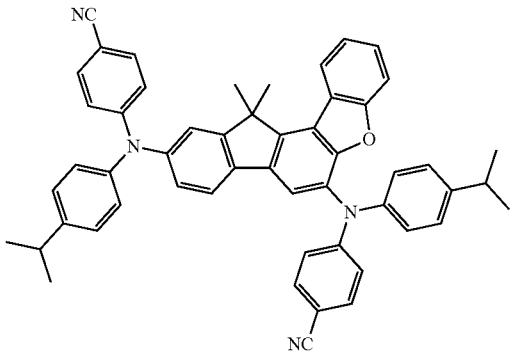
<197>
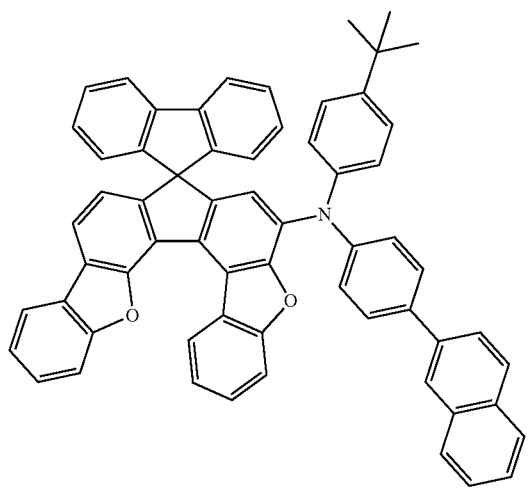
<198>
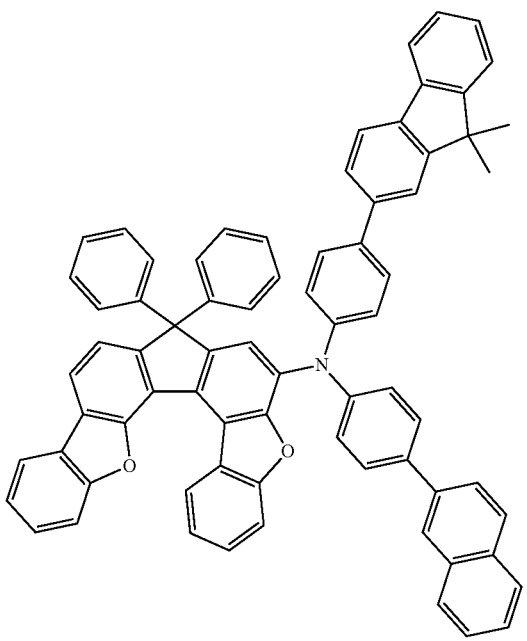

-continued
<199>
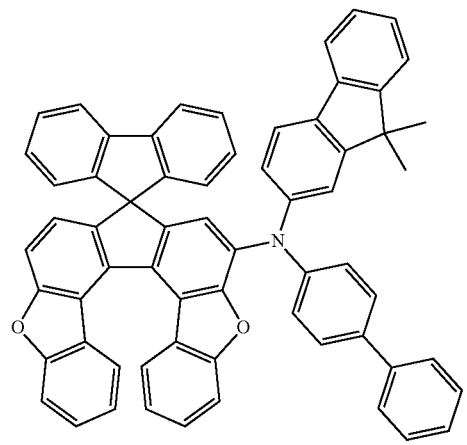
<200>
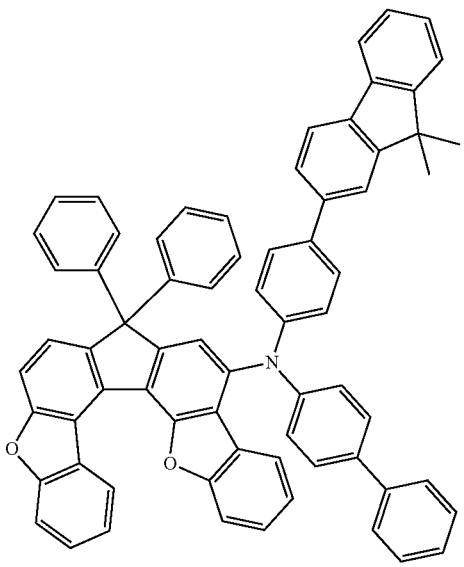
<201>
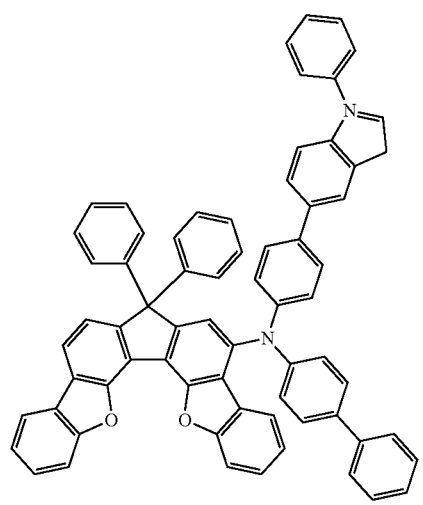
<202>
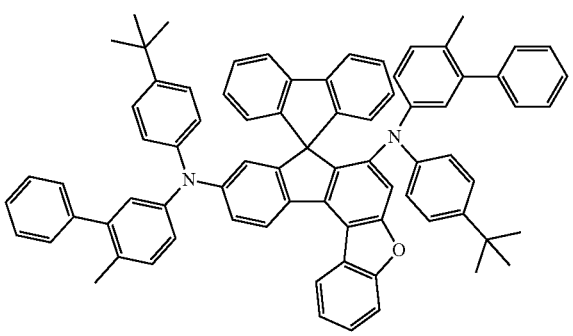
<203>
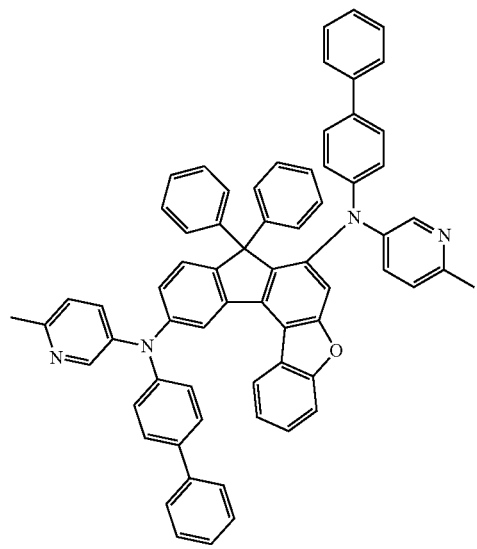
<204>
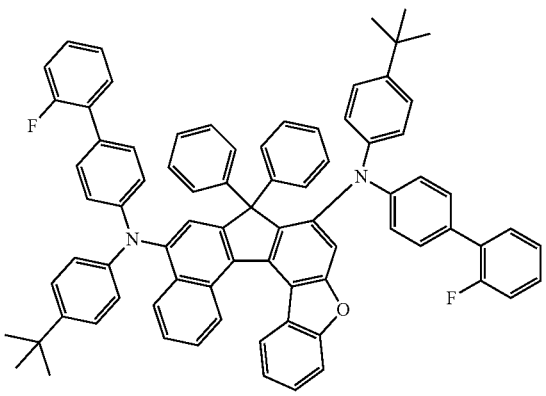

<205>
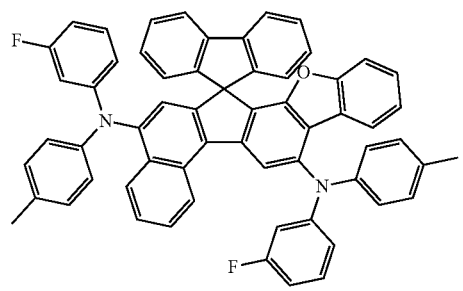
<206>
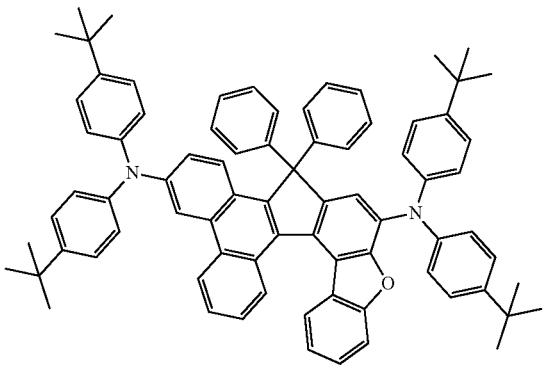
<207>
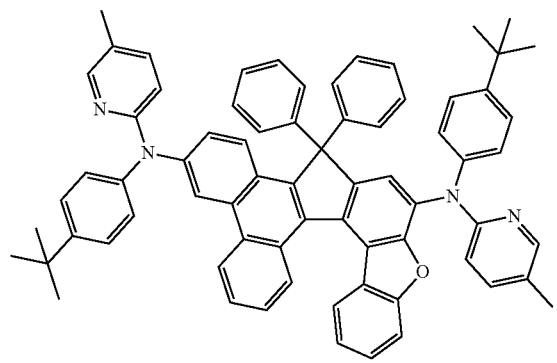
<208>
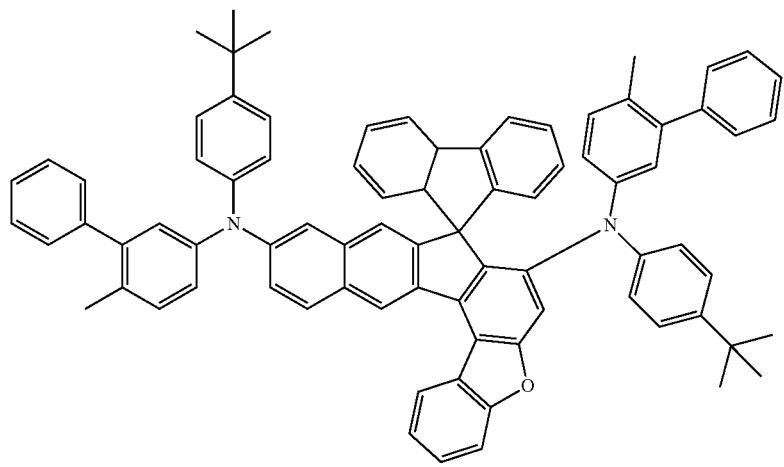
<209>
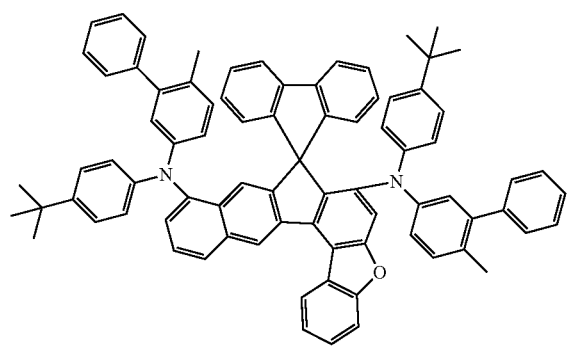
<210>
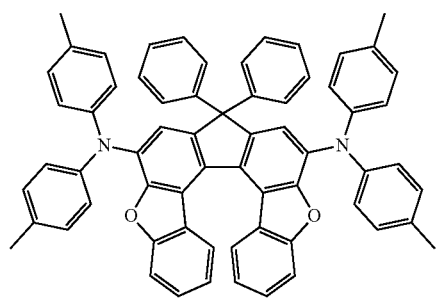

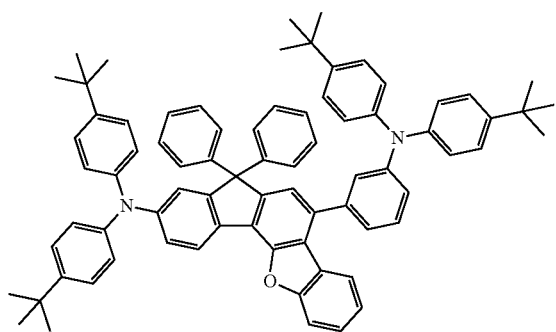
<211>
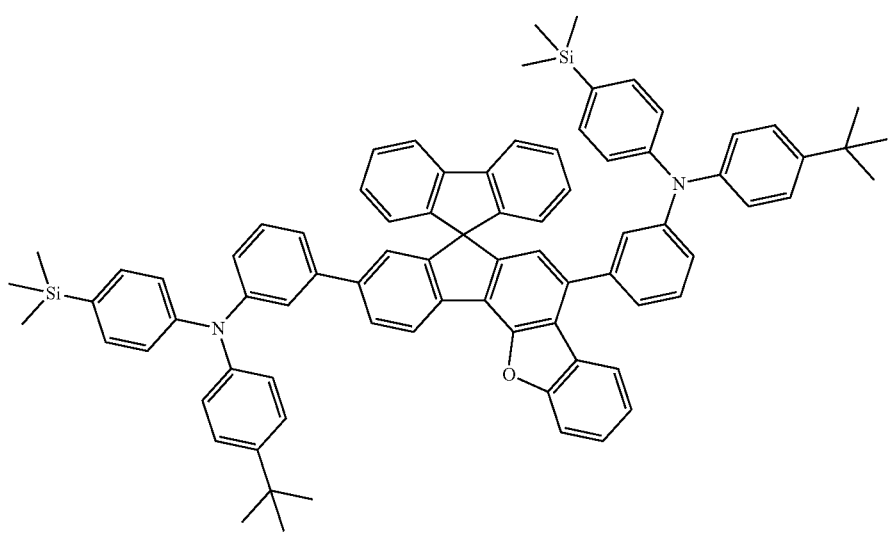
<212>
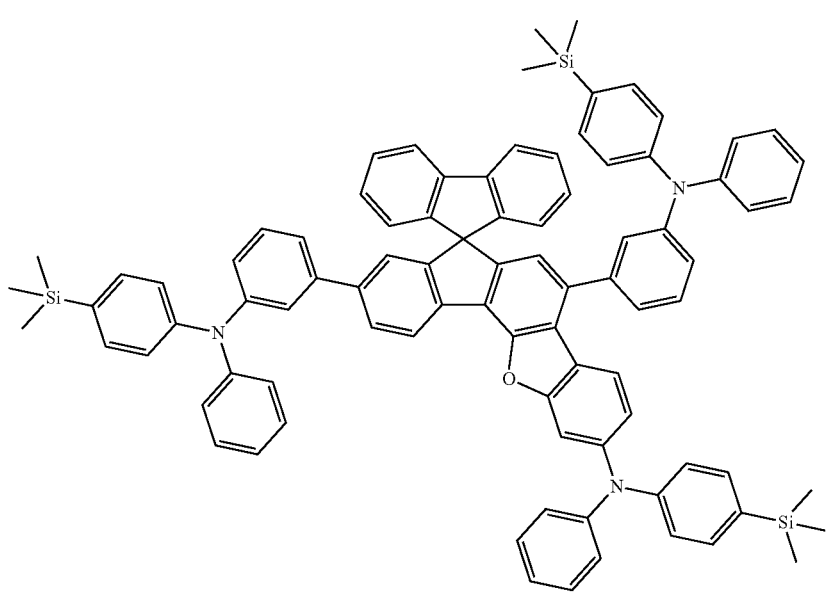
<213>

-continued
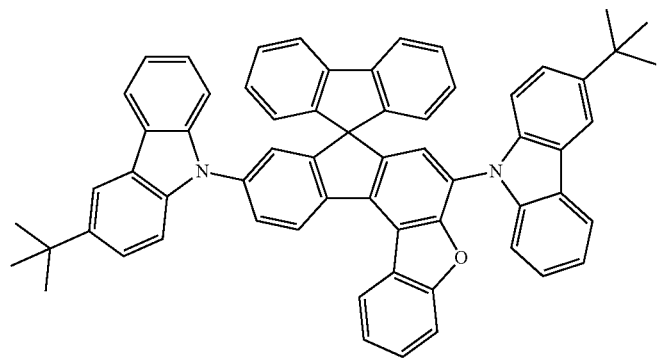
<214>
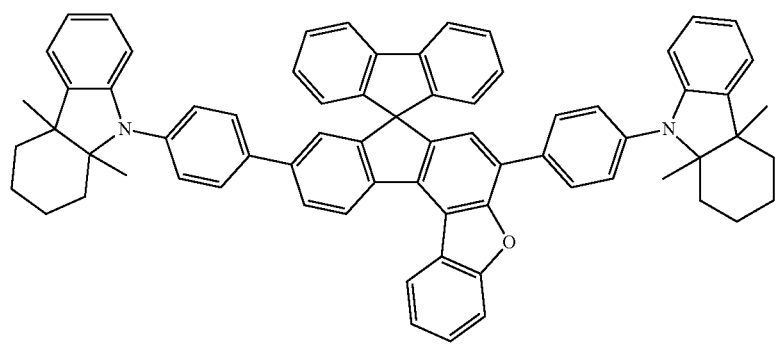
<215>
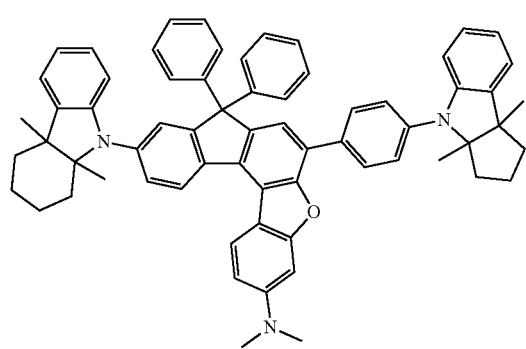
<216>
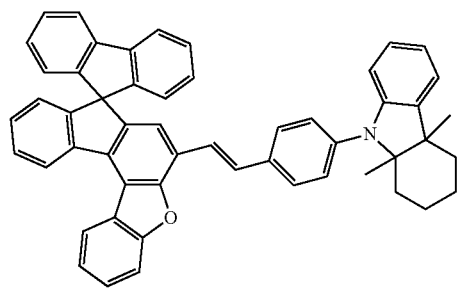
<217>
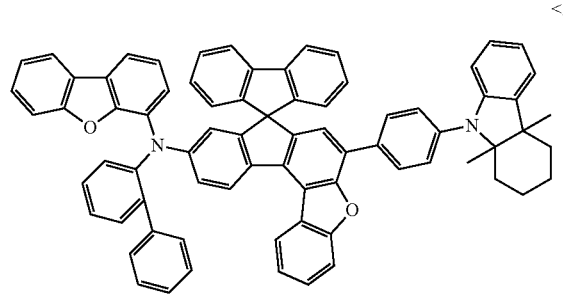
<218>
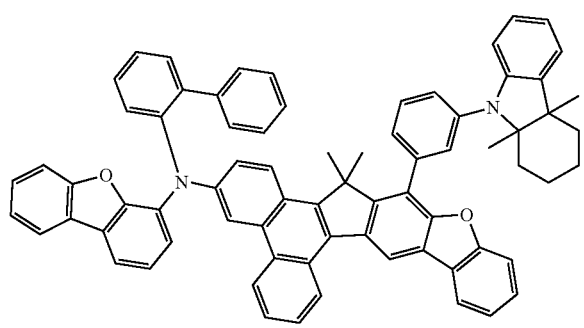
<219>

-continued
<220>
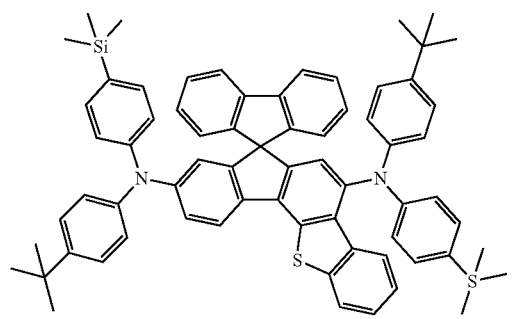
<221>
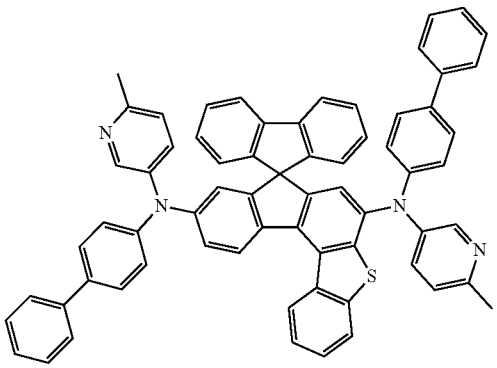
<222>
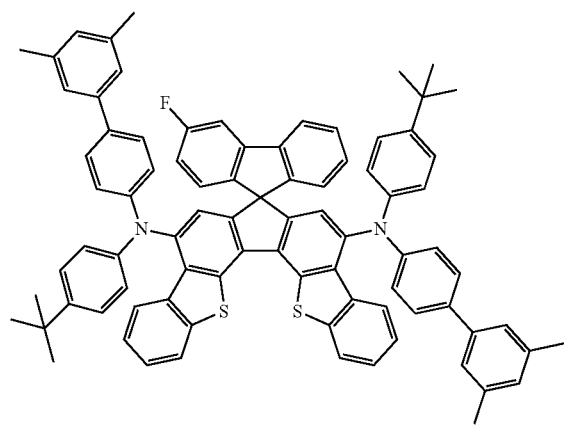
<223>
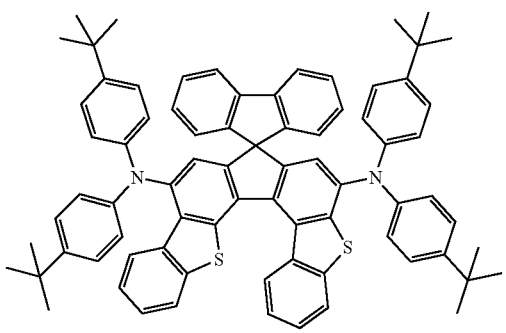
<224>
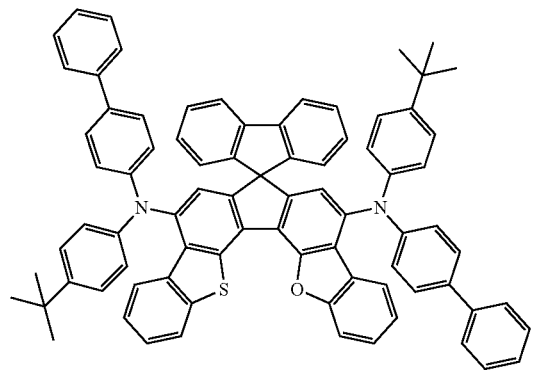
<225>
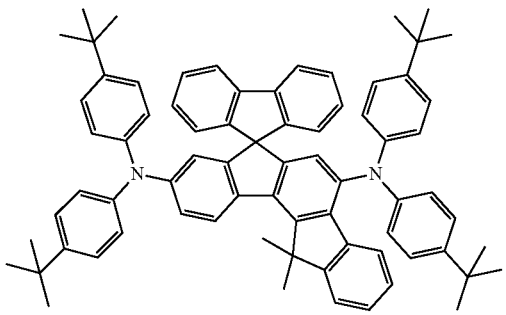
<226>
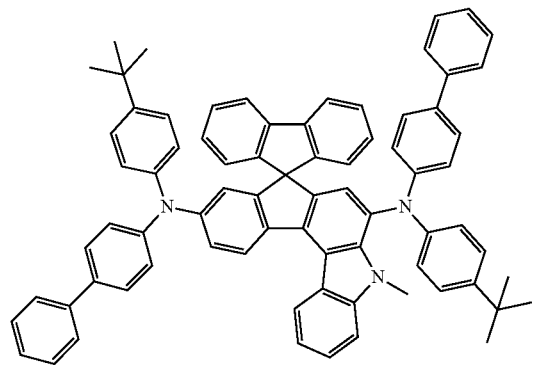
<227>
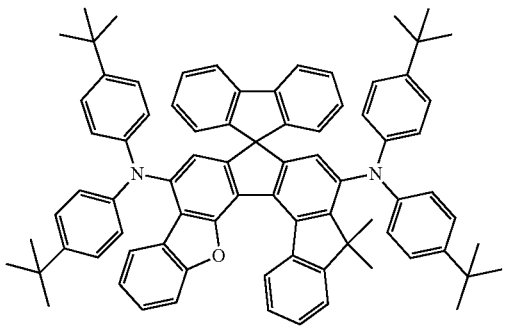

-continued
<228>
<229>
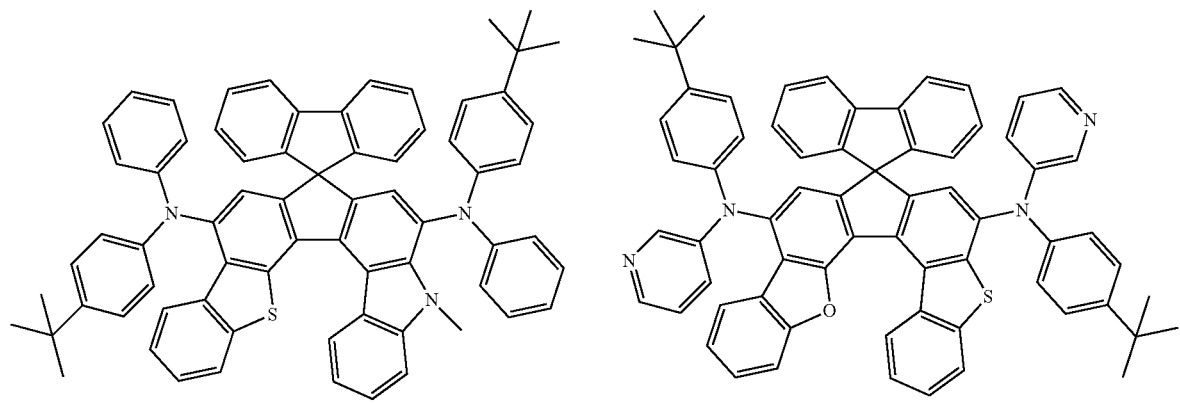
<230>
<231>
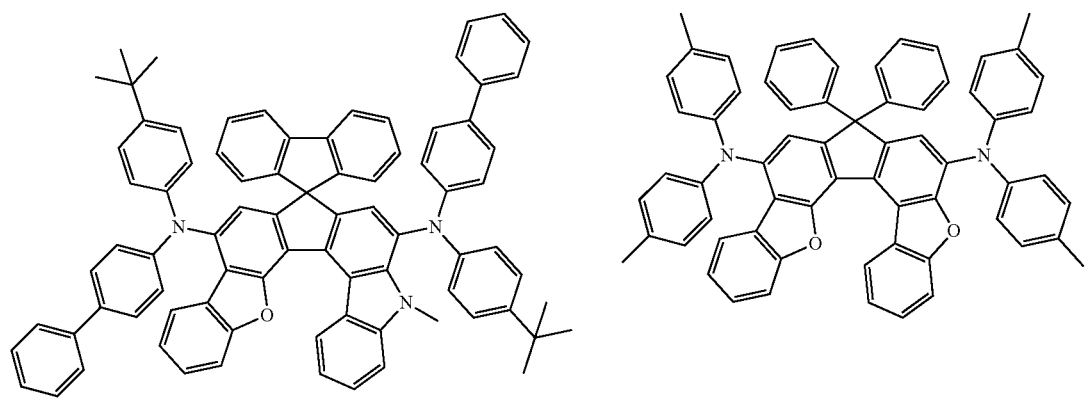
<232>
<233>
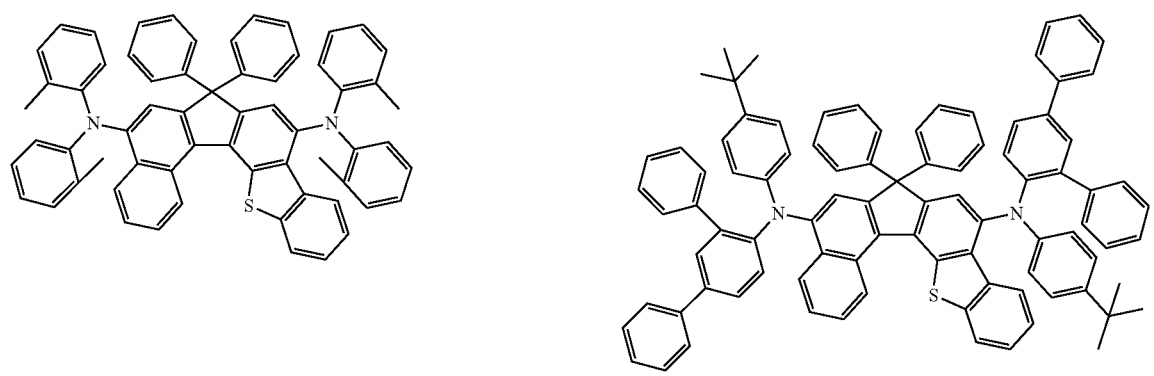
<234>
<235>
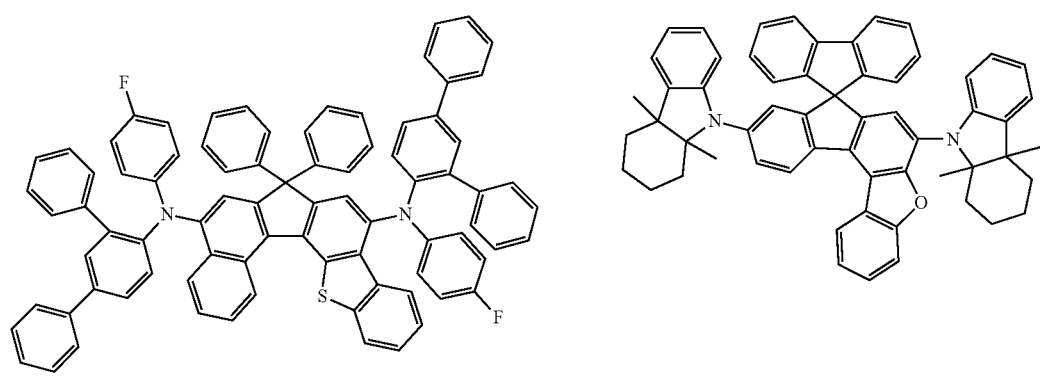

<236>
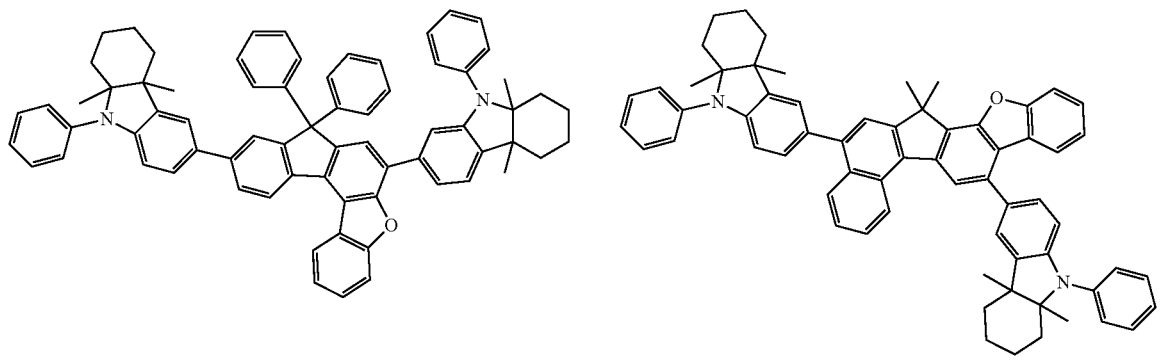
<237>
<238>
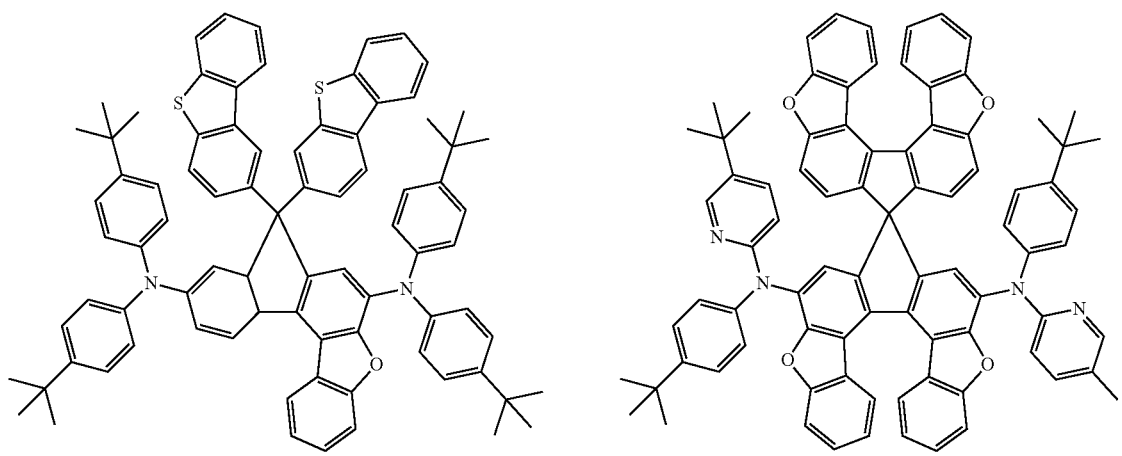
<239>
Further, the anthracene compound represented by Chemical Formula C may be any one selected from among the following Compounds 1 to 80.
Here, the compounds represented by Compounds 1 to 80 may be those known in the art or may correspond to those obtained from known compounds by the simply change of substituents.
[Cpd. 1]
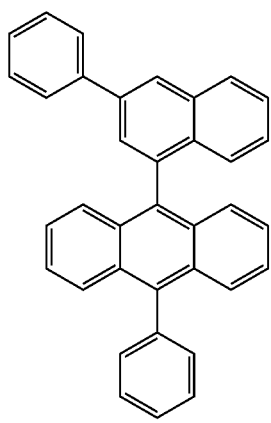
[Cpd. 2]
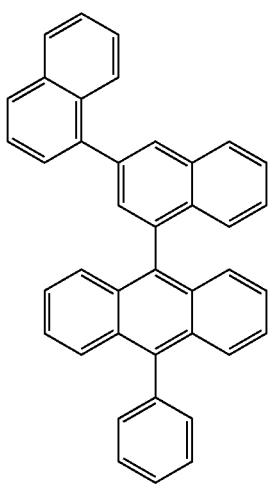
-continued

[Cpd. 3]
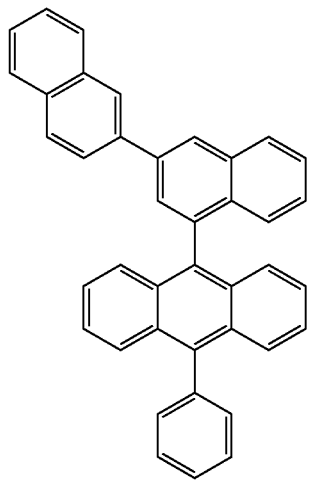
[Cpd. 4]
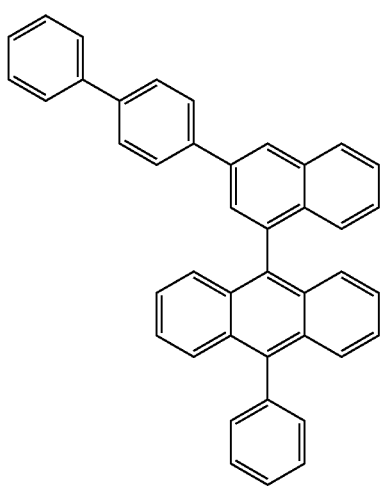
[Cpd. 5]
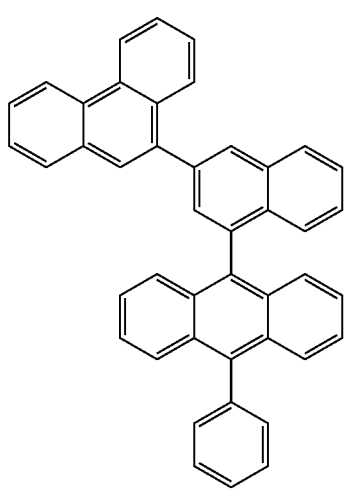
[Cpd. 6]
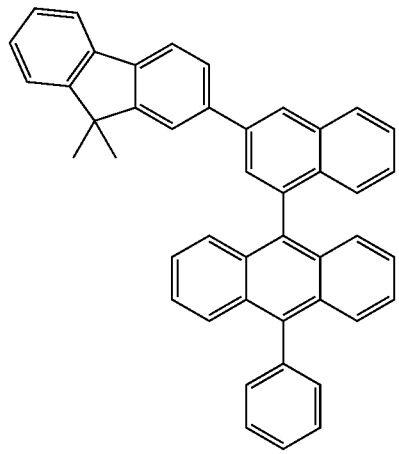
[Cpd. 7]
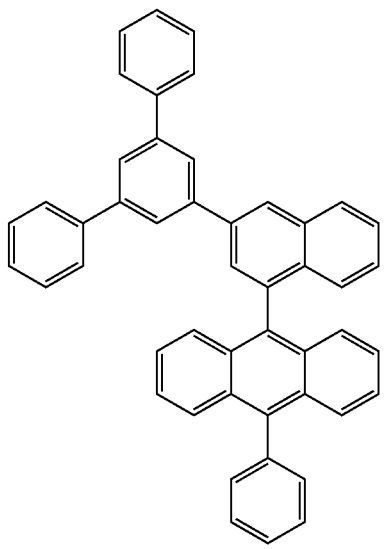
[Cpd. 8]
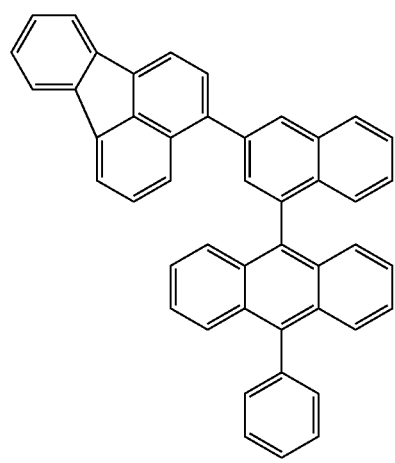

[Cpd. 9]
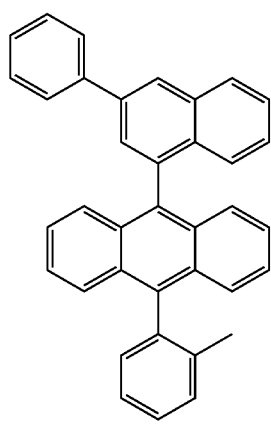
[Cpd. 10]
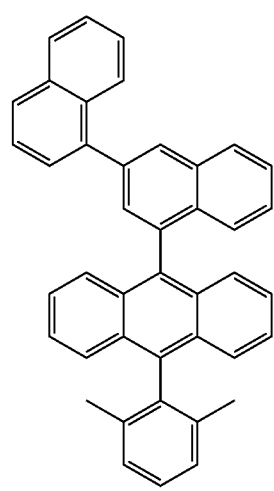
[Cpd. 11]
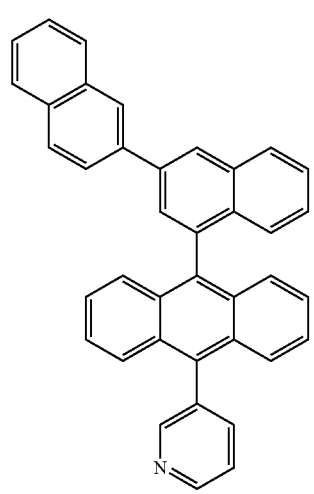
[Cpd. 12]
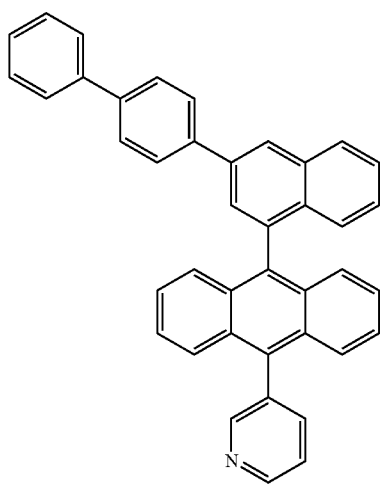
[Cpd. 13]
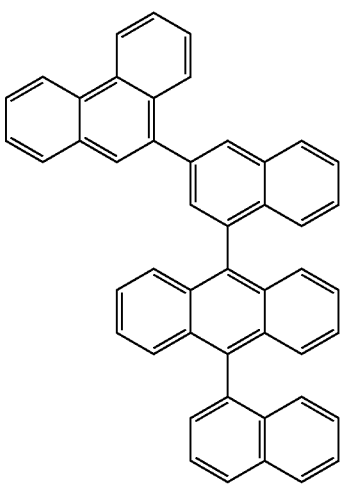
[Cpd. 14]
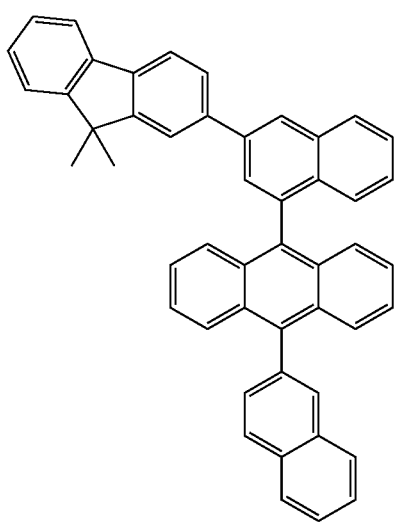

[Cpd. 15]
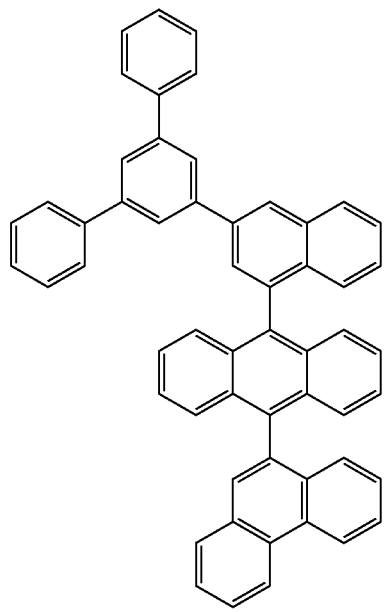
[Cpd. 16]
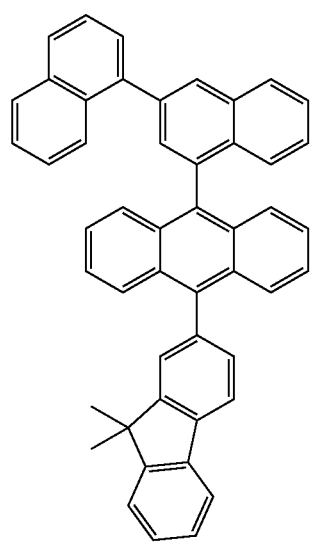
[Cpd. 17]
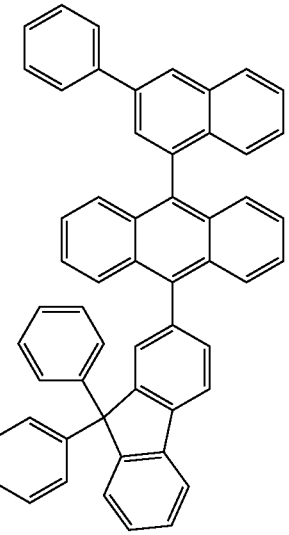
[Cpd. 18]
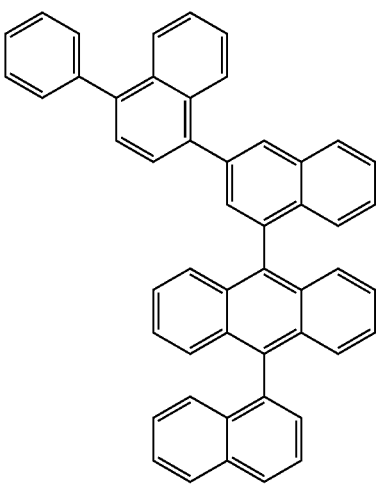
[Cpd. 19]
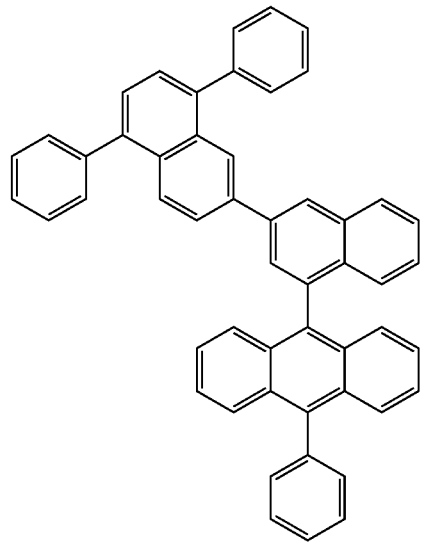

[Cpd. 20]
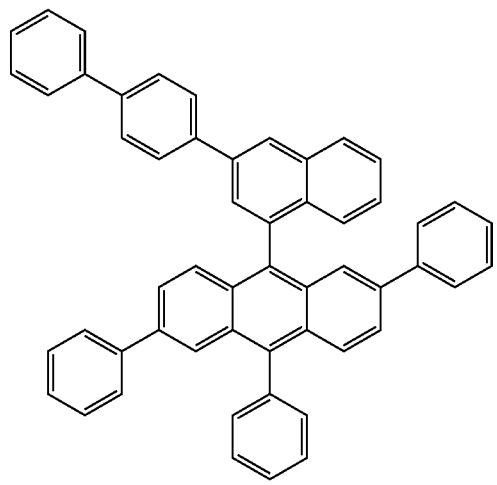
[Cpd. 21]
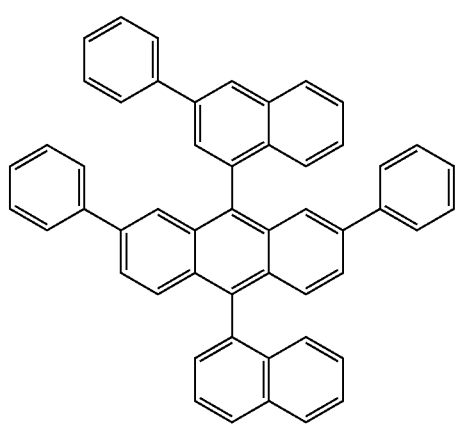
[Cpd. 22]
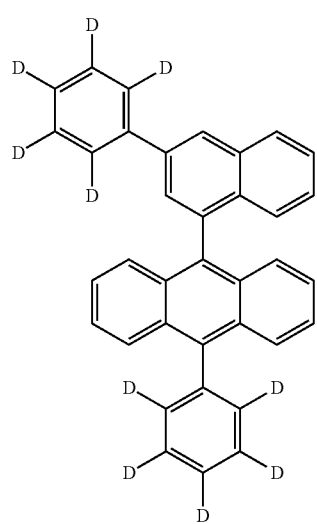
[Cpd. 23]
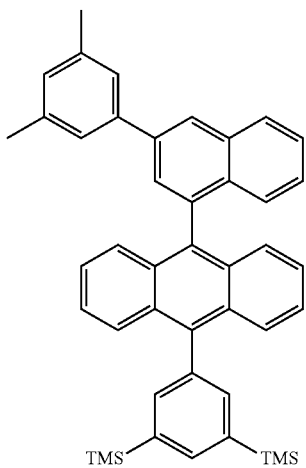
[Cpd. 24]
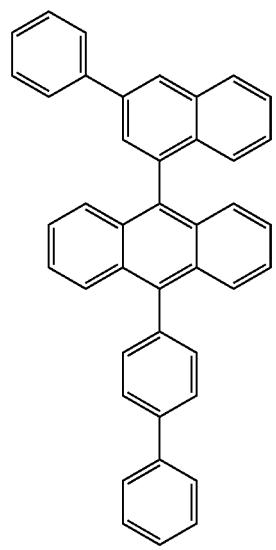
[Cpd. 25]
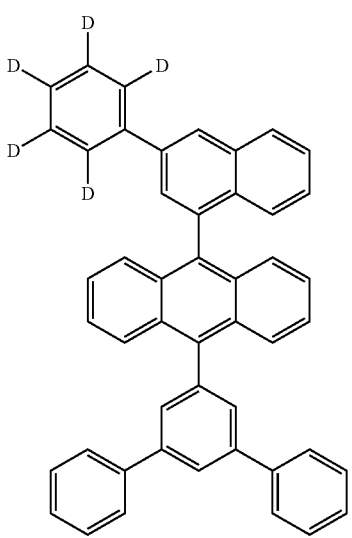

[Cpd. 26]
[Cpd. 27]
[Cpd. 28]
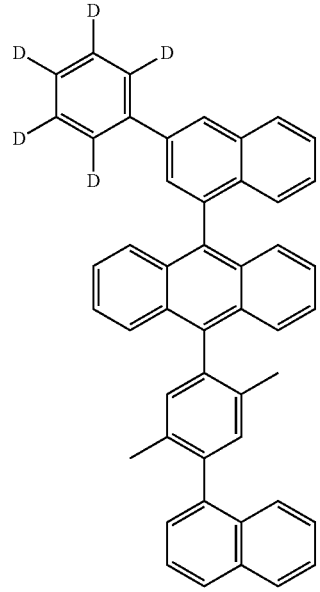
[Cpd. 29]
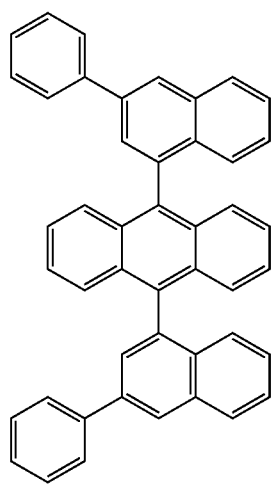
[Cpd. 30]
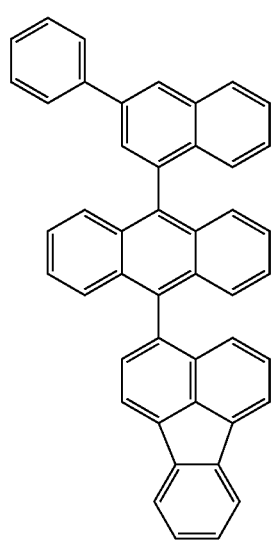

[Cpd. 31]
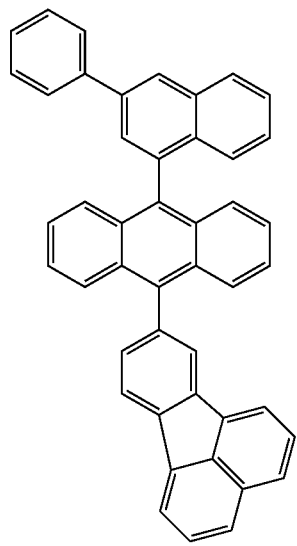
[Cpd. 32]
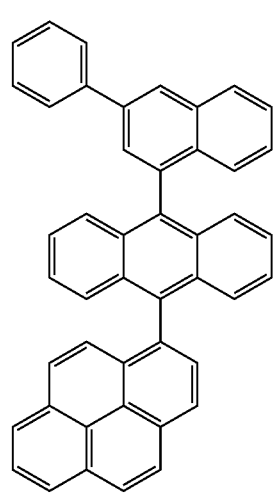
[Cpd. 33]
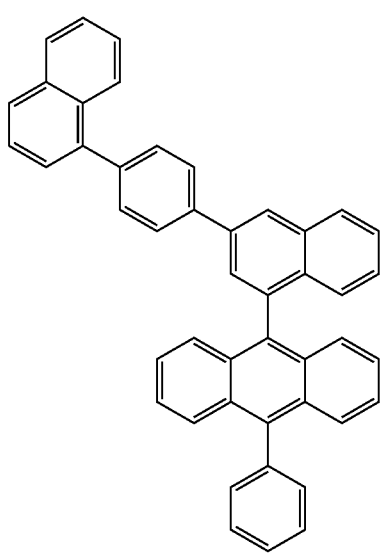
[Cpd. 34]
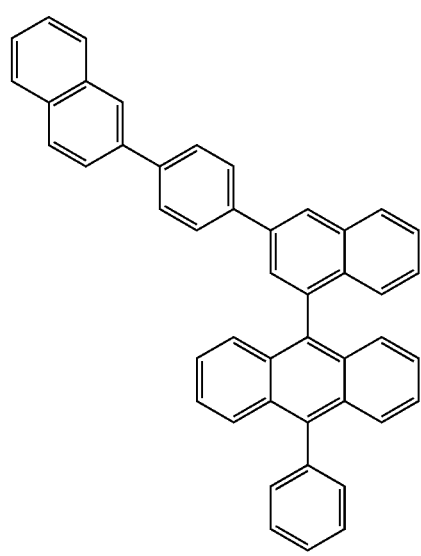
[Cpd. 35]
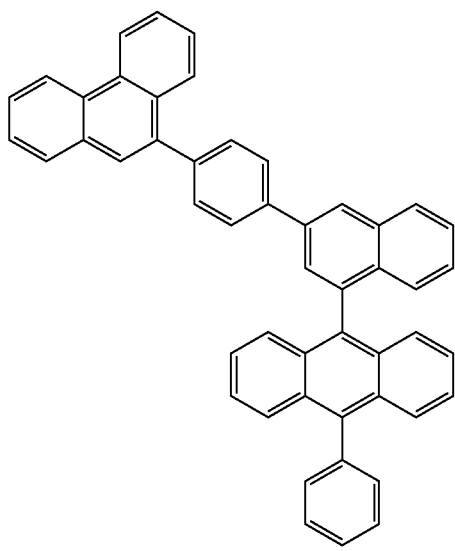
[Cpd. 36]
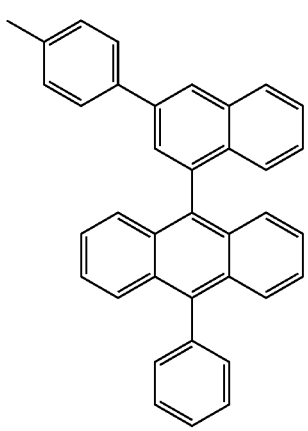

[Cpd. 37]
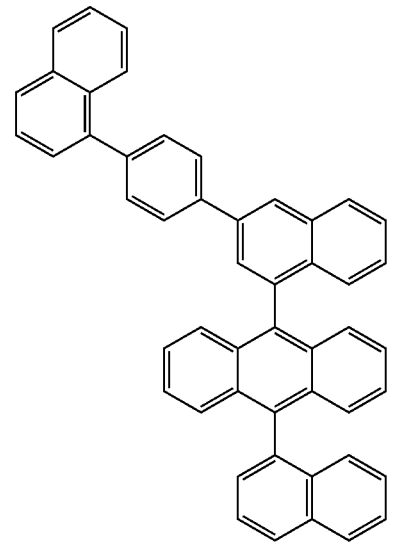
[Cpd. 38]
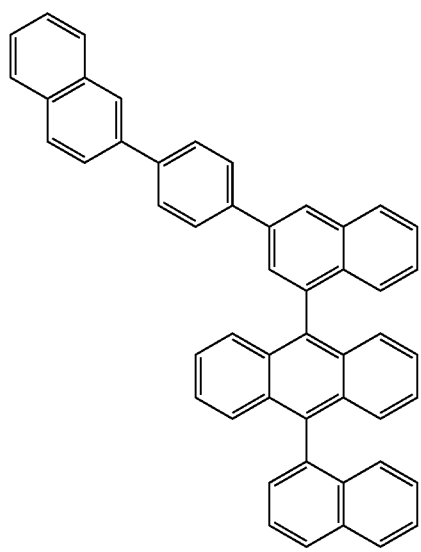
[Cpd. 39]
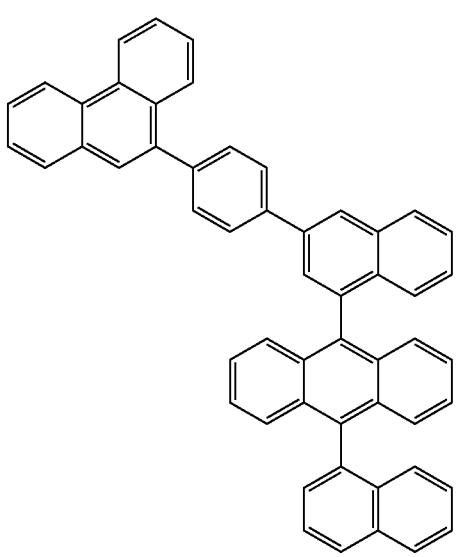
[Cpd. 40]
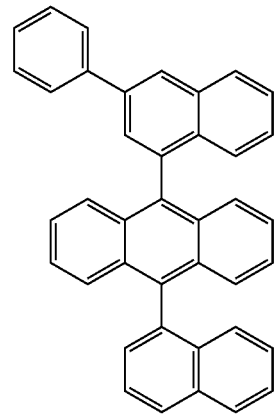
[Cpd. 41]
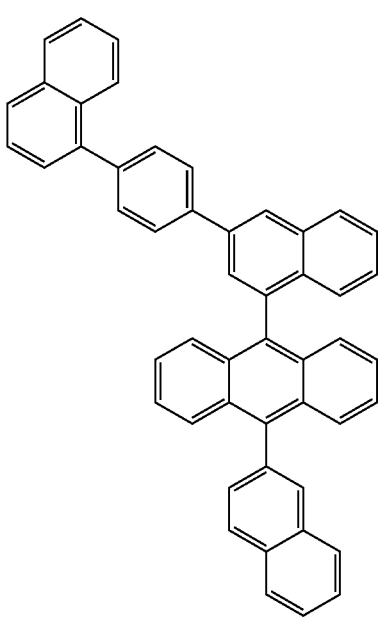
[Cpd. 42]
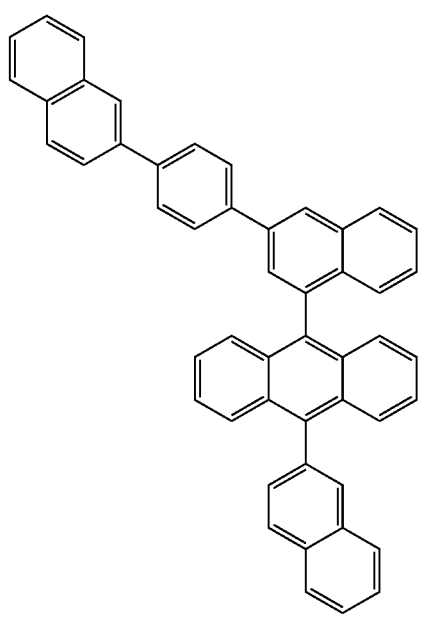

[Cpd. 43]
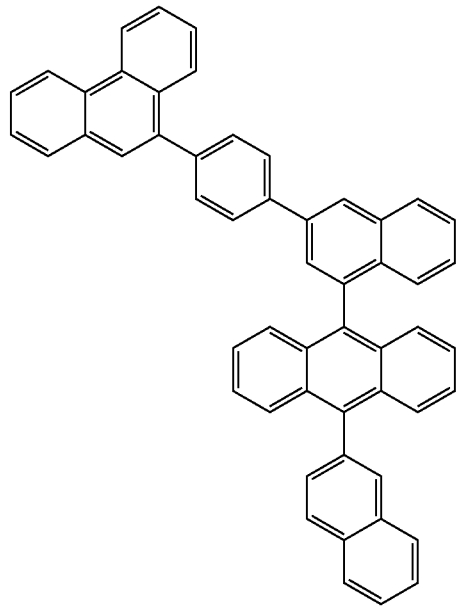
[Cpd. 45]
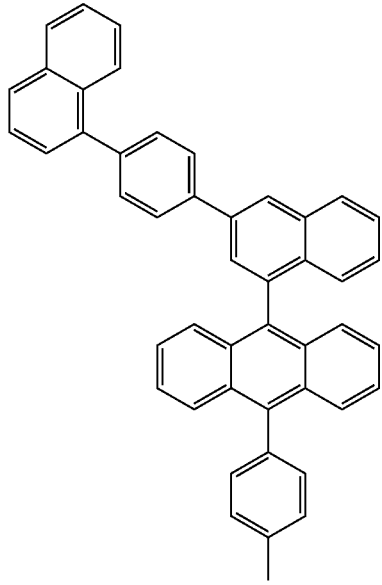
[Cpd. 44]
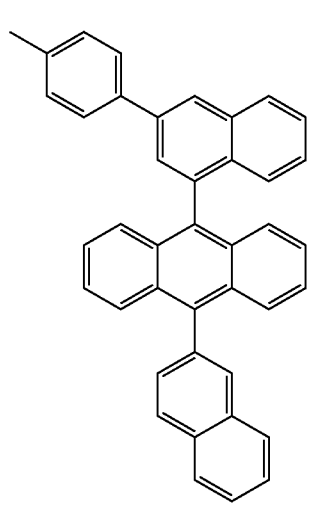
[Cpd. 46]
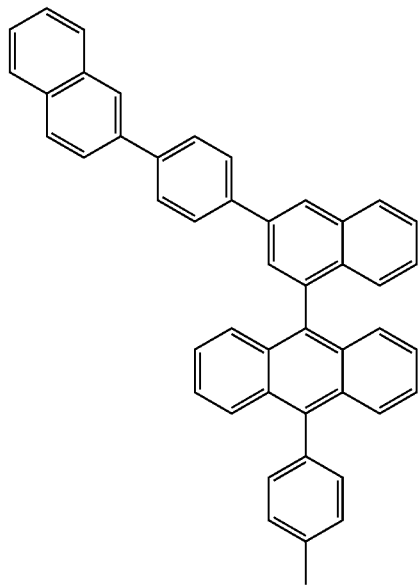

[Cpd. 47]
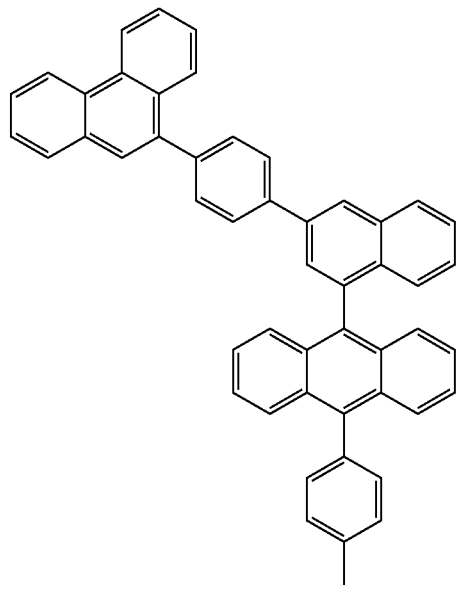
[Cpd. 48]
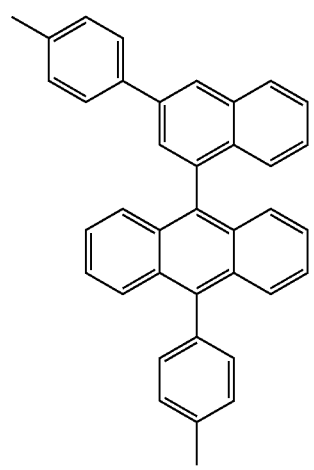
[Cpd. 49]
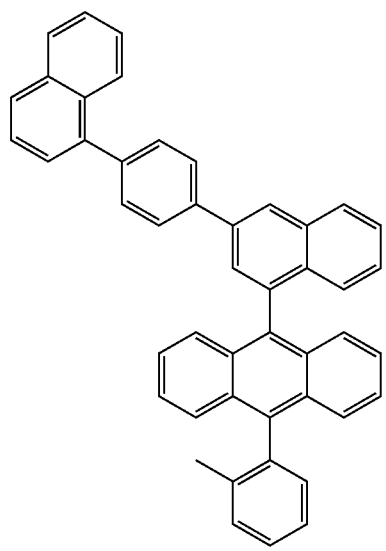
[Cpd. 50]
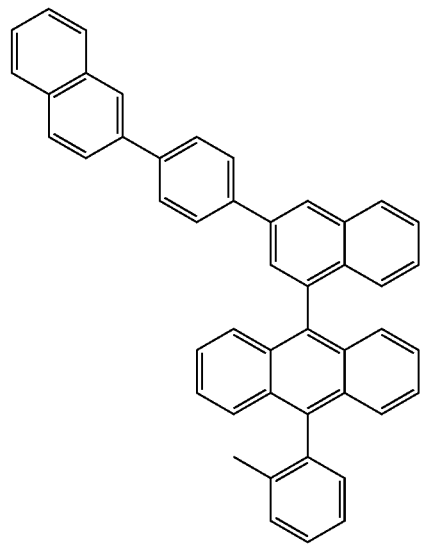
[Cpd. 51]
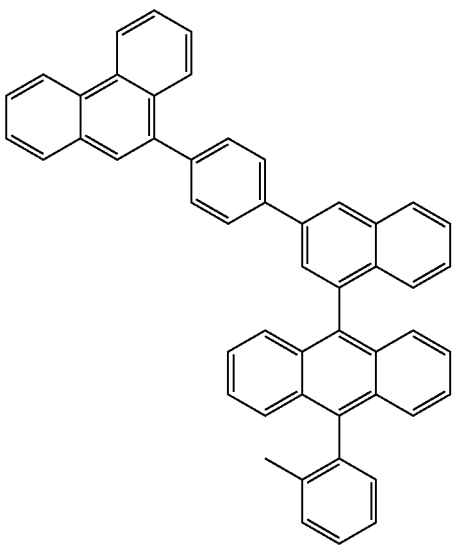
[Cpd. 52]
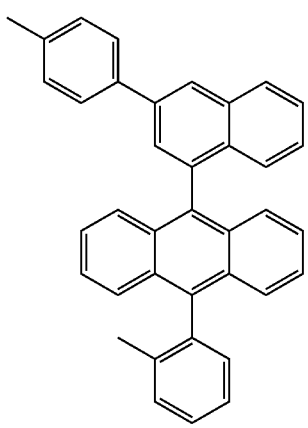

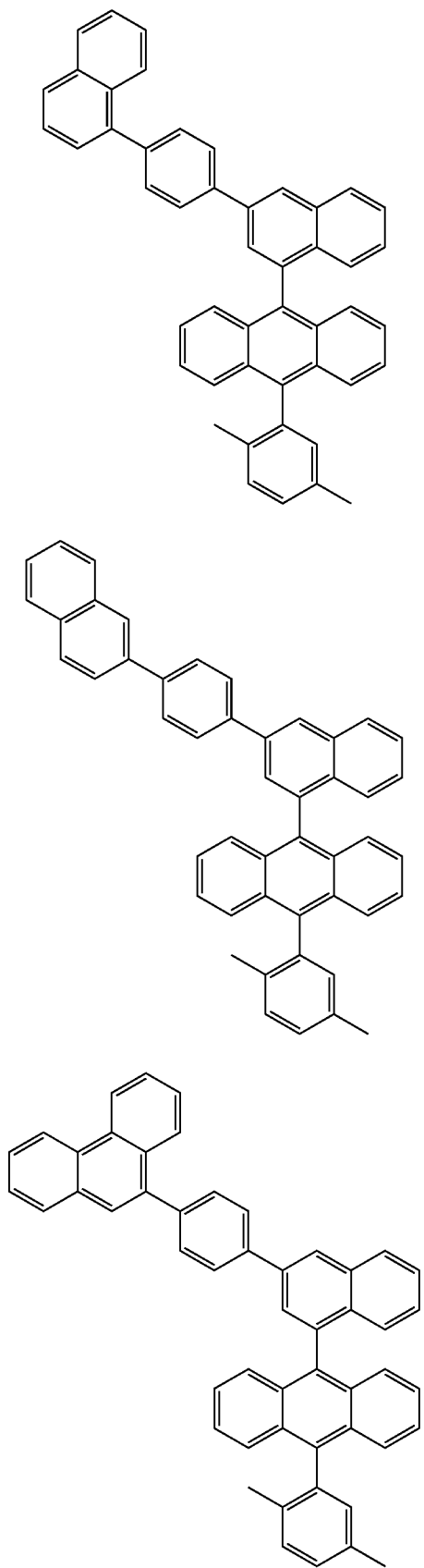
[Cpd. 53]
[Cpd. 54]
[Cpd. 55]
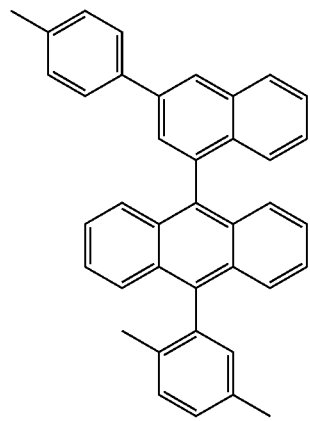
[Cpd. 56]
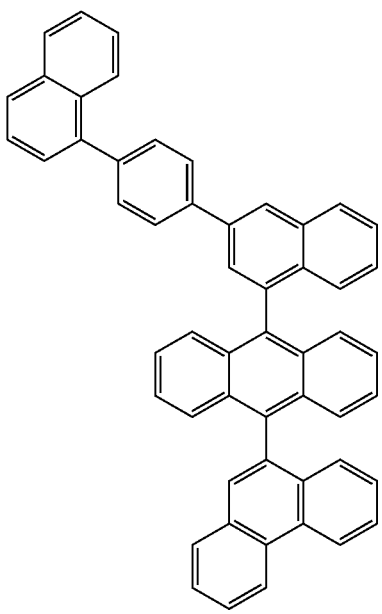
[Cpd. 57]
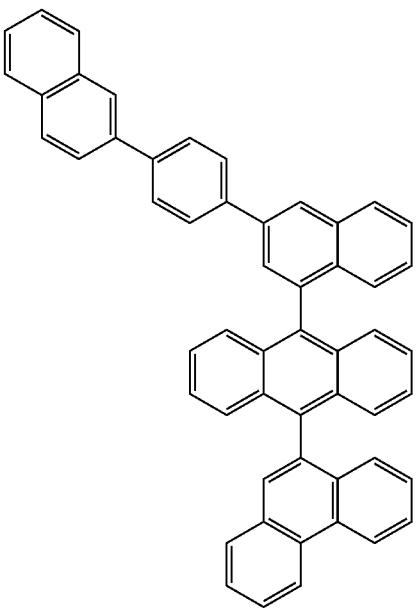
[Cpd. 58]

[Cpd. 59]
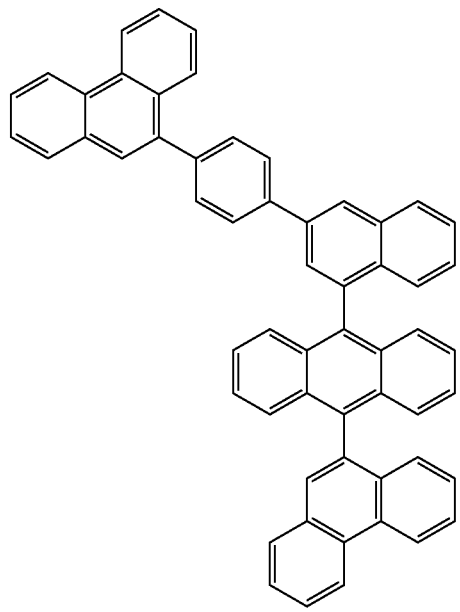
[Cpd. 61]
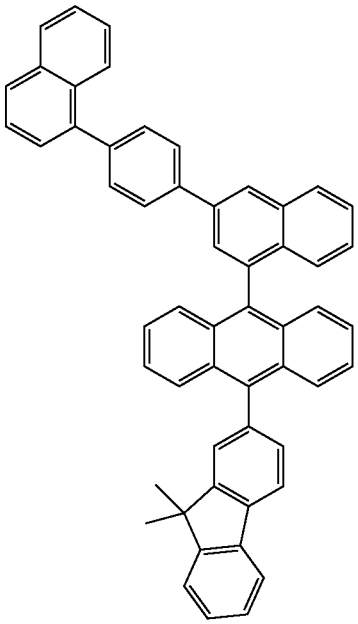
[Cpd. 60]
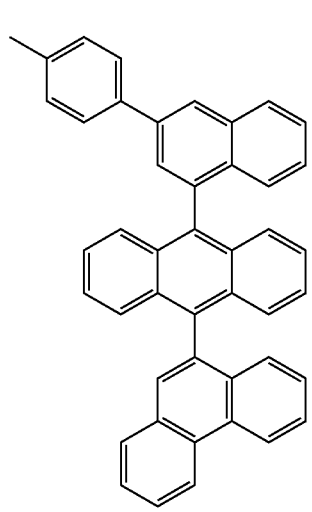
[Cpd. 62]
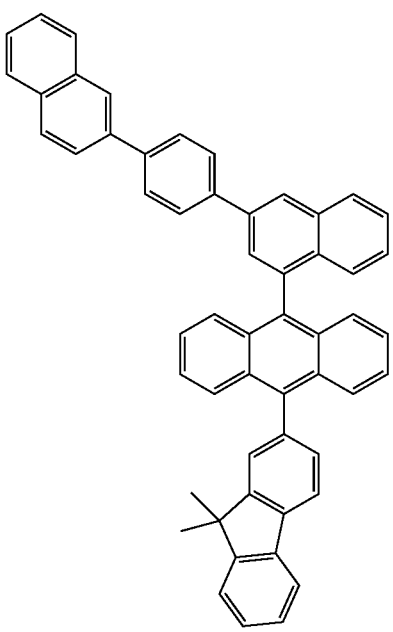

[Cpd. 63]
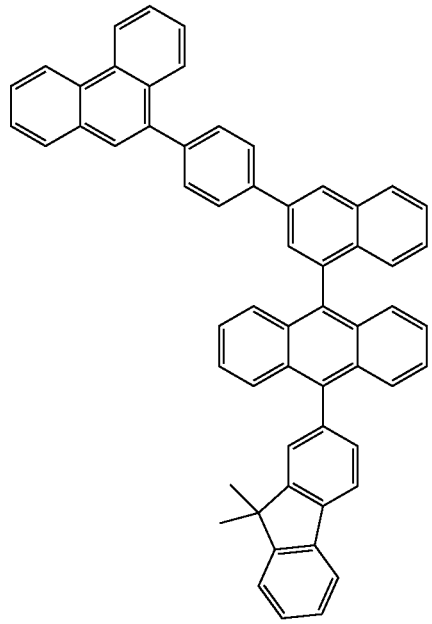
[Cpd. 64]
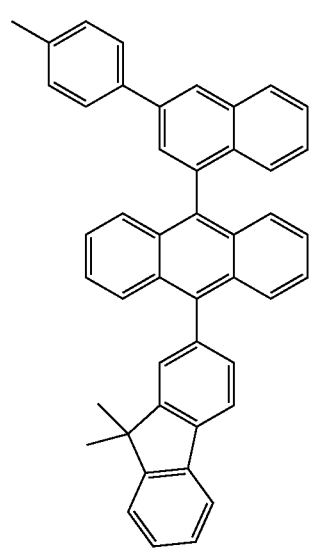
[Cpd. 65]
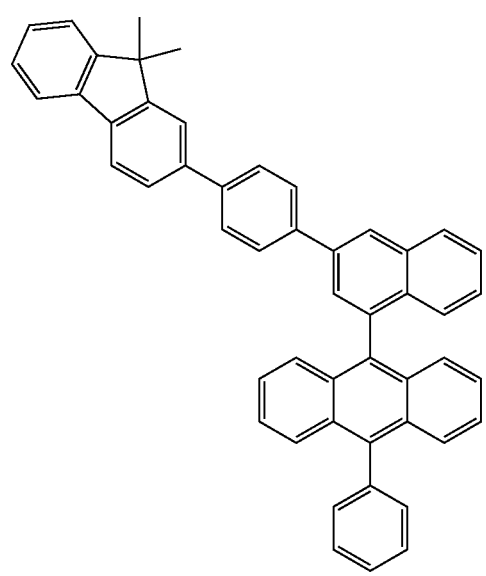
[Cpd. 66]
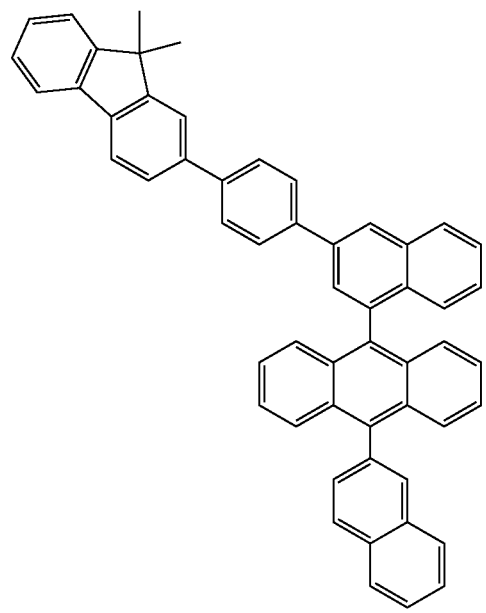

[Cpd. 67]
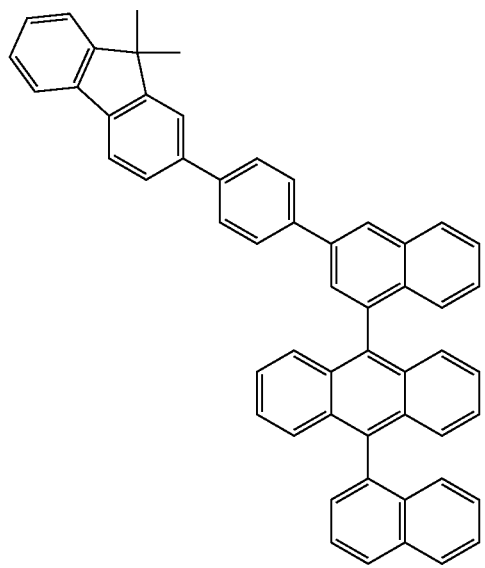
[Cpd. 68]
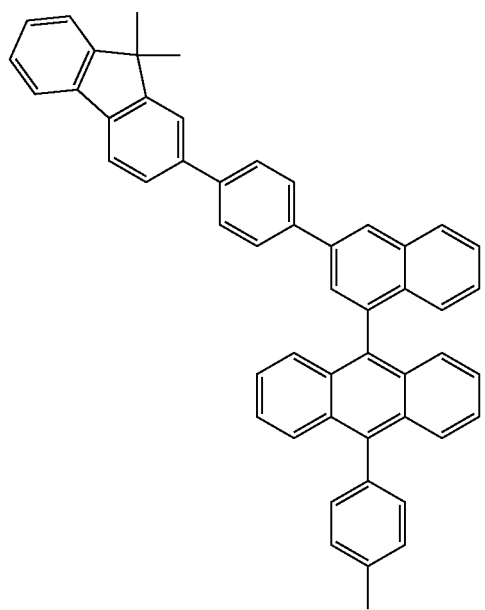
[Cpd. 69]
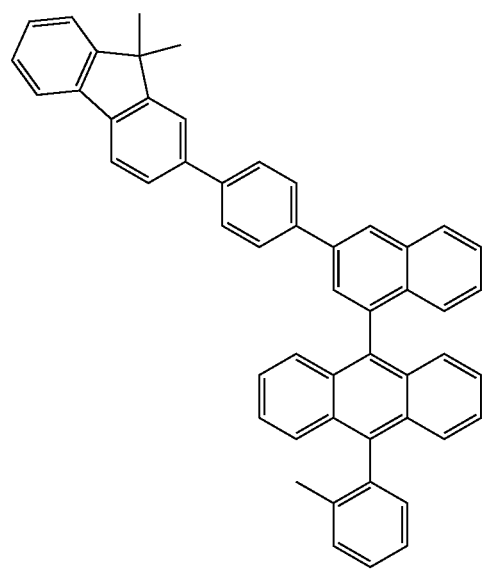
[Cpd. 70]
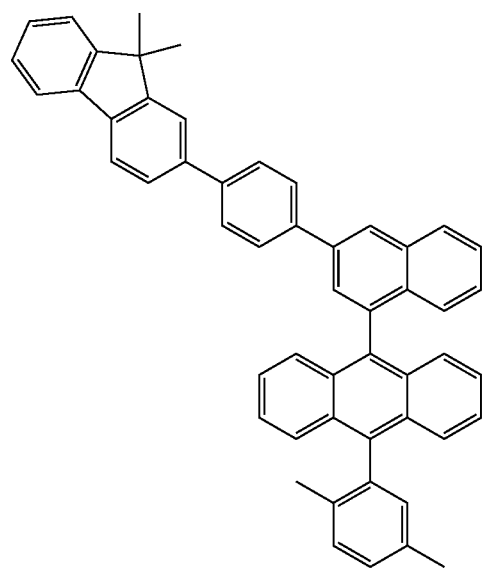

-continued
[Cpd. 71]
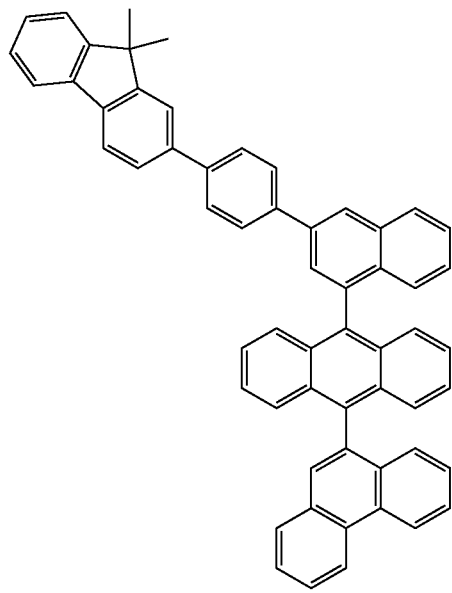
[Cpd. 72]
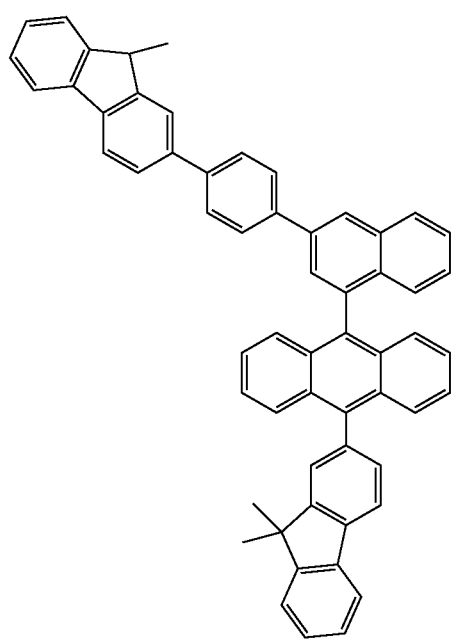
-continued
[Cpd. 73]
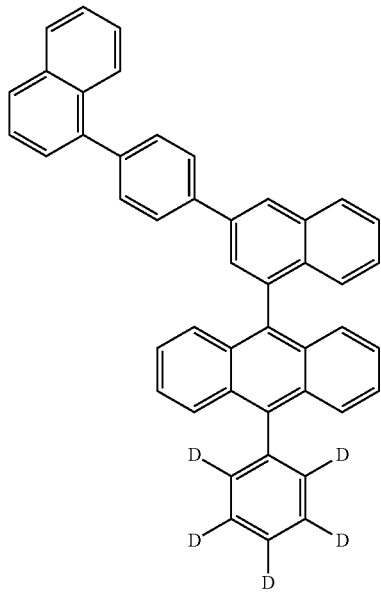
[Cpd. 74]
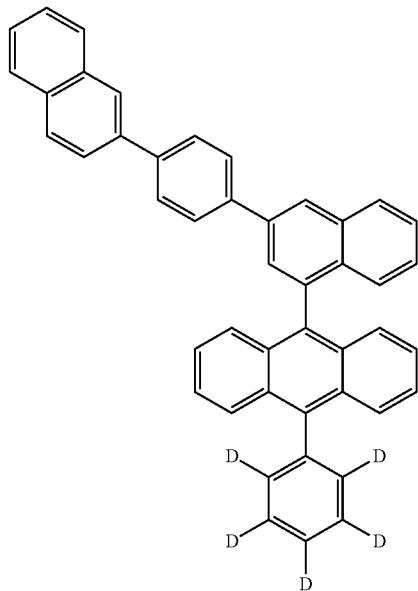

[Cpd. 75]
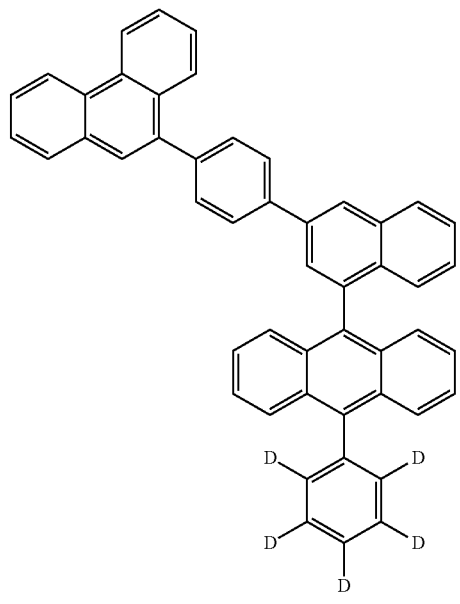
[Cpd. 76]
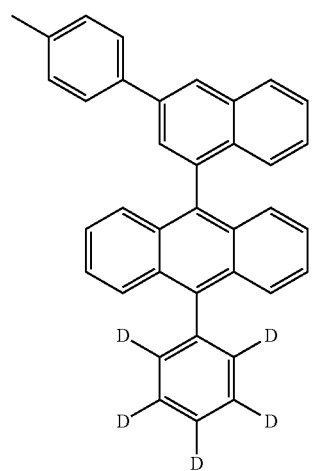
[Cpd. 77]
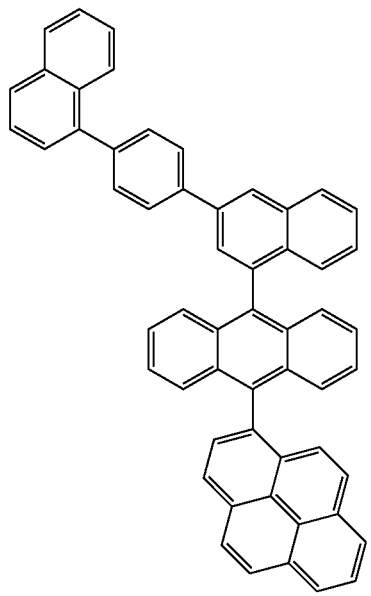
[Cpd. 78]
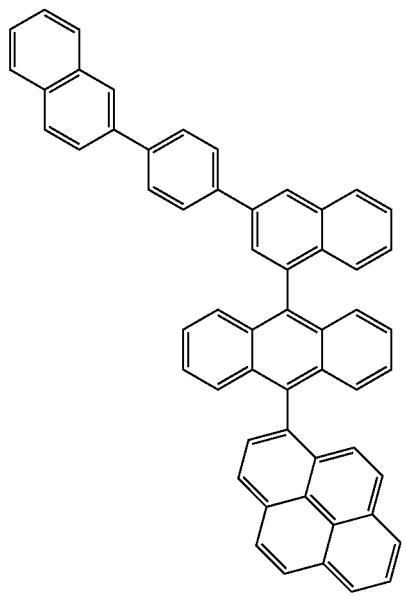
[Cpd. 79]
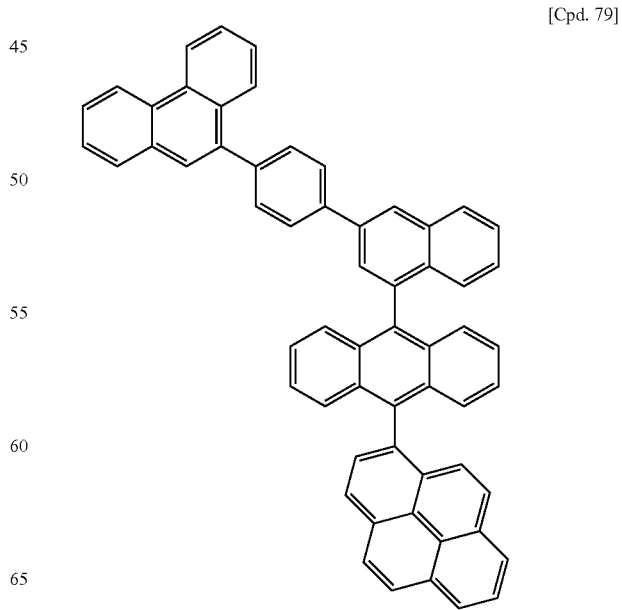

-continued

[Cpd.80]

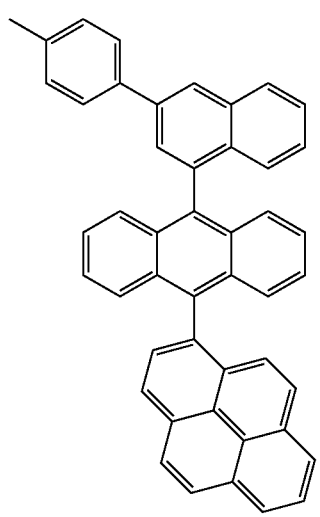

In accordance with a preferred aspect thereof, the present disclosure addresses an organic light-emitting diode, comprising a first electrode; a second electrode facing the first electrode; an organic layer intercalated between the first electrode and the second electrode, wherein the organic layer serves as a light-emitting layer and comprises at least one of the amine compounds represented by Chemical Formula A or B as a dopant, and at least one of the anthracene compounds represented by Chemical Formula C as a host.

As used herein, the expression "(the organic layer) . . . comprising as an organic luminescent compound at least one of amine compounds" is construed to mean that the organic layer may one or two or more different compounds that fall within the scope of the present disclosure.

In some embodiments of the present disclosure, a content of the dopant may range from about 0.01 to 20 parts by weight based on 100 parts by weight of the host, but is not limited thereto.

Also, the light-emitting layer may further comprise various dopant materials in addition to the dopant and the host.

In the light-emitting layer comprising a host and a dopant, when the amine compound represented by Chemical Formula A or B has suitable substituents in combination with a suitable host represented by Chemical Formula C, the light emitted from the light-emitting layer can have a controlled color coordinate CIEy.

On the other hand, the organic light-emitting diode of the present disclosure may comprise two or more light-emitting layers between a cathode and an anode, the light-emitting layers being composed of at least one layer in which a phosphorescent material is employed, and at least one layer in which the compound represented by Chemical Formula A or B is used as a dopant and at least one of the compounds represented by Chemical Formula C is used as a host.

According to some particular embodiments of the present disclosure, the organic light-emitting diode may further comprise at least one of a hole injection layer, a hole transport layer, a functional layer capable of both hole injection and hole transport, an electron transport layer, and an electron injection layer in addition to the light-emitting layer.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum (Alq3), TAZ, Balq, beryllium bis(benzoquinolin-10-olate) (BebQ$_2$), ADN, Compound 201, Compound 202, BCP, and oxadiazole derivatives such as PBD, BMD, BND, etc., but are not limited thereto.

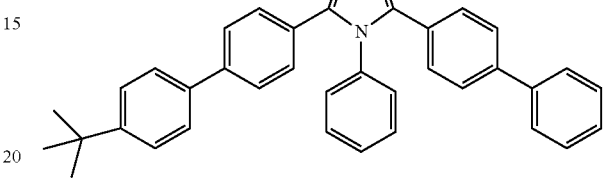

TAZ

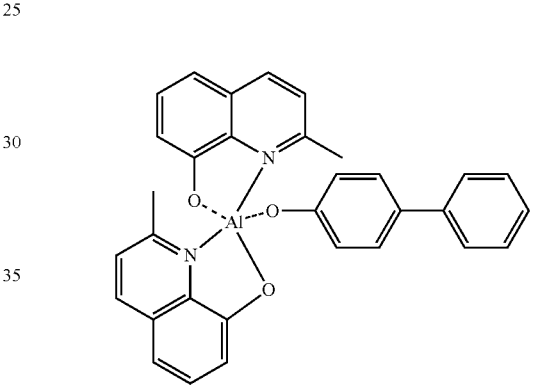

BAlq

<Compound 201>

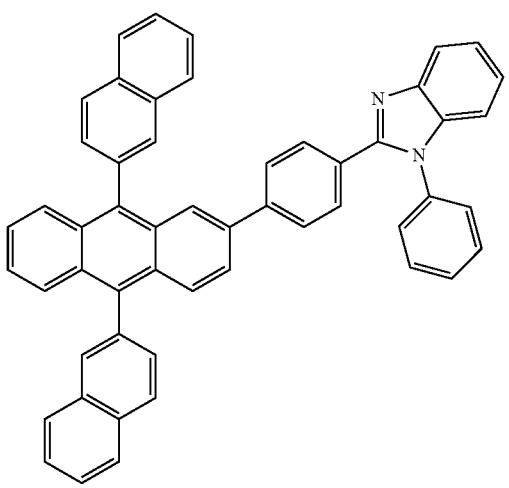

-continued

<Compound 202>

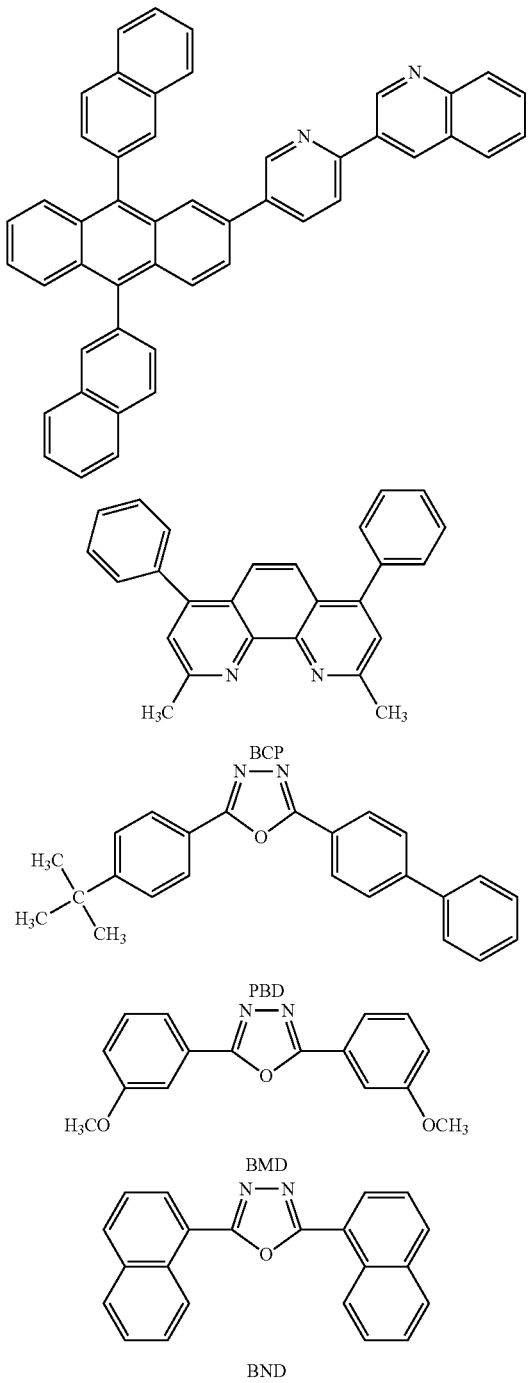

BCP

PBD

BMD

BND

Below, a description will be given of the organic light-emitting diode of the present disclosure, with reference to the FIGURE.

The FIGURE is a schematic cross-sectional view of the structure of an organic light-emitting diode according to some embodiments of the present disclosure. The organic light-emitting diode comprises an anode 20, a hole transport layer 40, an organic light-emitting layer 50, electron transport layer 60, and cathode 80, and optionally a hole injection layer 30 and an electron injection layer 70. In addition, one or two intermediate layers may be further formed in the organic light-emitting diode, or a hole barrier layer or an electron barrier layer may also be employed.

Reference is made to the FIGURE with regard to the fabrication of the organic light-emitting diode of the present disclosure. First, a substrate 10 is coated with an anode electrode material to form an anode 20. So long as it is used in a typical organic EL device, any substrate may be taken as the substrate 10. Preferable is an organic substrate or transparent plastic substrate that exhibits excellent transparency, surface smoothness, and handleability. As the anode electrode material, indium tin oxide (ITO), indium zinc oxide (IZO), tin oxide ($SnO_2$), or zinc oxide (ZnO) may be used.

A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imparted to a hole injection layer material that is typically used in the art. For example, mention may be made of 2-TNATA [4,4',4''-tris(2-naphth-ylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine].

So long as it is typically used in the art, any material for the hole transport layer may be selected without particular limitations. Examples include, but are not limited to, N,N'-bis(3-methylphenyl)-N,N'-diphenyl-[1,1-biphenyl]-4,4'-diamine (TPD) or N,N'-di(naphthalen-1-yl)-N,N'-diphenyl-benzidine (a-NPD).

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the diode becomes poor in efficiency and lifetime. Formed of a material with a low HOMO (Highest Occupied Molecular Orbital) level, the hole barrier layer serves to prevent the introduction of holes into the cathode. Any material that has a higher ionization potential than the light emitting compound, as well as being able to carry electrons may be used for the hole barrier layer without limitations. Representative among the hole barrier materials are BAlq, BCP, and TPBI.

Using a vacuum deposition method or a spin coating method, an electron transport layer 60 may be deposited on the hole barrier layer, and then overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminu-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å.

Further, one or more layers selected from among a hole injection layer, a hole transport layer, a functional layer capable of both hole injection and hole transport, an electron barrier layer, a light-emitting layer, a hole barrier layer, an electron transport layer, and an electron injection layer may be deposited using a single molecule deposition process or a solution process. Here, the deposition process refers to a process by which a material is vaporized in a vacuum or at a low pressure and deposited to form a layer, and the solution process means a method in which a material is dissolved in a solvent and applied for the formation of a thin film by means of inkjet printing, roll-to-roll coating, screen printing, spray coating, dip coating, spin coating, etc.

Also, the organic light-emitting device of the present disclosure may be applied to a device selected from among flat display devices; flexible display devices; monochrome or white flat illumination devices; and monochrome or white flexible illumination devices.

A better understanding of the present disclosure may be obtained through the following examples which are set forth to illustrate, but are not to be construed as the limit of the present disclosure.

EXAMPLES

Preparation of Dopant Compounds

Synthesis Example 1: Synthesis of Compound of Chemical Formula 1

Synthesis Example 1-(1): Synthesis of Intermediate 1-a

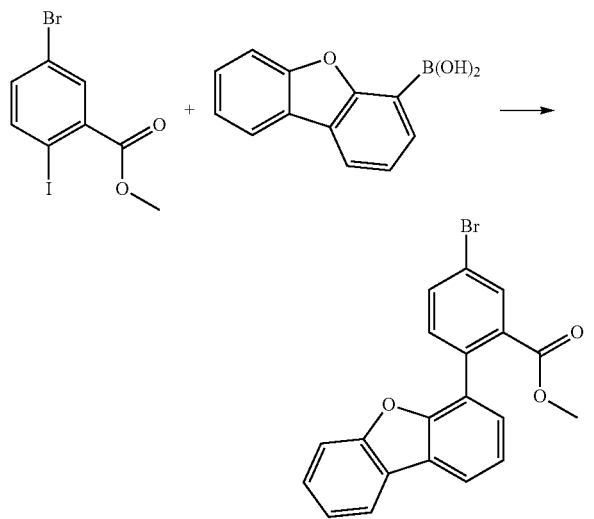

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1%).

Synthesis Example 1-(2): Synthesis of [Intermediate 1-b]

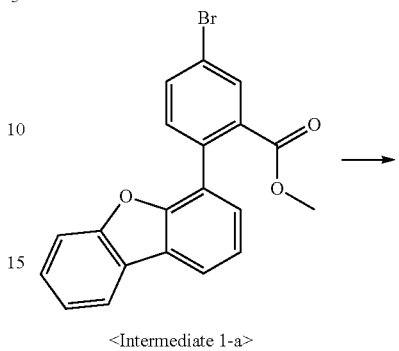

<Intermediate 1-a>

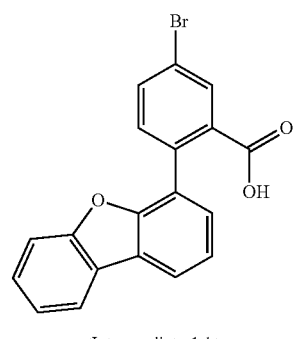

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed by thin layer chromatography, the reaction mixture was cooled to room temperature. The chilled solution was acidified with drops of 2-N HCl, followed by stirring for 30 min. The solid thus formed was filtered, and recrystallized in dichloromethane and n-hexane to afford <Intermediate 1-b>. (14.5 g, 88.6%)

Synthesis Example 1-(3): Synthesis of [Intermediate 1-c]

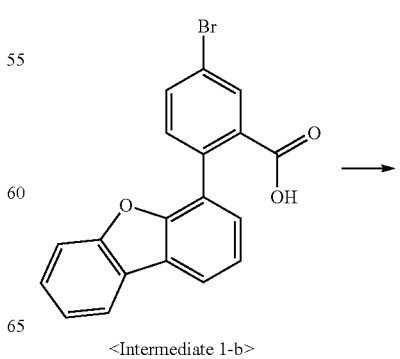

<Intermediate 1-b>

-continued

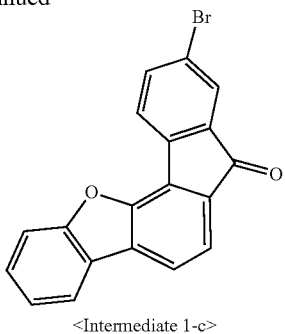
<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed by thin layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4): Synthesis of [Intermediate 1-d]

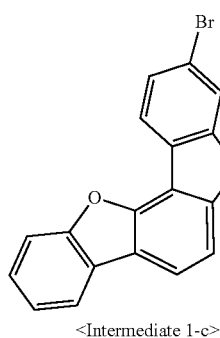
<Intermediate 1-c>

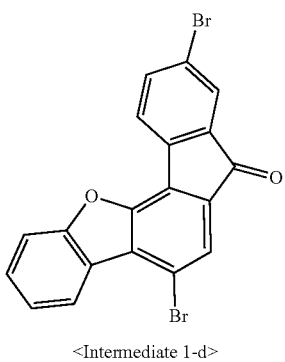
<Intermediate 1-d>

In a 1-L round-bottom flask reactor, <Intermediate 1-c> (11.5 g, 33 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered, and washed with acetone. Recrystallization in monochlorobenzene afforded <Intermediate 1-d>. (11.0 g, 78%)

Synthesis Example 1-(5): Synthesis of [Intermediate 1-e]

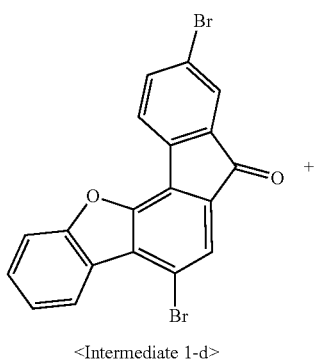
<Intermediate 1-d>

+

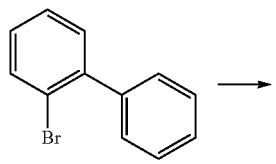

→

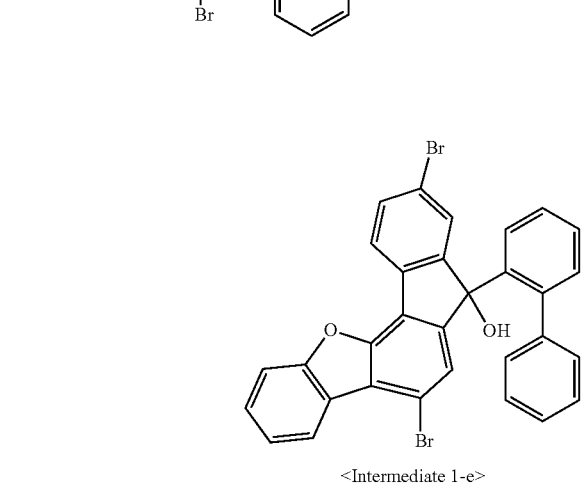
<Intermediate 1-e>

In a 250-ml round-bottom flask reactor, 2-bromobiphenyl (8.4 g, 0.036 mol) and tetrahydrofuran (110 ml) were frozen at −78° C. under a nitrogen atmosphere. At the same temperature, n-butyl lithium (19.3 ml, 0.031 mol) was dropwise added to the reaction solution which was then stirred for 2 hrs. Thereafter, <Intermediate 1-d> (11.0 g, 0.026 mol) was added little by little to the reaction solution, and stirred at room temperature. When the reaction mixture started to change color, the reaction was monitored via thin layer chromatography. After the reaction was stopped with $H_2O$ (50 ml), extraction was conducted with ethylacetate and water. The organic layer was separated, concentrated in a vacuum, and recrystallized in acetonitrile to afford <Intermediate 1-e> as a solid. (12.2 g, 81.5%)

Synthesis Example 1-(6): Synthesis of [Intermediate 1-f]

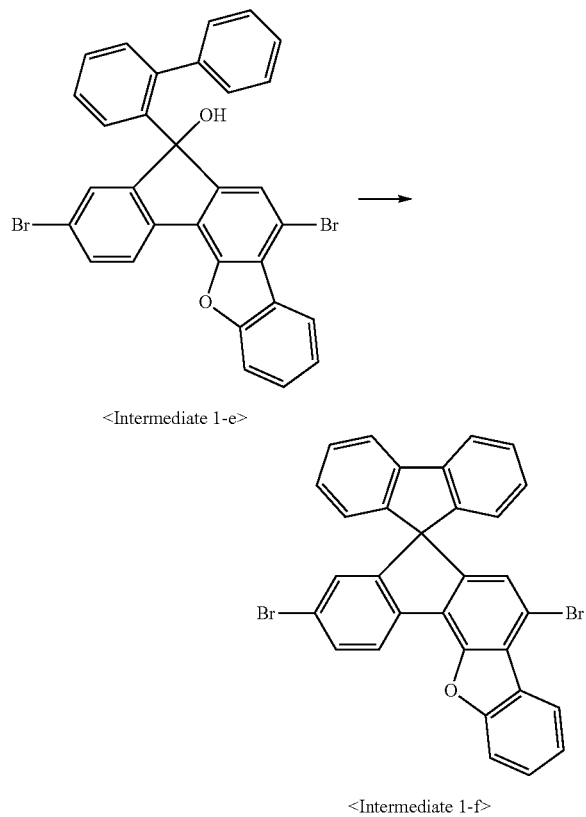

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin layer chromatography. The reaction mixture was then cooled to room temperature and filtered. The filtrate was washed with $H_2O$ and methanol and dissolved in monochlorobenzene. Following silica gel chromatography, the fraction was concentrated and cooled to room temperature to give <Intermediate 1-f>. (10.7 g, 90%>

Synthesis Example 1-(7): Synthesis of Compound of Chemical Formula 1

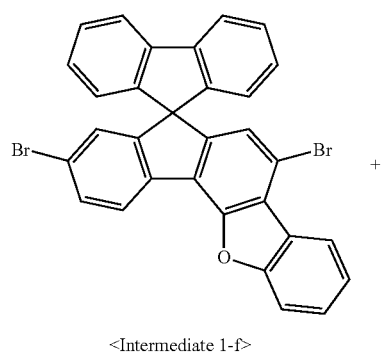

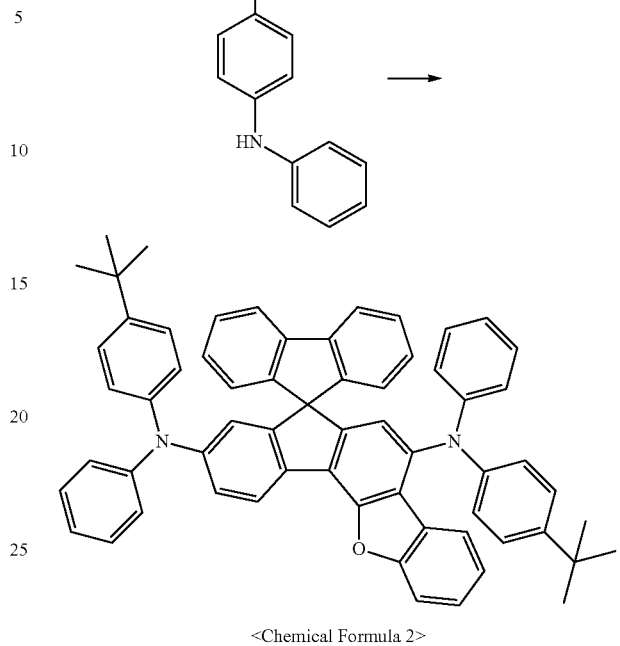

In a 250-ml round-bottom flask reactor, a mixture of <Intermediate 1-f> (5.0 g, 0.009 mol), (4-tert-butylphenyl)-phenylamine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) were stirred together for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 1 as a solid (2.9 g, 38%).

MS (MALDI-TOF): m/z 852.41 [M+]

Synthesis Example: Synthesis of Compound of Chemical Formula 231

Synthesis Example 2-(1): Synthesis of Intermediate 2-a

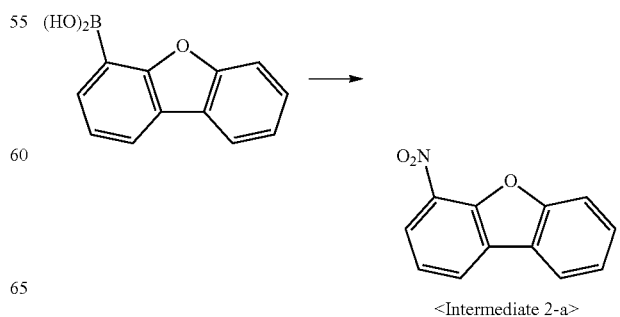

In a 1-L round-bottom flask reactor, dibenzofuran-4-bronic acid (85.0 g, 0.401 mol), bismuth (III) nitrate pentahydrate (99.2 g, 0.200 mol), and toluene (400 ml) were reacted at 70° C. for 3 hrs under a nitrogen atmosphere while stirring. After completion of the reaction, the reaction mixture was cooled to room temperature and washed with toluene. Filtration afforded <Intermediate 2-a> as a solid (61.5 g, 72%).

Synthesis Example 2-(2): Synthesis of Intermediate 2-b

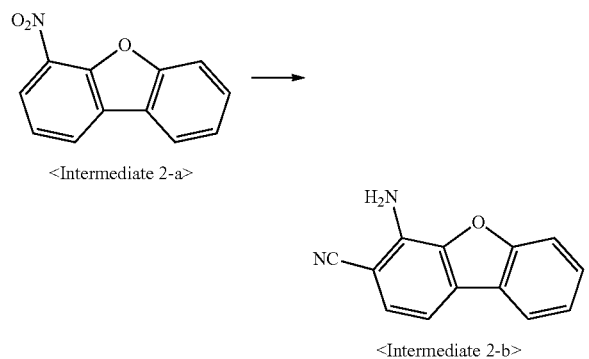

<Intermediate 2-a>

<Intermediate 2-b>

In a 2-L round-bottom flask reactor, ethylcyanoacetate (202.9 g, 1.794 mol), and dimethylformamide (500 ml) were added with potassium hydroxide (67.10 g, 1.196 mol), potassium cyanide (38.95 g, 0.598 mol), and dimethylformamide (200 ml), followed by stirring at room temperature. To this reaction solution, <Intermediate 2-a> (127.5 g, 0.737 mol) was slowly added while stirring at 50° C. for 72 hrs. After completion of the reaction, an aqueous sodium hydroxide solution (25%, 200 ml) was added, and stirred for 3 hrs under reflux. Subsequently, the reaction mixture was cooled to room temperature, followed by extraction with ether acetate and water. The organic layer was separated and concentrated. Purification by column chromatography afforded <Intermediate 2-b> (20.0 g, 16%).

Synthesis Example 2-(3): Synthesis of Intermediate 2-c

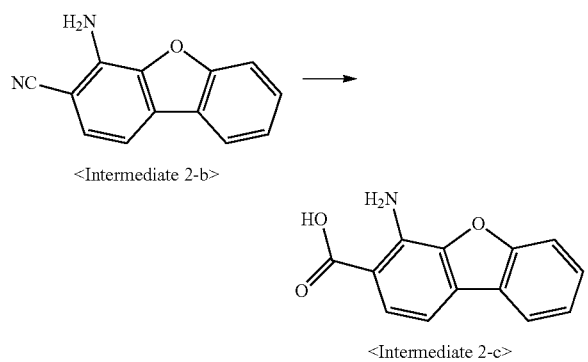

<Intermediate 2-b>

<Intermediate 2-c>

In a 2-L round-bottom flask reactor, <Intermediate 2-b> (20.0 g, 0.096 mol), ethanol (600 ml), and an aqueous solution (170 ml) of potassium hydroxide solution (142.26 g, 2.53 mol) were stirred for 12 hrs under reflux. After completion of the reaction, the reaction mixture was cooled to room temperature, and acidified with 6 N HCl (400 ml). Then, the reaction mixture was stirred for 20 min, and filtered. The filtrate was washed with ethanol to afford <Intermediate 2-c> as a solid (17.0 g, 88.5%).

Synthesis Example 2-(4): Synthesis of Intermediate 2-d

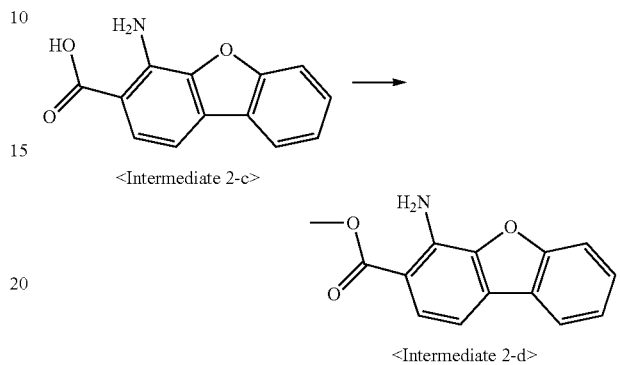

<Intermediate 2-c>

<Intermediate 2-d>

In a 2-L round-bottom flask reactor, <Intermediate 2-c> (17.0 g, 0.075 mol) and sulfuric acid (15 ml) were stirring together for 72 hrs under reflux. After completion of the reaction, the reaction mixture was cooled to room temperature and extracted with ethylacetate and water. The organic layer was separated, and washed with an aqueous sodium hydrogen carbonate solution. An excess of methanol was added during vacuum concentration, followed by filtration to afford <Intermediate 2-d> as a solid (14.0 g, 77.6%).

Synthesis Example 2-(5): Synthesis of Intermediate 2-e

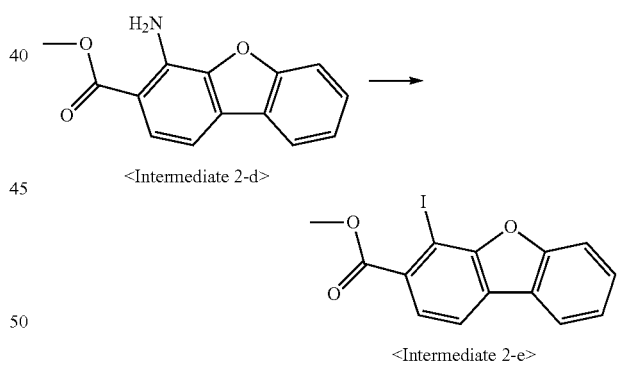

<Intermediate 2-d>

<Intermediate 2-e>

In a 500-mL round-bottom flask reaction, <Intermediate 2-d> (14.0 g, 0.058 mol), HCl (20 ml), and water (100 ml) were stirred together for 1 hr at 0° C. At the same temperature, an aqueous solution (50 ml) of sodium nitrite (7.4 g, 0.116 mol) was dropwise added to the reaction mixture and then stirred for 1 hr. An aqueous solution (100 ml) of potassium iodide (30.0 g, 0.180 mol) was dropwise added with care not to increase the temperature of the reaction solution above 5° C. Stirring was continued for 5 hrs at room temperature, and after completion of the reaction, the reaction mixture was washed with an aqueous sodium thiosulfate solution, and extracted with ethylacetate and water. The organic layer was separated and concentrated in a vacuum. Purification through column chromatography gave <Intermediate 2-e> (9.1 g, 48%).

Synthesis Example 2-(6): Synthesis of Intermediate 2-f

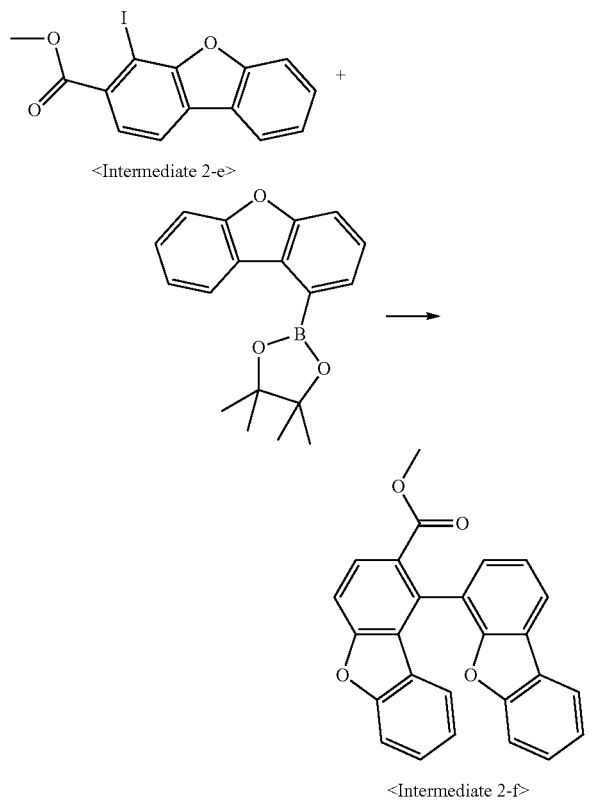 [SMILES: COC(=O)c1ccc2c(oc3ccccc32)c1I ; CC1(C)OB(c2cccc3oc4ccccc4c23)OC1(C)C ; COC(=O)c1ccc2oc3ccccc3c2c1-c1cccc2c1oc1ccccc12]

<Intermediate 2-e>

<Intermediate 2-f>

In a 250-mL round-bottom flask reactor, <Intermediate 2-e> (9.3 g, 25 mmol), 4-dibenzofuranborate (8.3 g, 28 mmol), tetrakis(triphenylphosphine)palladium (0.6 g, 0.05 mmol), and potassium carbonate (6.7 g, 50 mmol) were placed, and then toluene (50 mL), tetrahydrofuran (50 mL), and water (20 mL) were added. The temperature of the reactor was elevated to 80° C. before stirring for 10 hrs. After completion of the reaction, the temperature was cooled to room temperature, and extraction was conducted with ethylacetate. The organic layer thus formed was concentrated in a vacuum and purified by column chromatography to afford <Intermediate 2-f> (5.3 g, 52.3%).

Synthesis Example 2-(7): Synthesis of Intermediate 2-g

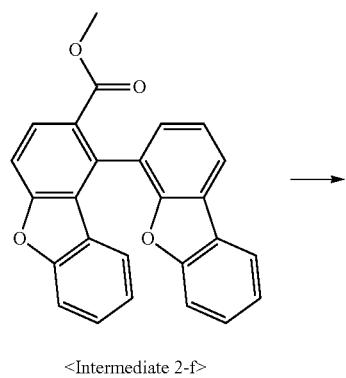

<Intermediate 2-f>

<Intermediate 2-g> in a 500-ml round-bottom flask reactor, bromobenzene (25.5 g, 0.163 mol) and tetrahydrofuran (170 ml) were cooled to −78° C. in a nitrogen atmosphere. N-butyl lithium (95.6 ml, 0.153 mol) was dropwise added to the chilled solution, and stirred for 1 hr at the same temperature. Then, <Intermediate 4-f> (20.0 g, 0.051 mol) was added at room temperature while stirring. After completion of the reaction, the reaction was stopped with $H_2O$ (50 ml), and extraction with ethyl acetate and water was conducted. The concentrate was mixed with acetic acid (200 ml) and HCl (1 ml) by stirring at 80° C. After completion of the reaction, the reaction mixture was cooled to room temperature, and the precipitate thus formed was filtered, and washed with methanol to afford <Intermediate 2-g> (20.0 g, 78%).

Synthesis Example 2-(8): Synthesis of Intermediate 2-h

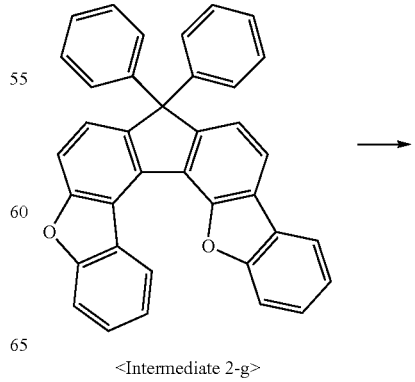

<Intermediate 2-g>

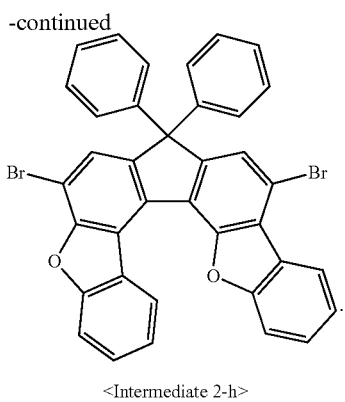

<Intermediate 2-h>

In a 100-mL round-bottom flask reactor, <Intermediate 2-g> (20 g, 58 mmol) and dichloromethane (40 ml) were stirred together at room temperature. A dilution of bromine (5.8 ml, 116 mmol) in dichloromethane (10 ml) was dropwise added, followed by stirring at room temperature for 8 hrs. After completion of the reaction, the reaction mixture was stirred together with acetone (20 ml). The solid thus formed was filtered, and washed with acetone. Recrystallization in monochlorobenzene afforded <Intermediate 2-h> (15.8 g, 55%)

Synthesis Example 2-(9): Synthesis of Compound of Chemical 231

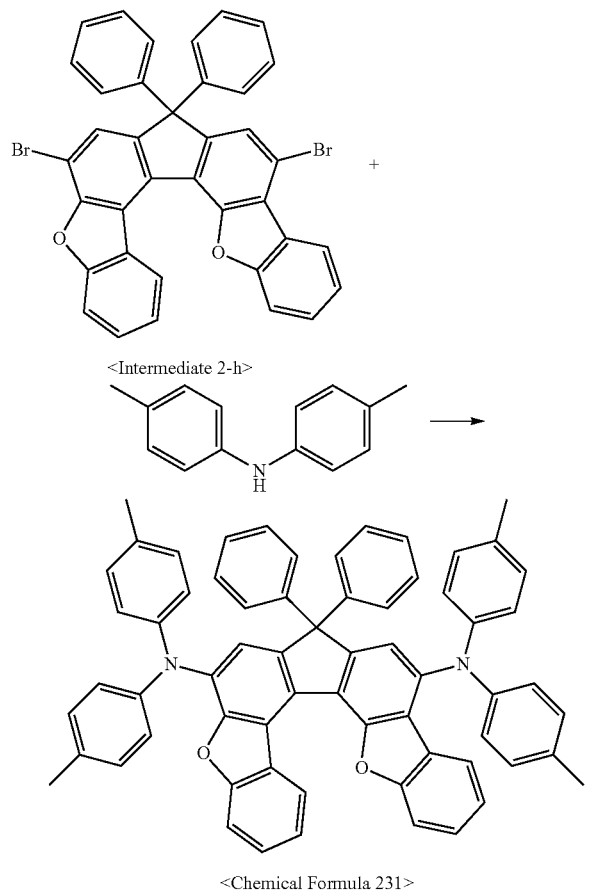

<Chemical Formula 231>

In a 100-ml round-bottom flask reactor, a mixture of <Intermediate 2-h> (4.0 g, 0.006 mol), di-p-tollylamine (3.2 g, 0.016 mol), palladium (II) acetate (0.08 g, 0.4 mmol), sodium tert-butoxide (3.2 g, 0.032 mol), tri-tert-butyl phosphine (0.08 g, 0.4 mmol), and toluene (50 ml) were stirred together for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield <Chemical Formula 231> as a solid (2.1 g, 41%).

MS (MALDI-TOF): m/z 890.0 [M$^+$]

Synthesis Example 3: Synthesis of Compound of Chemical Formula 98

Synthesis Example 3-(1): Synthesis of Intermediate 3-a

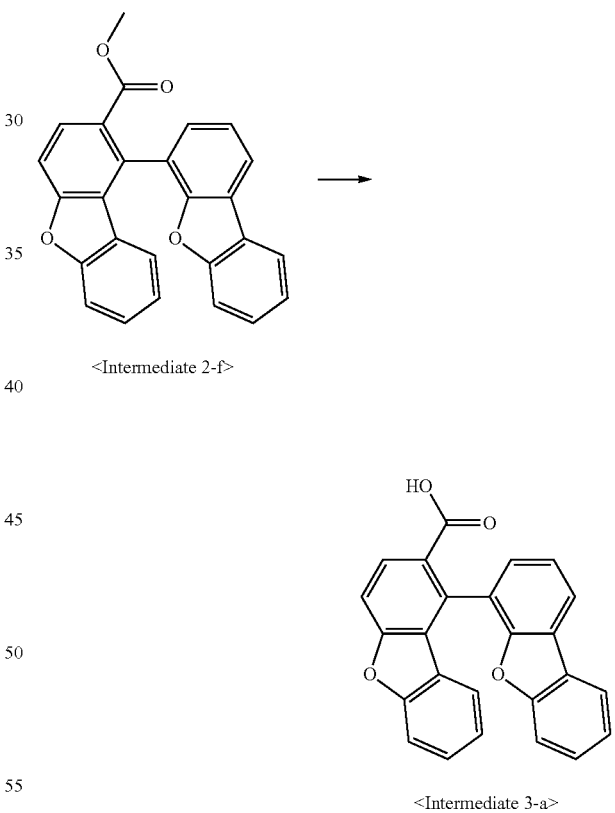

<Intermediate 3-a>

In a 100-mL round-bottom flask reactor, <Intermediate 2-f> (5.3 g, 15 mmol), sodium hydroxide (0.7 g, 17 mmol), and ethanol (50 ml) were stirred for 48 under reflux. After completion of the reaction was confirmed by thin layer chromatography, the reaction mixture was cooled to room temperature. To the cooled solution, drops of 2-N HCl were added over 30 min while stirring. Recrystallization in dichloromethane and normal hexane afforded <Intermediate 3-a> as a solid (4.5 g, 88.0%).

Synthesis Example 3-(2): Synthesis of Intermediate 3-b

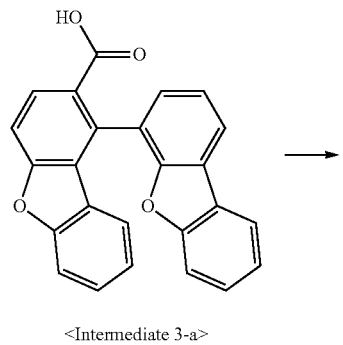

<Intermediate 3-a>

In a 100-ml round-bottom flask reactor, <Intermediate 3-a> (4.5 g, 12 mmol) was reacted with methane sulfonic acid (30 ml) at 80° C. for 3 hrs while stirring. After completion of the reaction was confirmed by thin layer chromatography, drops of the reaction mixture were slowly added to ice water (50 ml), and then stirred for 30 min. Filtration and washing with water and methanol gave <Intermediate 3-b> as a solid (3.8 g, 88.8%).

Synthesis Example 3-(3): Synthesis of Intermediate 3-c

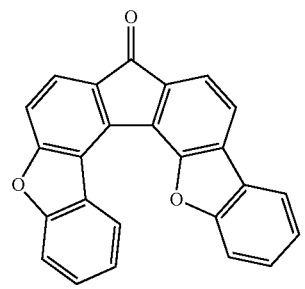

<Intermediate 3-b>

In a 100-mL round-bottom flask reactor, <Intermediate 3-b> (3.8 g, 11 mmol) was stirred together with dichloromethane (40 ml) at room temperature, and then a dilution of bromine (1.1 ml, 22 mmol) in dichloromethane (10 ml) was dropwise added, followed by stirring at room temperature for 8 hrs. After completion of the reaction, acetone (20 ml) was added to the reactor and stirred. The precipitate thus formed was filtered, and washed with acetone. Recrystallization in monochlorobenzene gave <Intermediate 3-c> as a solid (3.0 g, 55%).

Synthesis Example 3-(4): Synthesis of Intermediate 3-d

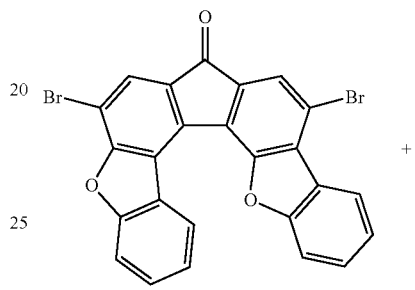

<Intermediate 3-c>

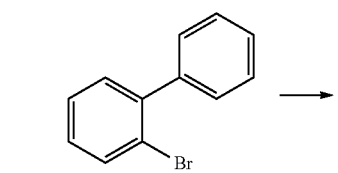

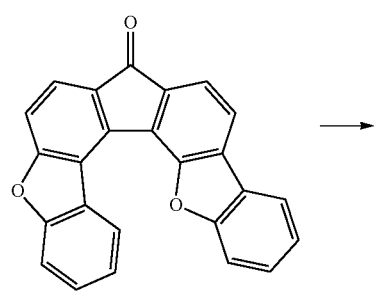

<Intermediate 3-c>

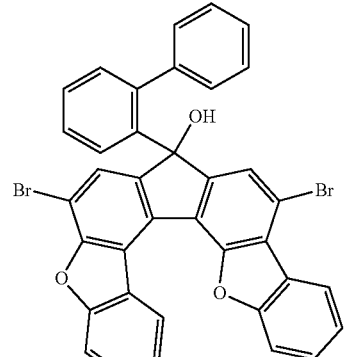

<Intermediate 3-d>

In a 100-ml round-bottom flask reactor, a mixture of 2-bromobiphenyl (2.1 g, 0.009 mol) and tetrahydrofuran (30 ml) was cooled to −78° C. under a nitrogen atmosphere. At the same temperature, n-butyl lithium (4.8 ml, 0.008 mol) was dropwise added to the mixture, and stirred for 2 hrs. Then, <Intermediate 3-c> (3.0 g, 0.006 mol) was added little by little at room temperature while stirring. When the reaction mixture started a color change, the reaction was monitored by thin layer chromatography. After the reaction was stopped with H₂O (10 ml), extraction was conducted with ethylacetate and water. The organic layer was separated, concentrated in a vacuum, and recrystallized with acetonitrile to afford <Intermediate 3-d> as a solid (2.5 g, 64%).

Synthesis Example 3-(5): Synthesis of Intermediate 3-e

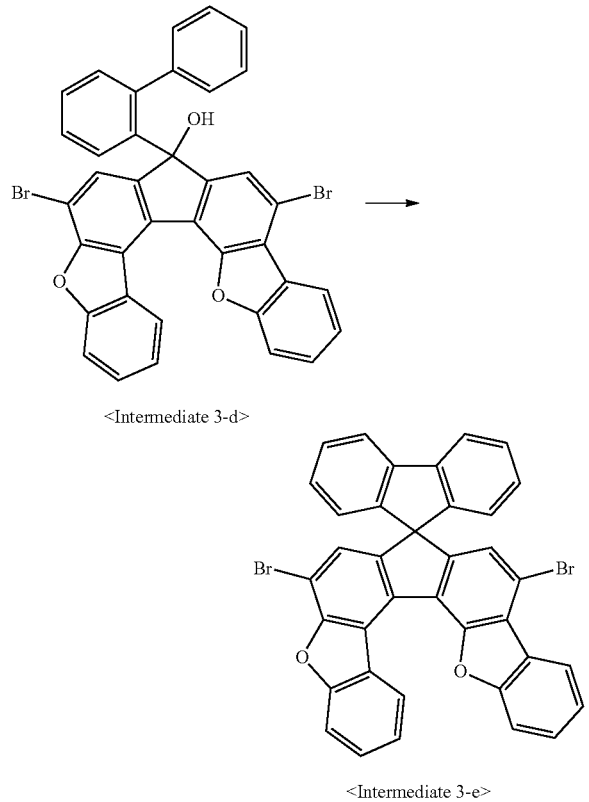

<Intermediate 3-d>

<Intermediate 3-e>

In a 100-ml round-bottom flask reactor, a mixture of <Intermediate 3-d> (2.5 g, 0.04 mol), acetic acid (25 ml), and sulfuric acid (0.5 ml) was stirred for 5 hrs under reflux. When a precipitate was formed, the completion of the reaction was monitored by thin layer chromatography. The reaction mixture was then cooled to room temperature, and filtered. The filtrate was washed with H₂O and methanol, and dissolved in monochlorobenzene. Following silica gel chromatography, the fraction was concentrated and cooled to room temperature to give <Intermediate 3-e> (2.2 g, 90%).

Synthesis Example 3-(6): Synthesis of Compound of Chemical Formula 98

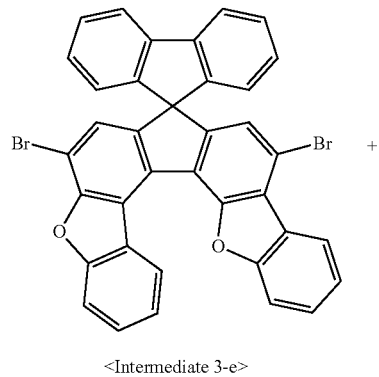

<Intermediate 3-e>

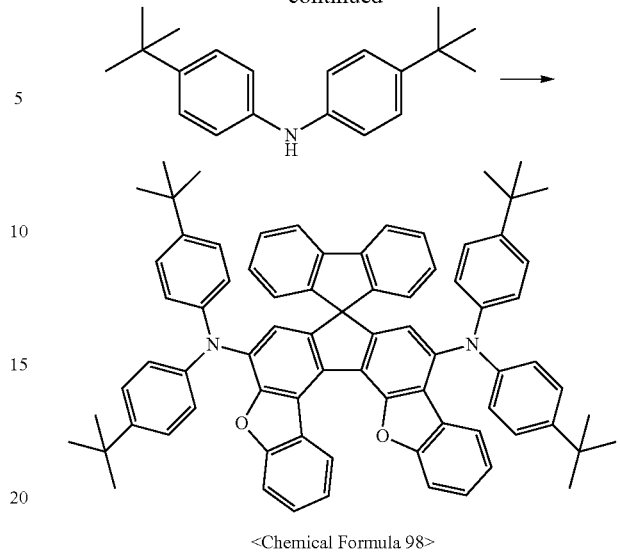

<Chemical Formula 98>

In a 100-ml round-bottom flask reactor, <intermediate 3-e> (2.2 g, 0.003 mol), 4-(tert-butyl)-N-(4-(tert-butyl)phenyl)amine (2.4 g, 0.008 mol), palladium (II) acetate (0.04 g, 0.2 mmol), sodium tert-butoxide (1.6 g, 0.016 mol), tri-tert-butyl phosphine (0.04 g, 0.2 mmol), and toluene (30 ml) were stirred together for 2 hrs under reflux. After completion of the reaction, the reaction mixture was cooled to room temperature, and extracted with dichloromethane and water. The organic layer thus formed was separated, dried over magnesium sulfate, and concentrated in a vacuum. The concentrate was purified by column chromatography and recrystallized in dichloromethane and acetone to afford <Chemical Formula 98> as a solid (1.4 g, 43%).

MS (MALDI-TOF): m/z 1086.50 [M+]

Preparation of Host Compounds

Synthesis Example 4: Synthesis of [Compound 1]

Synthesis Example 4-(1): Synthesis of Intermediate 4-a

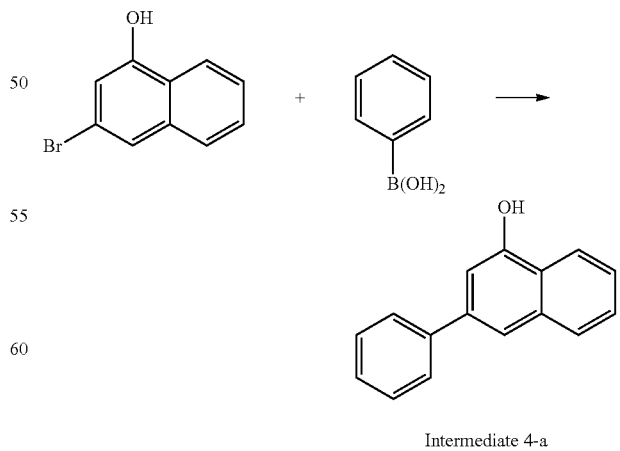

Intermediate 4-a

In a 1000-mL round-bottom flask, 3-bromo-1-naphthol (33.5 g, 0.15 mol), Pd(PPh₃)₄ (3.35 g, 3.1 mmol), potassium carbonate (43 g, 0.31 mol), and phenyl boronic acid (24.6 g, 0.2 mol) were stirred together with toluene (200 mL), 1,4-dioxane (200 mL) and water (100 mL) for 16 hrs under reflux. After completion of the reaction, the organic layer was separated and the aqueous layer was exacted twice with toluene (100 mL). The pooled organic layer was concentrated in a vacuum, and recrystallized in toluene and methanol to afford Intermediate 4-a as a solid (33 g, 75%).

Synthesis Example 4-(2): Synthesis of Intermediate 4-b

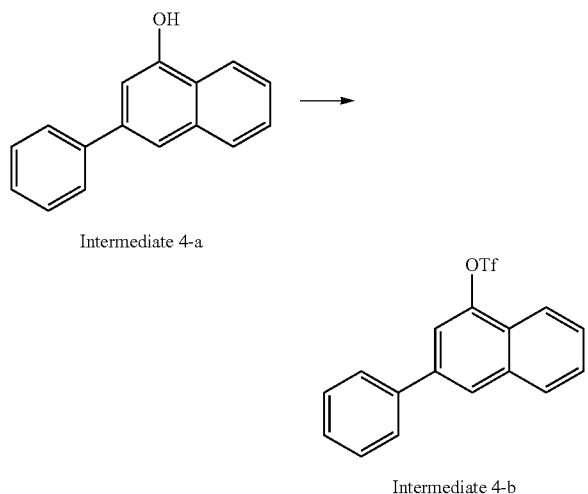

Intermediate 4-a

Intermediate 4-b

In a 1000-mL three-neck, round-bottom flask, Intermediate 4-a (30 g, 0.14 mol) was dissolved in dichloromethane (300 mL). Pyridine (14 g, 0.18 mol) was added to the solution which was then cooled to 0° C. $(CF_3SO_2)_2O$ (42.3 g, 0.15 mol) was dropwise added to the reaction mixture which was then stirred for 1 hrs at room temperature before adding water (150 mL). The organic layer was separated and concentrated in a vacuum. Purification by column chromatography afforded Intermediate 4-b (35 g, 72.9%).

Synthesis Example 4-(3): Synthesis of Intermediate 4-c

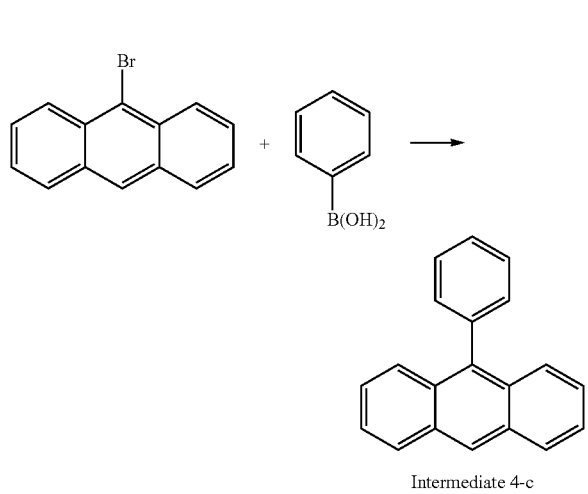

Intermediate 4-c

In a 10-L 4-neck round-bottom flask, 9-bromoanthracene (400 g, 1.55 mol), Pd(PPh$_3$)$_4$ (35.99 g, 0.031 mol), potassium carbonate (430.7 g, 3.11 mol), and phenyl boronic acid (246.6 g, 2.02 mol) were stirred together with toluene (2000 mL), 1,4-dioxane (2000 mL) and water (1000 mL) for 16 hrs under reflux. After completion of the reaction, the organic layer was separated and concentrated in a vacuum. Recrystallization in toluene and methanol afforded Intermediate 4-c as a solid (298 g, 75.3%).

Synthesis Example 4-(4): Synthesis of Intermediate 4-d

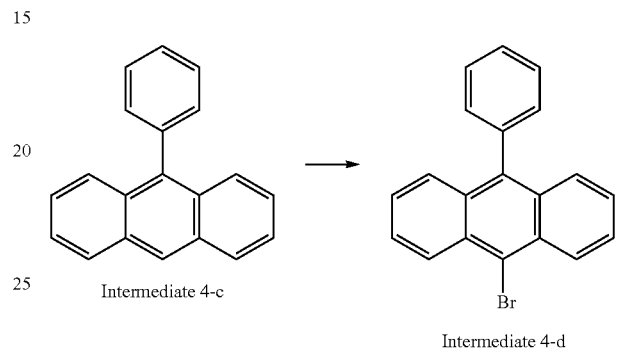

Intermediate 4-c

Intermediate 4-d

In a 10-L 4-neck round-bottom flask, Intermediate 4-c (298 g, 1.17 mol) was dissolved in dichloromethane (4000 mL). The solution was cooled to 0° C. and mixed slowly with drops of bromine (206 g, 1.29 mol). Subsequently, the reaction mixture was stirred at room temperature for 2 hrs. After completion of the reaction, an aqueous sodium hydrogen carbonate solution (1000 mL) was added, and stirred for 30 min. The organic layer thus formed was separated, concentrated in a vacuum, and recrystallized in dichloromethane and methano to afford Intermediate 4-d (313 g, 80.3%).

Synthesis Example 4-(5): Synthesis of Intermediate 4-e

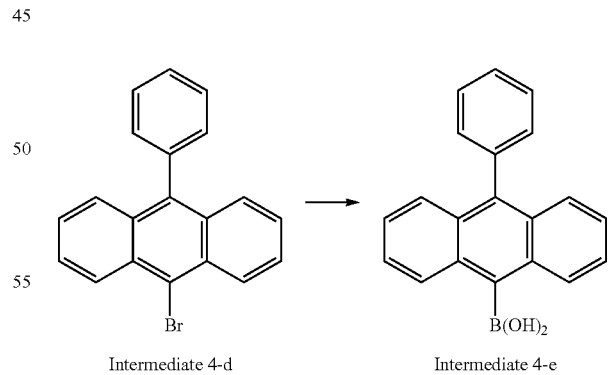

Intermediate 4-d

Intermediate 4-e

In a 10-L 4-neck, round-bottom flask, Intermediate 4-d (280 g, 0.84 mol) and THF (3000 mL) were placed and maintained at −78° C. 1.6M n-BuLi (630 mL) was slowly added to the solution which was then stirred for 2 hrs. At the same temperature, B(OMe)$_3$ was dropwise added. The temperature was elevated to room temperature before stirring for 12 hrs. After completion of the reaction, 2N HCl was added. The organic layer was separated, neutralized, and recrystallized in toluene to afford Intermediate 4-e (228 g, 91%).

Synthesis Example 4-(6): Synthesis of [Compound 1]

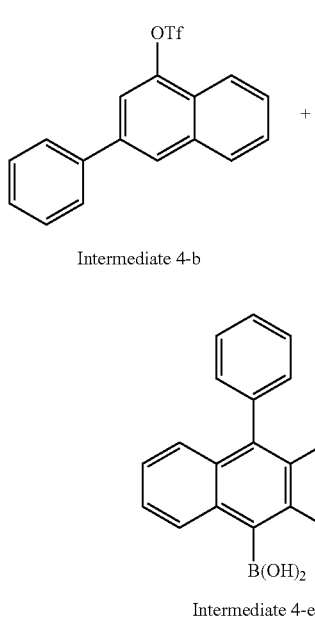

Intermediate 4-b

+

Intermediate 4-e

→

[Compound 1]

In a 1000-mL L 4-neck round-bottom flask, Intermediate 4-b (30 g, 0.085 mol), Pd(PPh$_3$)$_4$ (2.5 g, 0.002 mol), potassium carbonate (29.4 g, 0.21 mol), and Intermediate 4-e (33 g, 0.11 mol) were stirred together with toluene (300 mL), ethanol (150 mL) and water (150 mL) for 12 hrs under reflux. After completion of the reaction, the organic layer was separated, concentrated in a vacuum, and recrystallized in toluene and methanol to afford [Compound 1] (22 g, 56.7%). The compound was identified through NMR.

δ 8.32 (1H), 8.12 (1H), 7.94-7.93 (1H), 7.86-7.83 (2H), 7.80 (1H), 7.77 (1H), 7.69-7.48 (11H), 7.42-7.33 (3H), 7.30-7.26 (3H)

Synthesis Example 5: Synthesis of [Compound 40]

Synthesis Example 5-(1): I Synthesis of Intermediate 5-a

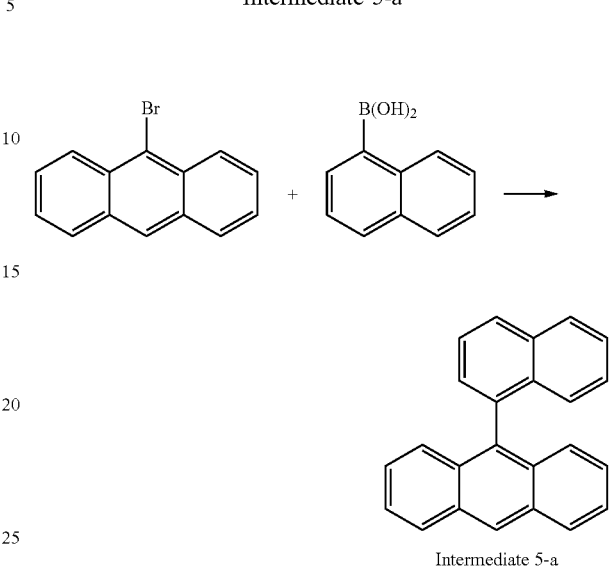

Intermediate 5-a

In a 2-L 4-neck round-bottom flask, 9-bromoanthracene (93.1 g, 0.36 mol), Pd(PPh$_3$)$_4$ (12.7 g, 0.011 mol), potassium carbonate (132 g, 0.91 mol) and 1-naphthalene boronic acid (87.2 g, 0.51 mol) were stirred together with toluene (500 mL) tetrahydrofuran (500 mL) and water (200 mL) for 16 hrs under reflux. After completion of the reaction, the organic layer was separated while the aqueous layer was extracted twice with toluene (1000 mL). The pooled organic layer was concentrated in a vacuum, and recrystallized in toluene and methanol to afford Intermediate 5-a (88 g, 79.4%).

Synthesis Example 5-(2): Synthesis of Intermediate 5-b

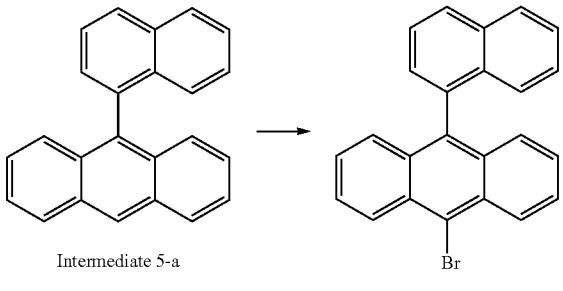

Intermediate 5-a     Intermediate 5-b

In a 2-L 4-neck round-bottom flask, Intermediate 5-a (88 g 0.29 mol) was dissolved in dimethylformamide (700 mL). Thereafter, a solution of NBS (70.7 g, 0.4 mole) in dimethylformamide (200 ml) was slowly added, followed by stirring for 2 hrs. After completion of the reaction, the reaction mixture was mixed with water to precipitate Intermediate 5-b (108 g, 97.5%).

Synthesis Example 5-(3): Synthesis of Intermediate 5-c

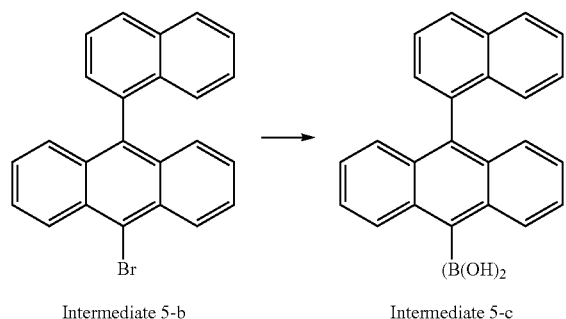

Intermediate 5-b → Intermediate 5-c

In a 4-neck round-bottom flask, Intermediate 5-b 5 g (0.2 mol) and tetrahydrofuran (750 mL) were placed and maintained at −78° C. 1.6M n-BuLi (150 mL) was slowly added to the solution which was then stirred for 2 hrs. At the same temperature, B(OMe)$_3$ was dropwise added. The temperature was elevated to room temperature before stirring for 12 hrs. After completion of the reaction, 2N HCl was added. The organic layer was separated, neutralized, and recrystallized in toluene to afford Intermediate 5-c (30 g, 45%).

Synthesis Example 5-(4): Synthesis of [Compound 40]

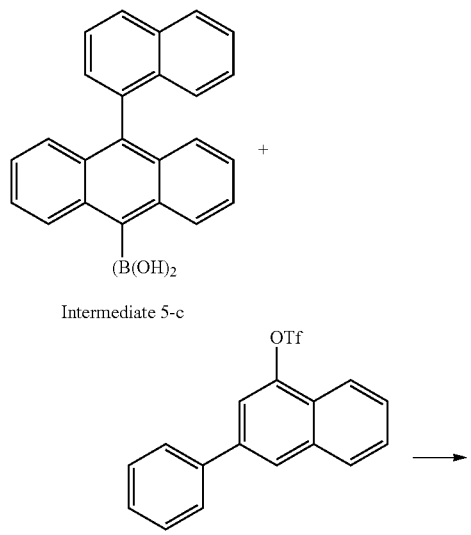

In a 1000-mL L 4-neck round-bottom flask, Intermediate 5-c (28.5 g, 0.082 mol), Pd(PPh$_3$)$_4$ (1.5 g, 0.001 mol), potassium carbonate (18.1 g, 0.13 mol), and Intermediate 4-b (20.3 g, 0.07 mol) were stirred together with toluene (250 mL), ethanol (125 mL) and water (125 mL) for 12 hrs under reflux. After completion of the reaction, the organic layer was separated while the aqueous layer was extracted once with toluene (200 mL). The pooled organic layer was concentrated in a vacuum, and recrystallized in toluene and methanol to afford [Compound 40] (21.1 g, 50.9%). The compound was identified through NMR.

δ 8.34 (1H), 8.13-7.97 (5H), 7.80 (1H), 7.77 (1H), 7.76-7.49 (11H), 7.48-7.23 (7H)

Synthesis Example 6: Synthesis of [Compound 36]

Synthesis Example 6-(1): Synthesis of Intermediate 6-a

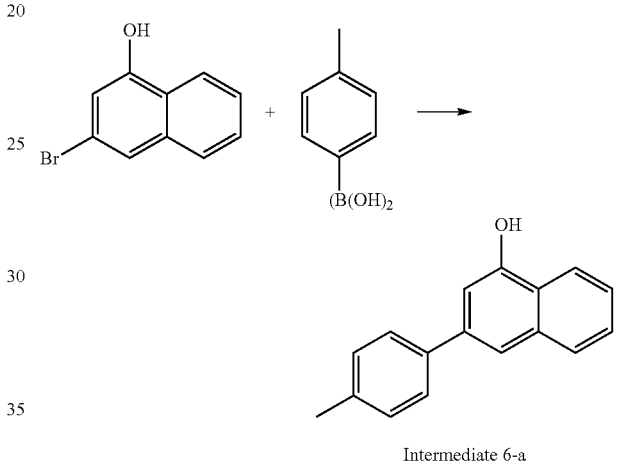

Intermediate 6-a

Intermediate 6-a was synthesized in the same manner as in Synthesis Example 4-(1), with the exception that 3-bromo-1-naphthol and toluene-4-boronic acid were used.

Synthesis Example 6-(2): Synthesis of Intermediate 6-b

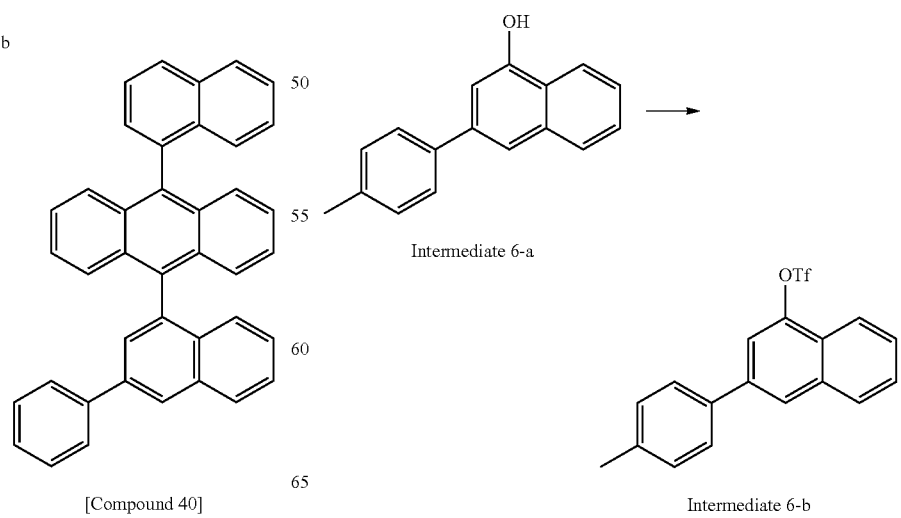

Intermediate 6-a → Intermediate 6-b

In a 1000-mL, 3-neck, round-bottom flask, Intermediate 6-a (20 g, 0.09 mol) was dissolved in dichloromethane (200 mL). Pyridine (8.8 g, 0.11 mol) was added to the solution which was then cooled to 0° C. (CF$_3$SO$_2$)$_2$O (26.5 g, 0.09 mol) was dropwise added to the reaction mixture which was then stirred for 1 hrs at room temperature before adding water (150 mL). The organic layer was separated and concentrated in a vacuum. Purification by column chromatography afforded Intermediate 6-b (25 g, 79.9%).

Synthesis Example 6-(3): Synthesis of [Compound 36]

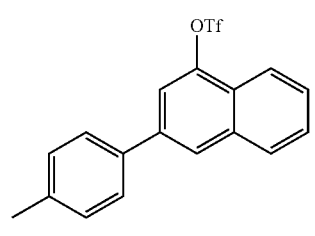

Intermediate 6-b

+

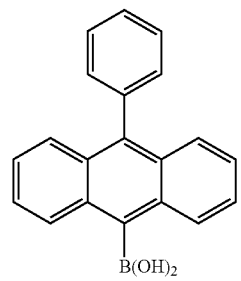

Intermediate 4-e

→

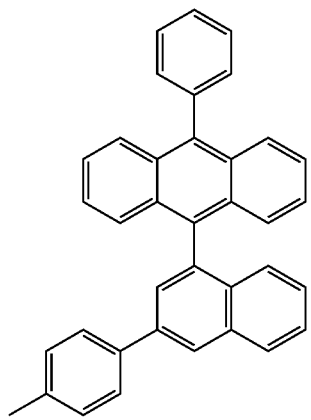

[Compound 36]

In a 1000-mL, 4-neck round-bottom flask, Intermediate 6-b (25 g, 0.082 mol), Pd(PPh$_3$)$_4$ (1.5 g, 0.001 mol), potassium carbonate (18.1 g, 0.13 mol), and Intermediate 4-e (20.3 g, 0.07 mol) were stirred together with toluene (250 mL), ethanol (125 mL) and water (125 mL) for 12 hrs under reflux. After completion of the reaction, the organic layer was separated while the aqueous layer was extracted once with toluene (200 mL). The pooled organic layer was concentrated in a vacuum, and recrystallized in toluene and methanol to afford [Compound 36] (13 g, 52.9%). The compound was identified through NMR.

δ 8.32 (1H), 8.12 (1H), 7.94-7.93 (1H), 7.86-7.83 (2H), 7.80 (1H), 7.77 (1H), 7.55-7.51 (6H), 7.41-7.33 (10H), 2.34 (3H)

Synthesis Example 7: Synthesis of [Compound 22]

Synthesis Example 7-(1): Synthesis of Intermediate 7-a

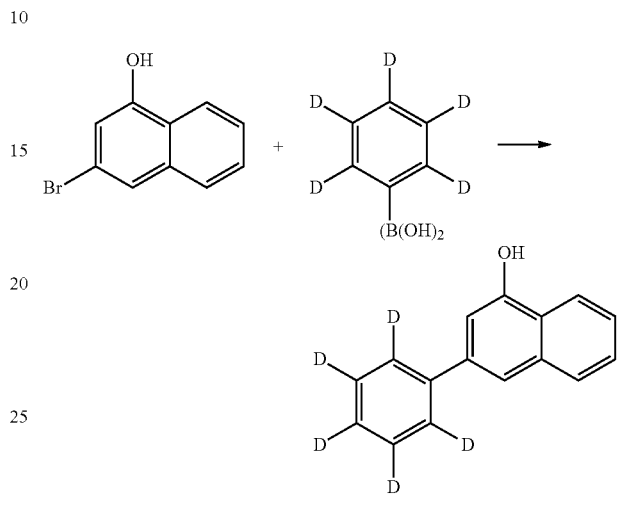

Intermediate 7-a

Intermediate 7-a was synthesized in the same manner as in Synthesis Example 4-(1), with the exception that phenyl (d5) boronic acid was used.

Synthesis Example 7-(2): Synthesis of Intermediate 7-b

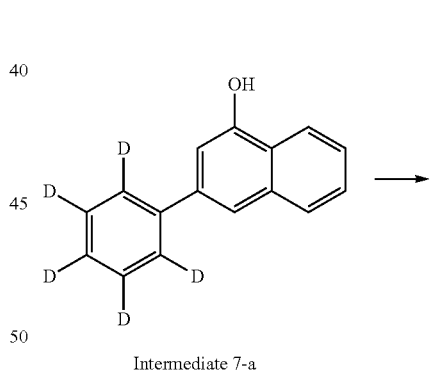

Intermediate 7-a

→

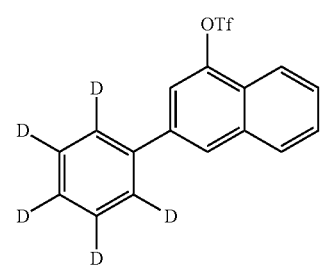

Intermediate 7-b

Intermediate 7-b was synthesized in the same manner as in Synthesis Example 4-(2), with the exception that Intermediate 7-a was used.

Synthesis Example 7-(3): Synthesis of Intermediate 7-c

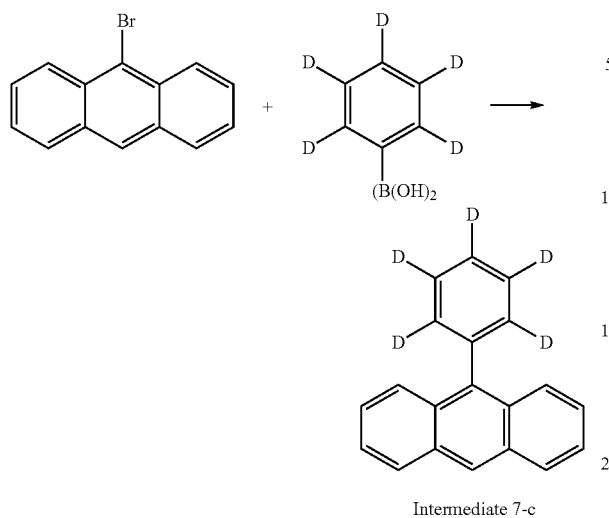

Intermediate 7-c

Intermediate 7-c was synthesized in the same manner as in Synthesis Example 4-(3), with the exception that Intermediate 7-b was used.

Synthesis Example 7-(4): Synthesis of Intermediate 7-d

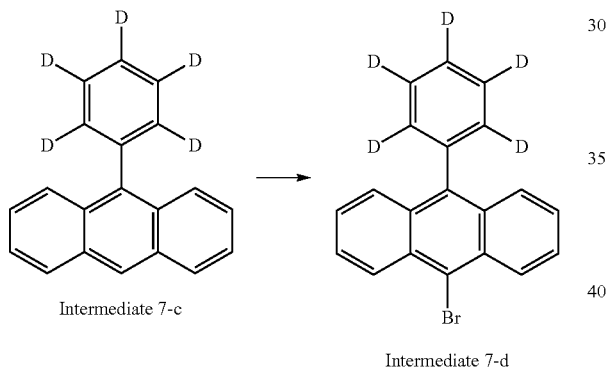

Intermediate 7-c          Intermediate 7-d

Intermediate 7-c was synthesized in the same manner as in Synthesis Example 4-(4), with the exception that Intermediate 7-c was used.

Synthesis Example 7-(5): Synthesis of Intermediate 7-e

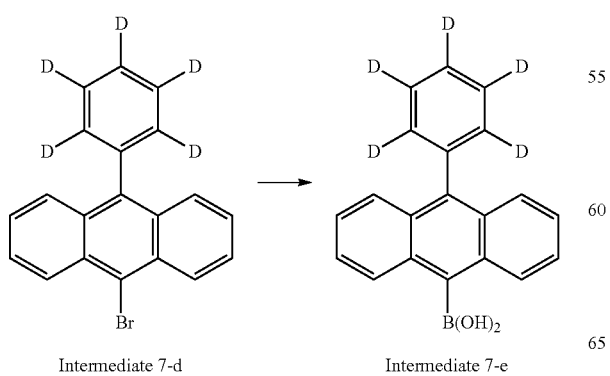

Intermediate 7-d          Intermediate 7-e

Intermediate 7-e was synthesized in the same manner as in Synthesis Example 4-(5), with the exception that Intermediate 7-d was used.

Synthesis Example 7-(6): Synthesis of [Compound 22]

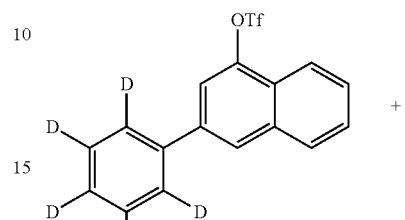

Intermediate 7-b

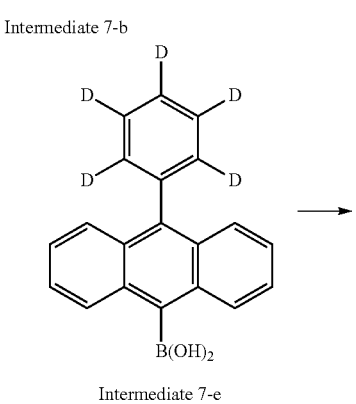

Intermediate 7-e

[Compound 22]

Compound 22 was synthesized in the same manner as in Synthesis Example 4-(6), with the exception that Intermediates 7-b and 7-e were used.

MS (MALDI-TOF): m/z 466.25 [M+]

Examples 1 to 9: Fabrication of Organic Light-Emitting Diode

An ITO glass substrate was patterned to have a luminescence area of 2 mm×2 mm, and cleansed. The ITO glass was mounted in a vacuum chamber that was then set to have a base pressure of 1×10$^{-7}$ torr. On the ITO glass substrate, films were formed of DNTPD (400 Å) and α-NPD (200 Å) in the order. A light-emitting layer (200 Å) was formed of a mixture of a host and a dopant as shown in Table 1, below. Then, [Chemical Formula E-1] was deposited to form an electron transport layer 300 Å thick, on which an electron injection layer (5 Å) was formed of [Chemical Formula E-2] and then covered with an Al layer (1000 Å) to fabricate an organic light-emitting diode.

The organic light-emitting diodes thus obtained were measured at 10 mA/cm$^2$ for luminescence properties.

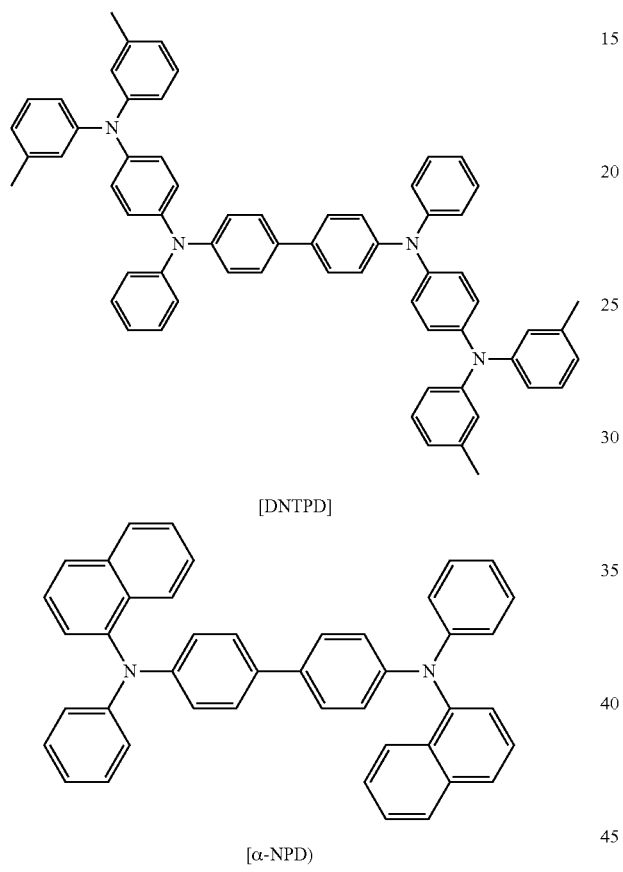

[DNTPD]

[α-NPD]

[Chemical Formula E-1]

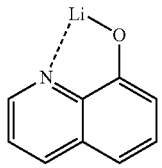

[Chemical Formula E-2]

Comparative Examples 1 and 2

Organic light-emitting diodes were fabricated in the same manner as in Examples 2 and 3, with the exception that [BD1] was used as a dopant in a light-emitting layer. Luminescence properties of the organic light-emitting diodes were measured at 10 mA/cm$^2$. The structure of [BD1] is as follows.

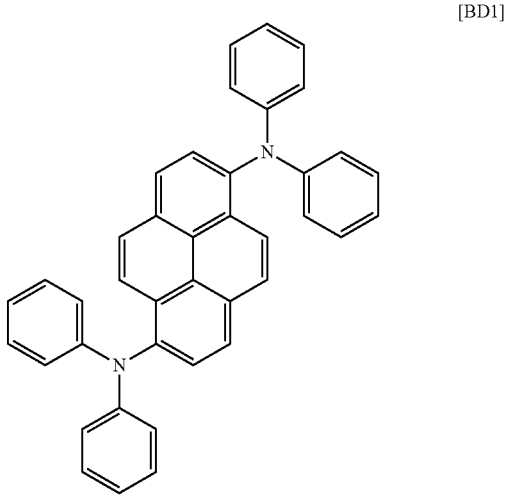 [SMILES: c1ccc(N(c2ccccc2)c2ccc3ccc4c(N(c5ccccc5)c5ccccc5)ccc5ccc2c3c54)cc1]

[BD1]

Comparative Examples 3 and 4

Organic light-emitting diodes were fabricated in the same manner as in Examples 1 and 2, with the exception that [BH1] was used as a host in a light-emitting layer. Luminescence properties of the organic light-emitting diodes were measured at 10 mA/cm$^2$.

The structure of [BH1] is as follows.

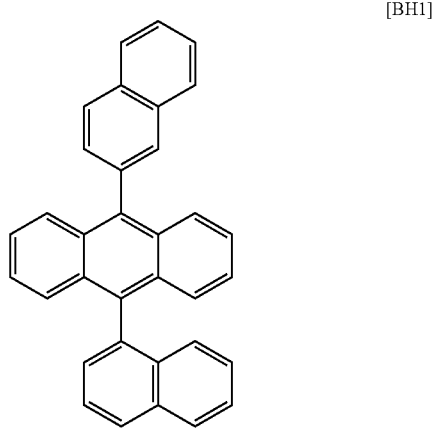 [SMILES: c1ccc2cc(-c3c4ccccc4c(-c4cccc5ccccc45)c4ccccc34)ccc2c1]

[BH1]

The organic light-emitting diodes fabricated in Examples 1 to 7 and Comparative Examples 1 to 4 were measured for color coordinate, and lifetime, and the results are summarized in Table 1, below.

In Table 1, T97 refers to a time taken for the initial luminance to decrease by 3%.

TABLE 1

| Ex. # | Host   | Dopant          | CIEx  | CIEy  | T97 |
|-------|--------|-----------------|-------|-------|-----|
| 1     | Cpd. 1 | Chem. Formula 1 | 0.138 | 0.112 | 123 |
| 2     | Cpd. 1 | Chem. Formula 231 | 0.137 | 0.114 | 132 |
| 3     | Cpd. 40 | Chem. Formula 1 | 0.138 | 0.106 | 135 |
| 4     | Cpd. 40 | Chem. Formula 231 | 0.138 | 0.107 | 142 |
| 5     | Cpd. 36 | Chem. Formula 1 | 0.138 | 0.106 | 137 |
| 6     | Cpd. 36 | Chem. Formula 231 | 0.138 | 0.106 | 140 |
| 7     | Cpd. 1 | Chem. Formula 98 | 0.138 | 0.106 | 146 |
| 8     | Cpd. 22 | Chem. Formula 1 | 0.138 | 0.106 | 128 |
| 9     | Cpd. 22 | Chem. Formula 98 | 0.138 | 0.106 | 131 |
| C. 1  | Cpd. 1 | BD 1            | 0.134 | 0.120 | 66  |
| C. 2  | Cpd. 40 | BD 1           | 0.135 | 0.115 | 50  |
| C. 3  | BH 1   | Chem. Formula 1 | 0.138 | 0.108 | 77  |
| C. 4  | BH 1   | Chem. Formula 231 | 0.138 | 0.109 | 73 |

As is understood from the data of Table 1, the organic light-emitting diodes of the present disclosure exhibited a longer lifetime than the organic light-emitting diodes using the compounds of Comparative Examples 1 to 4, thereby demonstrating their high applicability to organic electroluminescence devices.

Although the preferred embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed is:

1. An organic light-emitting diode, comprising:
an organic light-emitting diode, comprising:
a first electrode;
a second electrode facing the first electrode;
a light-emitting layer intercalated between the first electrode and the second electrode, wherein the light-emitting layer comprises at least one of the amine compounds represented by the following Chemical Formula B, and at least one of the anthracene compounds represented by the following Chemical Formula C, and wherein the light-emitting layer comprises a host and a dopant, the amine compound of Chemical Formula B serving as the dopant and the compound of Chemical Formula C serving as the host:

[Chemical Formula B]

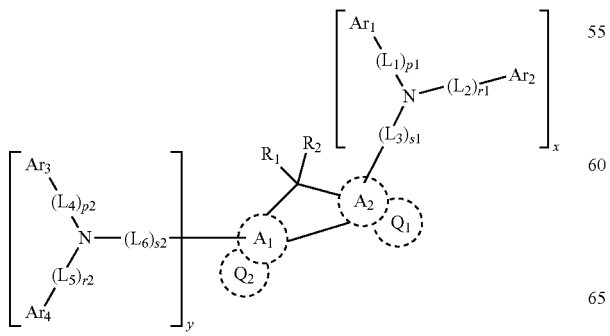

-continued

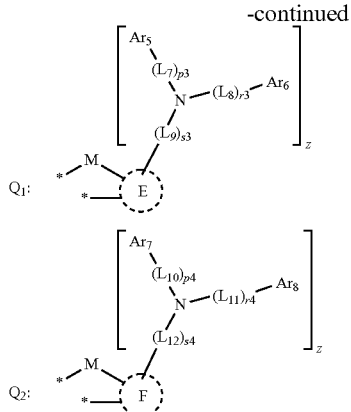

wherein, $A_1$, $A_2$, E, and F are the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

linkers $L_1$ to $L_{12}$ are the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ are the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, in the alterative for $R_1$ and $R_2$, $R_1$ and $R_2$ together form a mono- or polycyclic aliphatic or aromatic ring, and in the alternative for $Ar_1$ to $Ar_8$, $Ar_1$ forms a ring with $Ar_2$, $Ar_3$ forms a ring with $Ar_4$, $Ar_5$ forms a ring with $Ar_6$, and/or $Ar_7$ forms a ring with $Ar_8$;

p1 to p4, $r_1$ to $r_4$, and s1 to s4 are each independently an integer of 1 to 3, with the proviso that when any of them is 2 or greater, the corresponding linkers are the same or different, in Chemical Formula B, x is an integer of 1 or 2, and y and z are the same or different and are each independently an integer of 0 to 3; and two adjacent carbon atoms of the $A_2$ ring moiety of Chemical Formula B occupy respective positions * of Structural Formula $Q_1$ to form a fused ring, and two adjacent carbon atoms of the $A_1$ ring moiety of Chemical Formula B occupy respective positions * of structural Formula $Q_2$ to form a fused ring, and

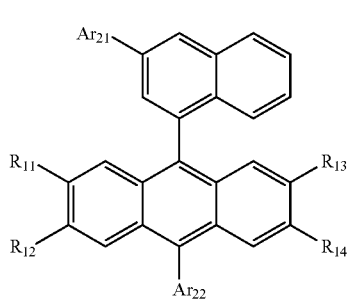

[Chemical Formula C]

wherein, $Ar_{21}$ and $Ar_{22}$ of Chemical Formula C are the same or different, and are each independently selected from among a substituted or unsubstituted aryl of 6 to 50 carbon atoms, $R_{11}$ to $R_{14}$ are the same or different and are each independently selected from the group consisting of hydrogen, deuterium, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 30 carbon atoms containing O, N or S as a heteroatom, a substituted or unsubstituted silicon, a substituted or unsubstituted boron, a substituted or unsubstituted silane, a carbonyl, a phosphoryl, an amino, a nitrile, a hydroxy, a nitro, a halogen, an amide, and an ester, a hydrogen atom is positioned on each of the aromatic ring carbon atoms to which none of the substituents $Ar_{21}$, $Ar_{22}$, and $R_{11}$ to $R_{14}$ are bonded, in the alternative for $R_{11}$, $R_{12}$, $R_{13}$, and $R_{14}$, $R_{11}$ and $R_{12}$ are bonded to each other to form a saturated or unsaturated ring, and/or $R_{13}$ and $R_{14}$ are bonded to each other to form a saturated or unsaturated ring, and wherein the term 'substituted' in the expression 'substituted or unsubstituted' means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

2. The organic light-emitting diode of claim 1, wherein $A_1$, $A_2$, E, and F of Chemical Formula B are identical or different, and are each independently a substituted or unsubstituted aromatic hydrocarbon ring of 6 to 50 carbon atoms.

3. The organic light-emitting diode of claim 2, wherein the substituted or unsubstituted aromatic hydrocarbon ring of 6 to 50 carbon atoms is selected from among compounds represented by [Structural Formula 10] to [Structural Formula 21]:

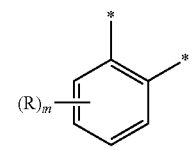

[10]

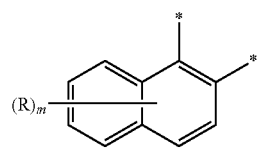

[11]

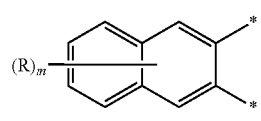

[12]

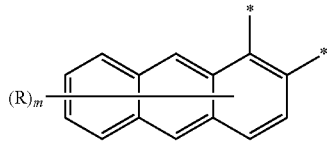

[13]

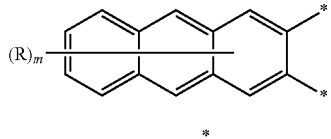

[14]

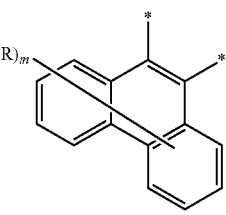

[15]

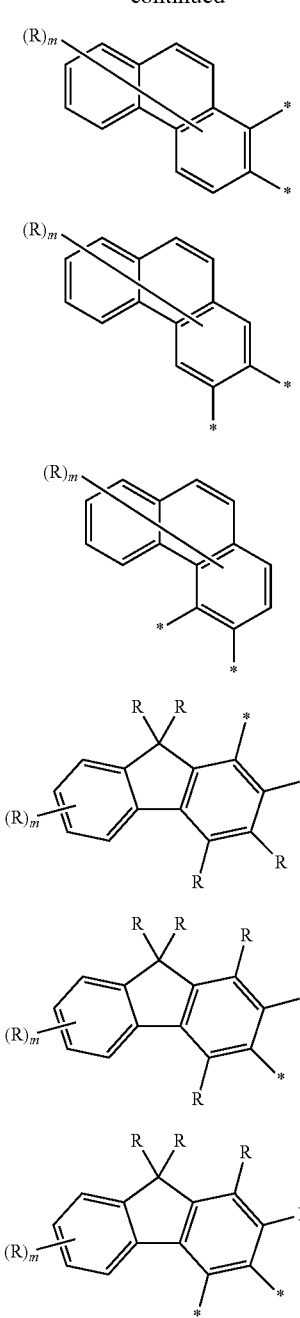

wherein,

"-*" for moiety A₁ or A₂ denotes a bonding site for forming a 5-membered ring containing the carbon atom connected to both the substituents R₁ and R₂, and "-*" for moiety E or F denotes a bonding site for forming a 5-membered ring containing M of the structural Formula Q₁ and Q₂ with moiety A₁ or A₂, when one of the aromatic hydrocarbon rings of [Structural Formula 10] to [Structural Formula 21] for A₁ or A₂ is bonded to Structural Formula Q₁ or Structural Formula Q₂, two adjacent carbon atoms of the aromatic hydrocarbon ring occupy respective positions * of Structural Formula Q₁ or Q₂ to form a fused ring; and R in Structural Formulas 10 to 21 is the same as above defined for R₁ and R₂, and m is an integer of 1 to 8, with a proviso that when m is 2 or greater or when R is 2 or greater, the corresponding Rs are the same or different.

4. The organic light-emitting diode of claim 1, wherein the linkers L₁ to L₁₂ represent single bonds, or are each any one selected from the following [Structural Formula 22] to [Structural Formula 30], p1 to p4, R₁ to R₄, and s1 to s4 are each 1 or 2, and x is 1:

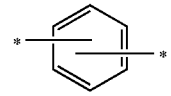

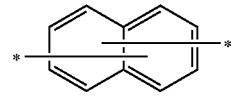

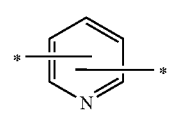

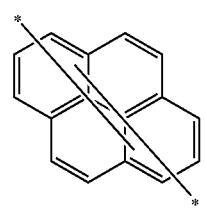

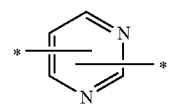

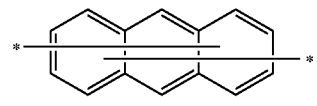

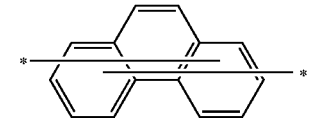

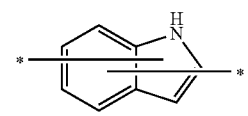

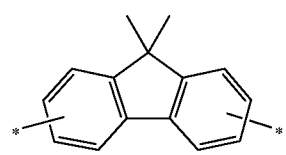

wherein hydrogen or deuterium is positioned on a carbon atom as a member in the aromatic rings of the linkers.

5. The organic light-emitting diode of claim 1, wherein x and y are each 1, and z is 0 or 1 for Chemical Formula B.

6. The organic light-emitting diode of claim 1, wherein Aril of Chemical Formula C is a substituted or unsubstituted aryl of 6 to 18 carbon atoms.

7. The organic light-emitting diode of claim 1, wherein the amine compound is any one selected from among compounds represented by the following [Chemical Formula 25] to [Chemical Formula 32], [Chemical Formula 85], [Chemical Formula 97], [Chemical Formula 98], [Chemical Formula 102], [Chemical Formula 117], [Chemical Formula 142] to [Chemical Formula 149], [Chemical Formula 160], [Chemical Formula 162], [Chemical Formula 164], [Chemical Formula 165], [Chemical Formula 197] to [Chemical Formula 201], [Chemical Formula 222] to [Chemical Formula 224], [Chemical Formula 227] to [Chemical Formula 231], and [Chemical Formula 239]:

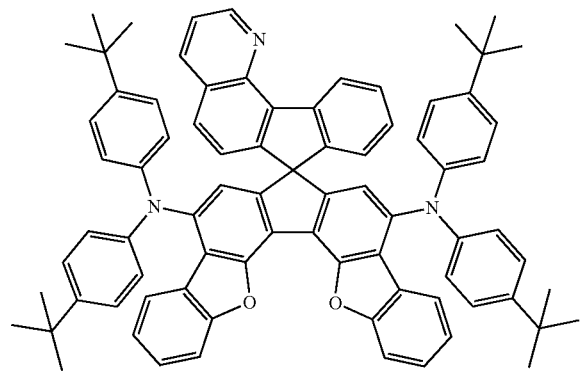

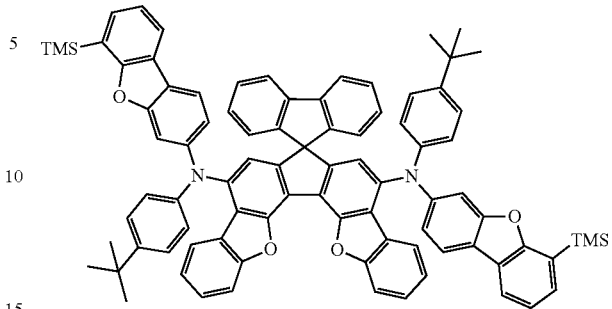

<32>
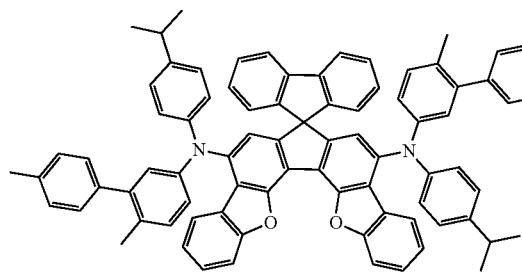
<85>
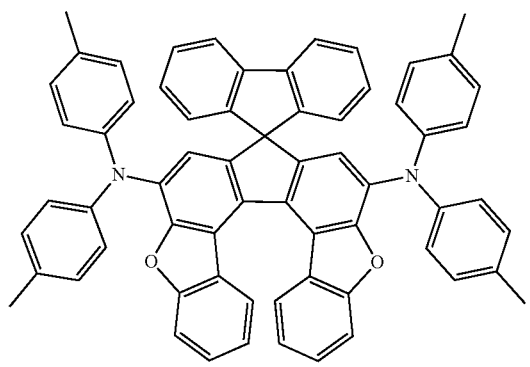
<97>
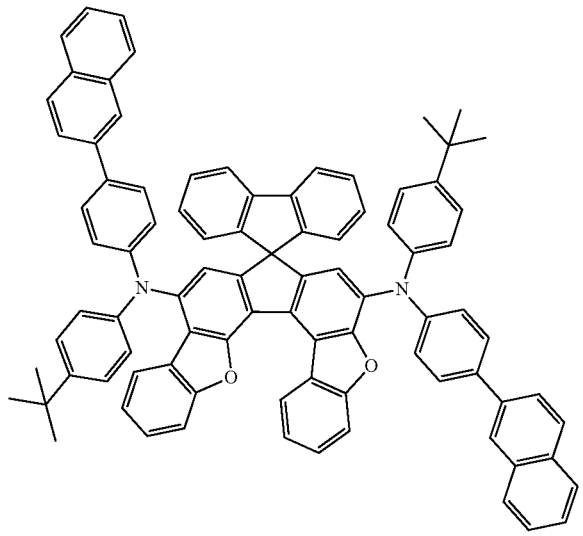
<98>
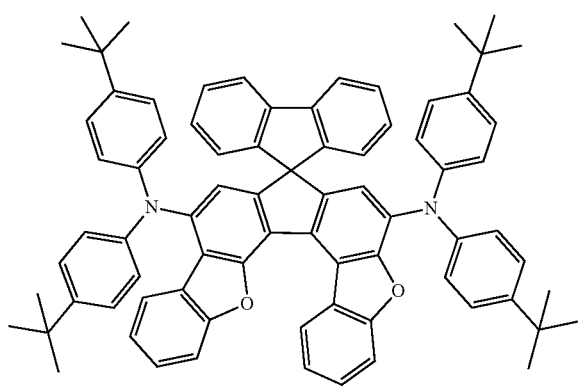
<102>
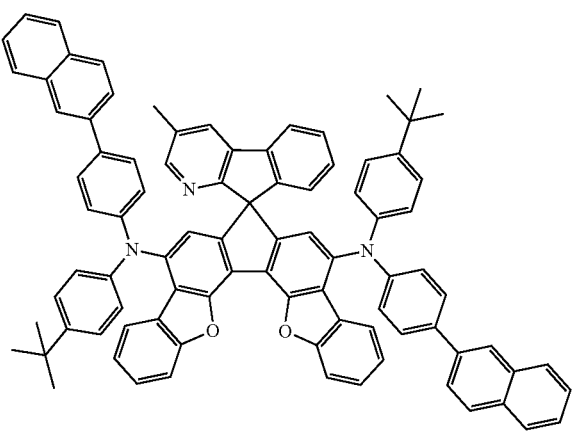
<117>
<142>
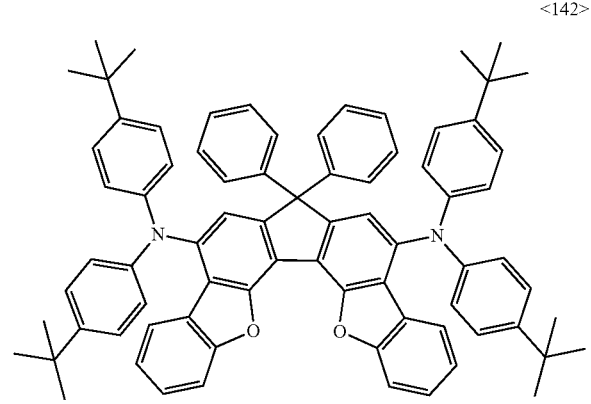

<143>
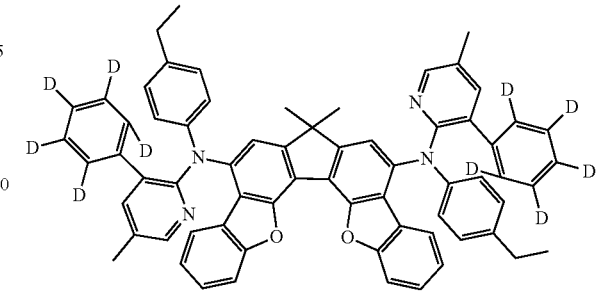
<144>
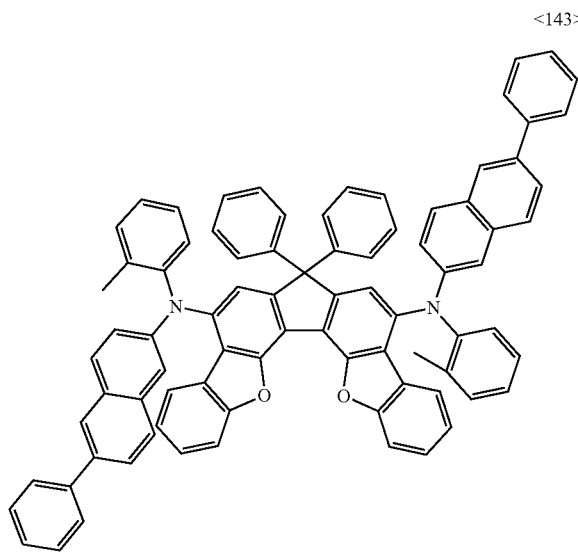
<145>
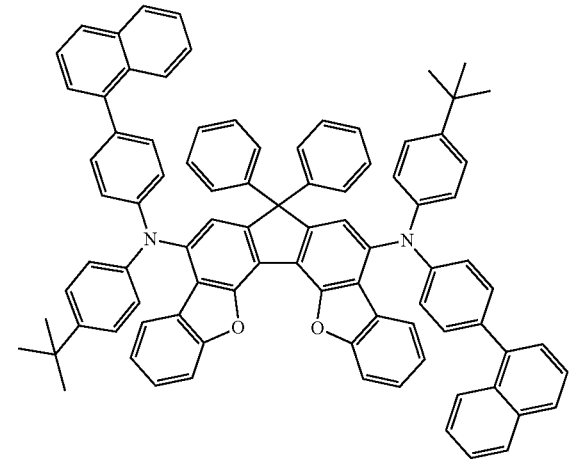
<146>
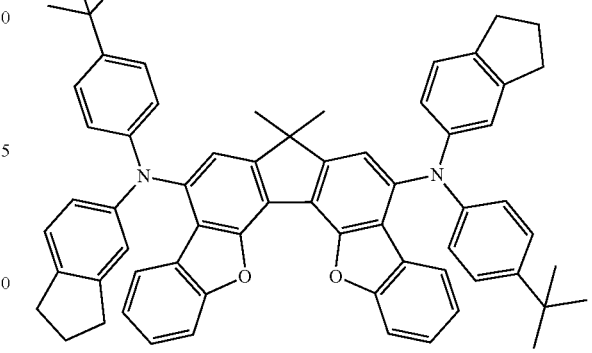
<147>
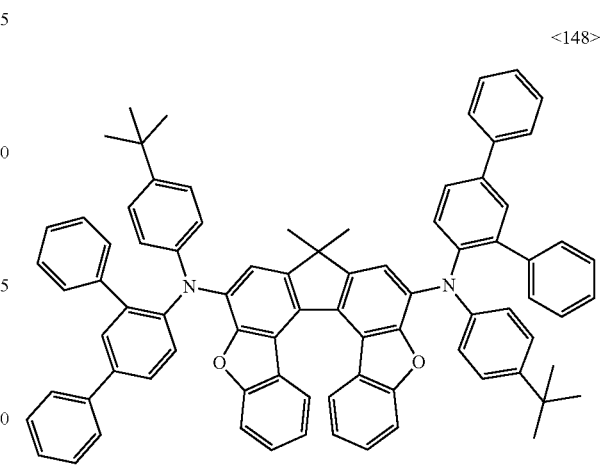
<148>
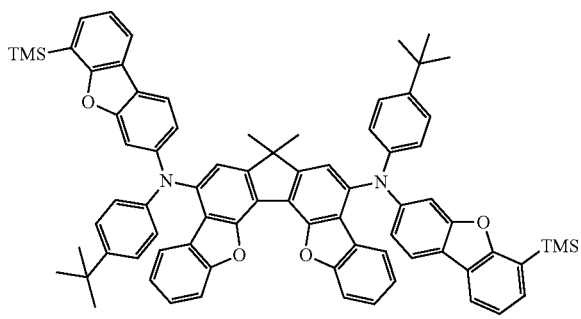
<149>
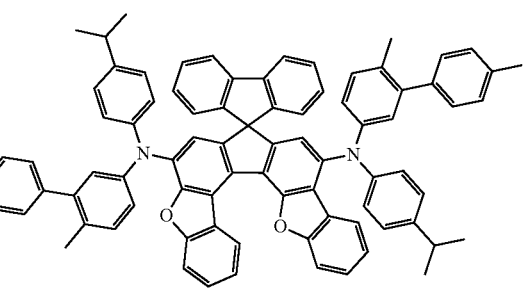

<160>
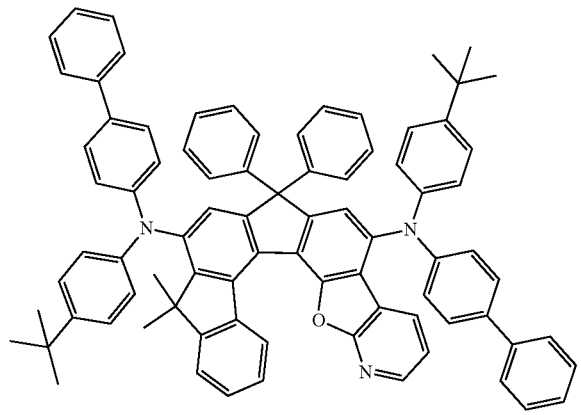
<162>
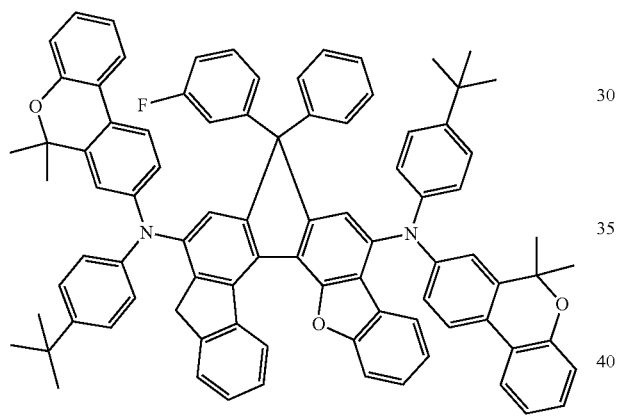
<164>
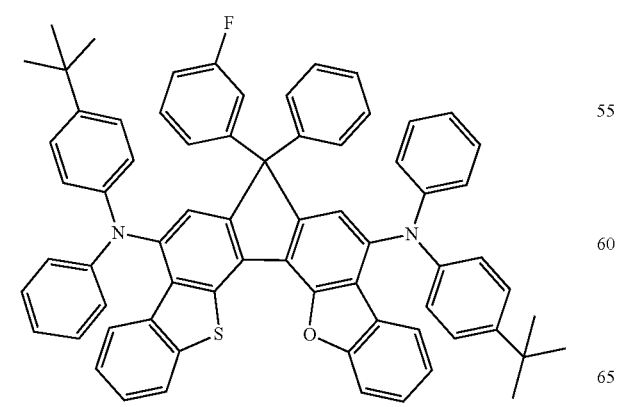
<165>
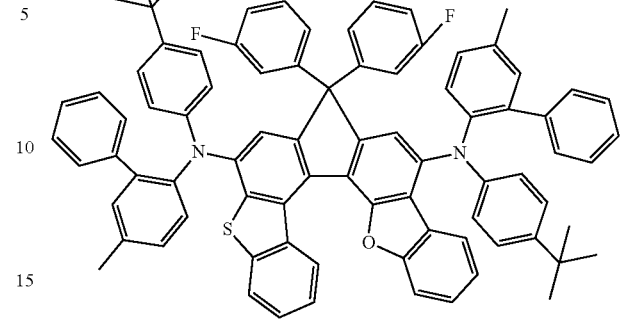
<197>
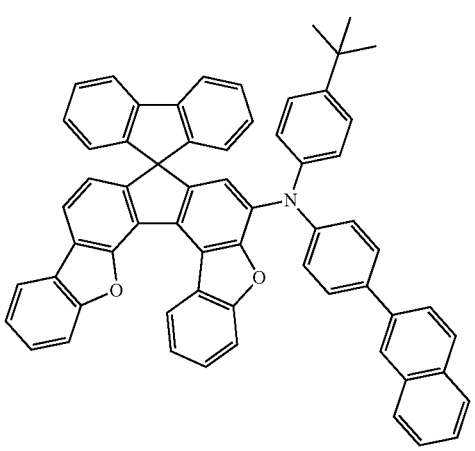
<198>
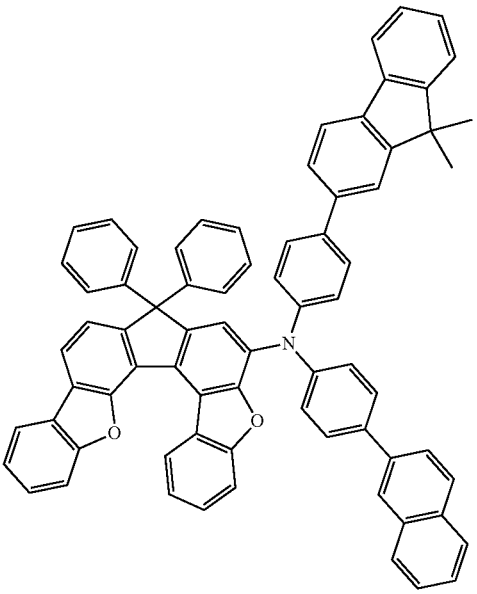

-continued
<199>
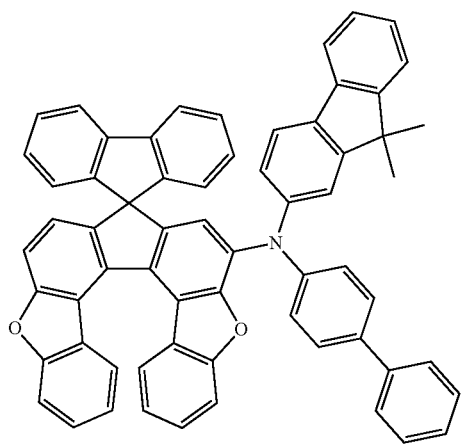
<200>
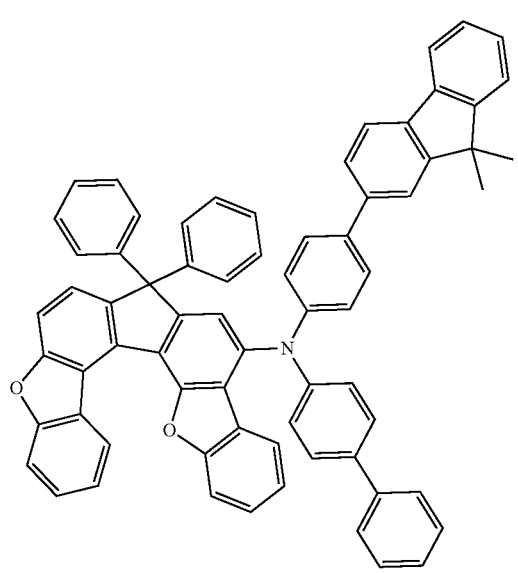
<201>
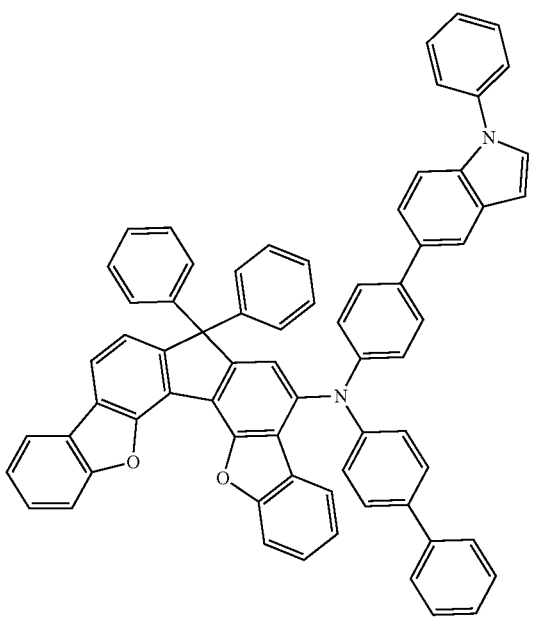
-continued
<222>
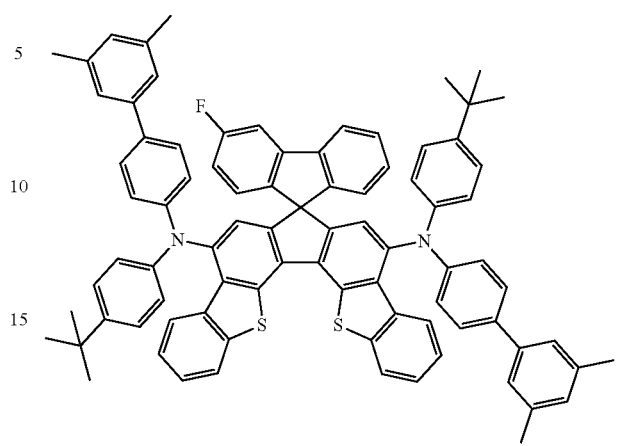
<223>
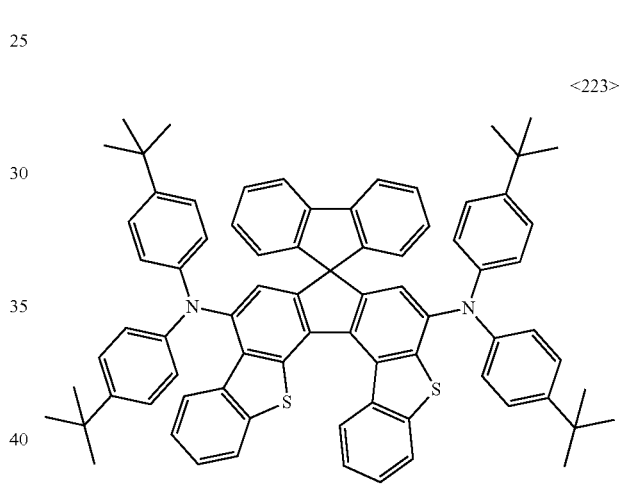
<224>
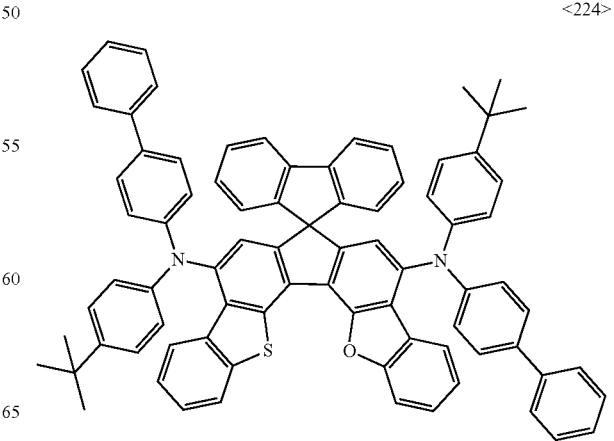

<227>
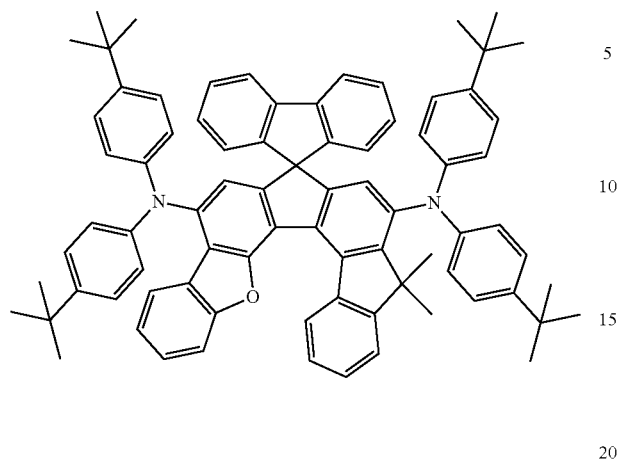
<230>
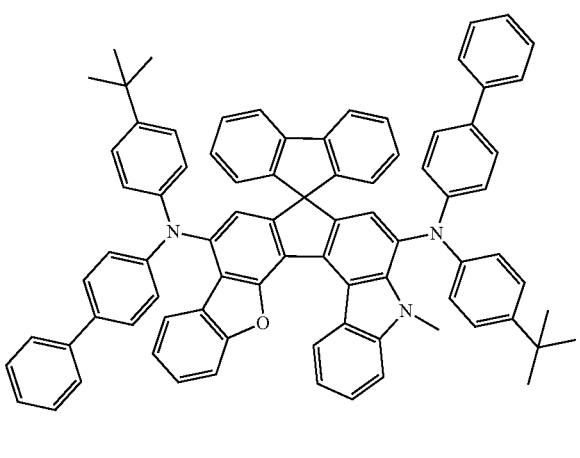
<228>
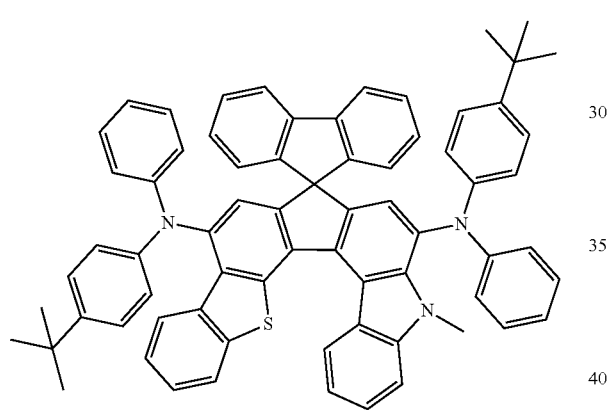
<231>
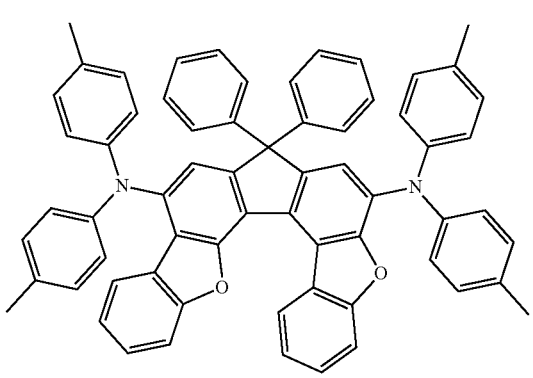
<229>
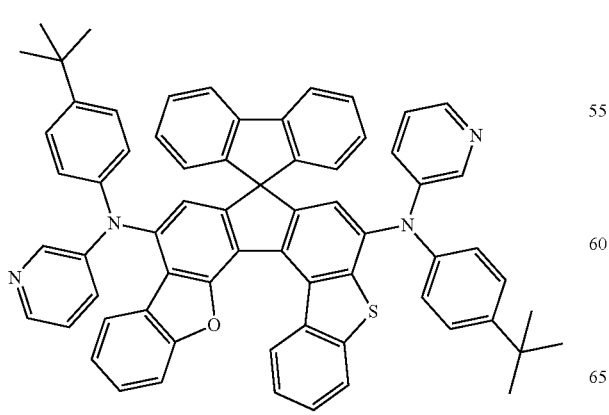
<239>
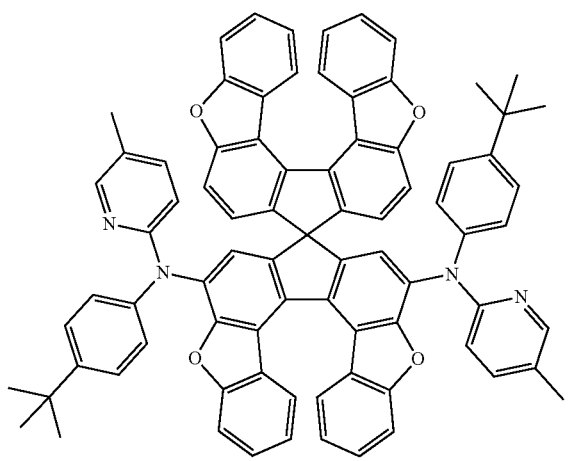

8. The organic light-emitting diode of claim 1, wherein the anthracene compound represented by Chemical Formula C is any one selected from among the following Compounds 1 to 10, and 13 to 80:
[Cpd. 1]
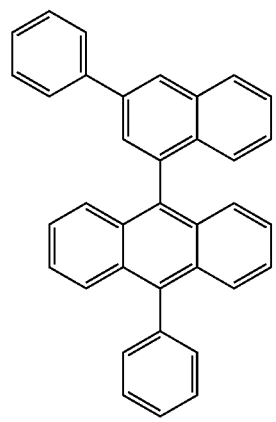
[Cpd. 2]
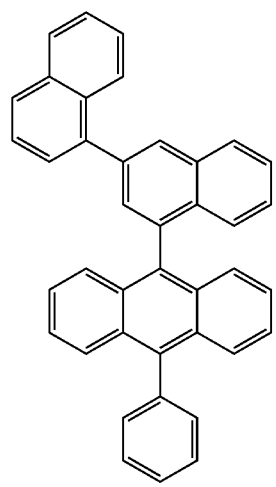
[Cpd. 3]
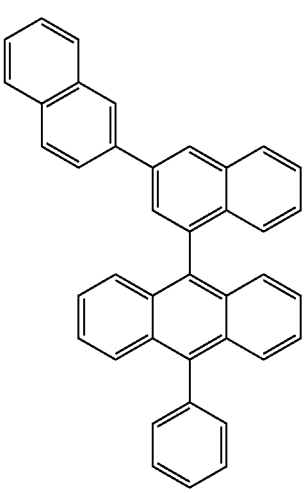
-continued
[Cpd. 4]
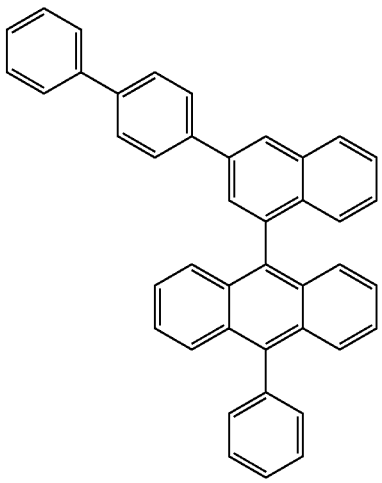
[Cpd. 5]
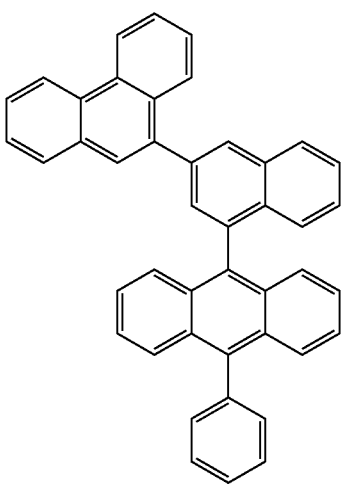
[Cpd. 6]
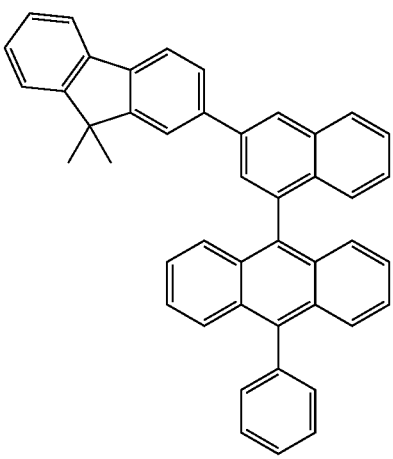

[Cpd. 7]
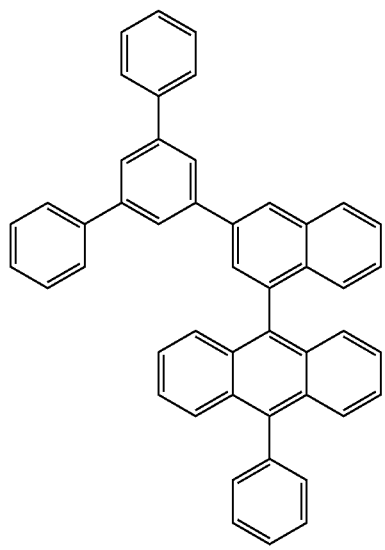
[Cpd. 10]
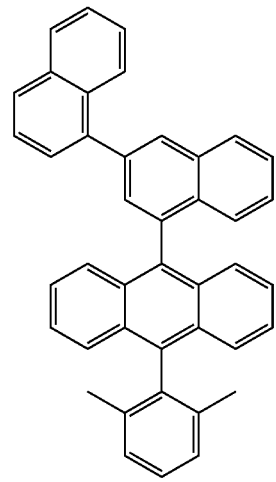
[Cpd. 8]
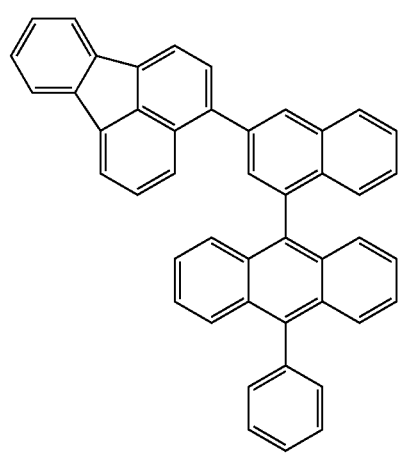
[Cpd. 11]
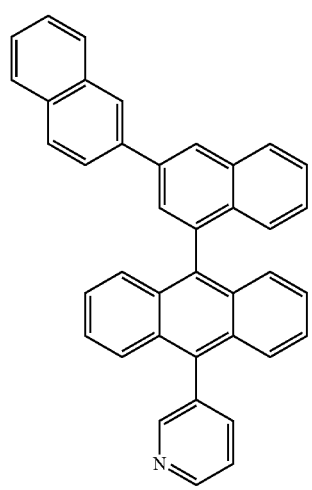
[Cpd. 9]
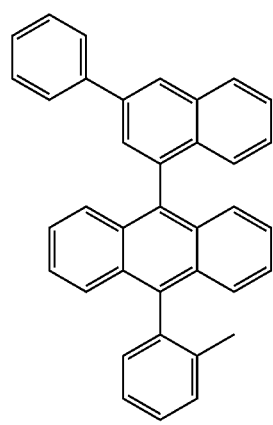
[Cpd. 12]
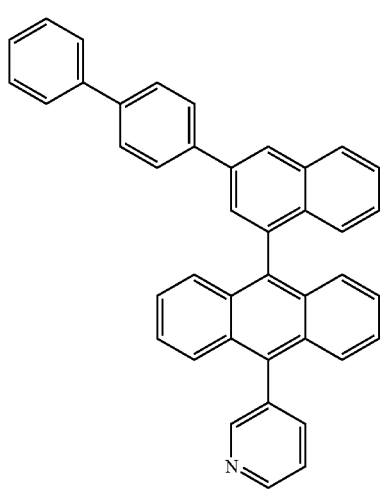

[Cpd. 13]
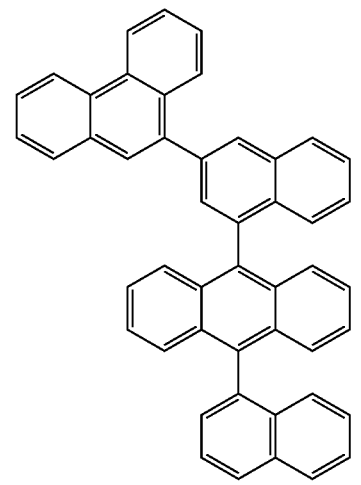
[Cpd. 14]
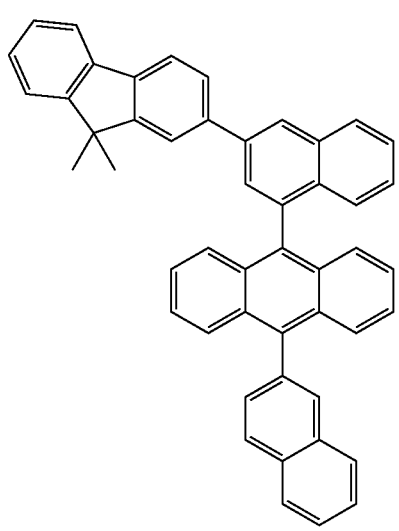
[Cpd. 15]
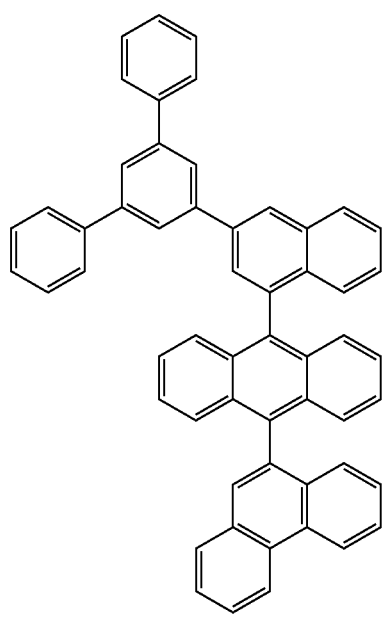
[Cpd. 16]
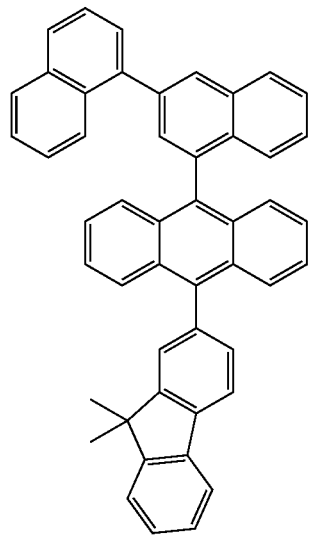
[Cpd. 17]
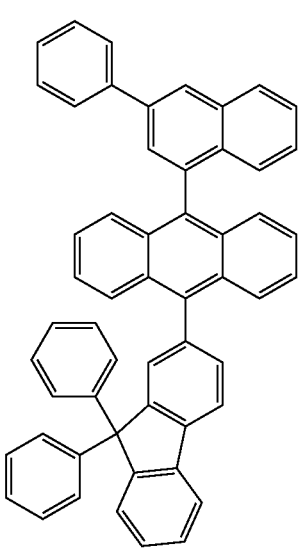
[Cpd. 18]
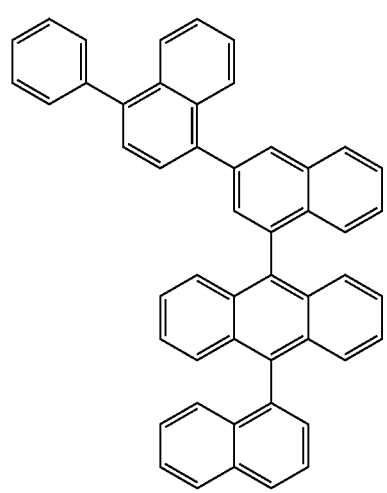

[Cpd. 19]
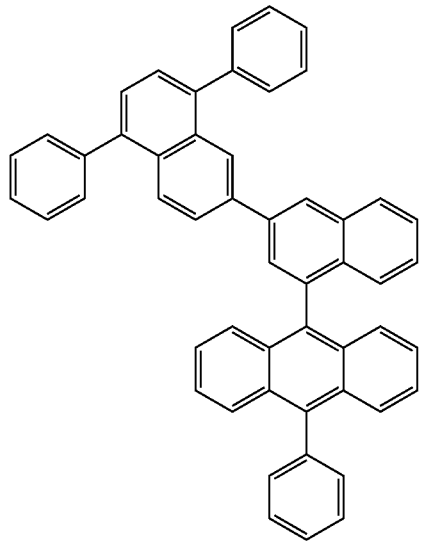
[Cpd. 20]
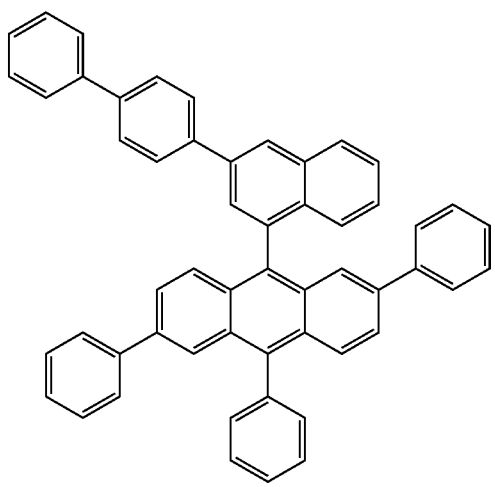
[Cpd. 21]
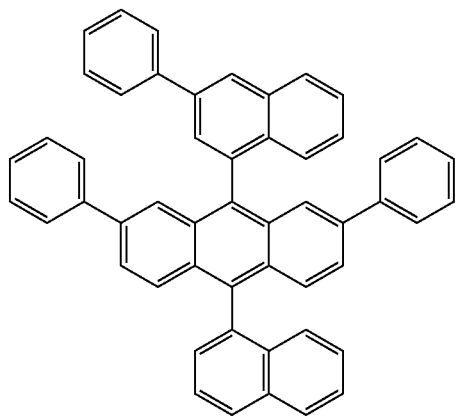
[Cpd. 22]
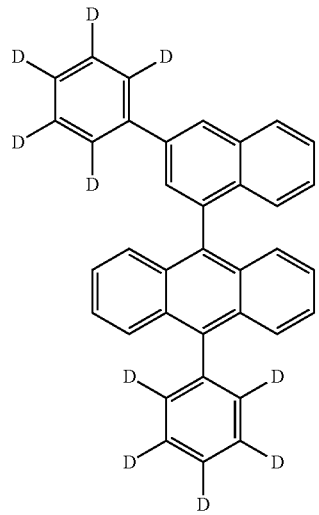
[Cpd. 23]
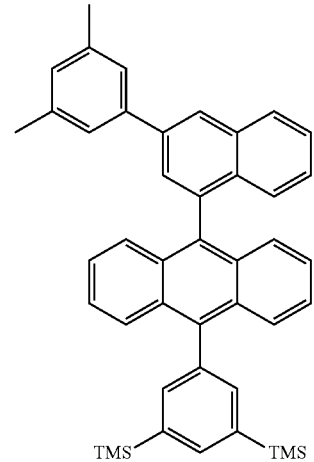
[Cpd. 24]
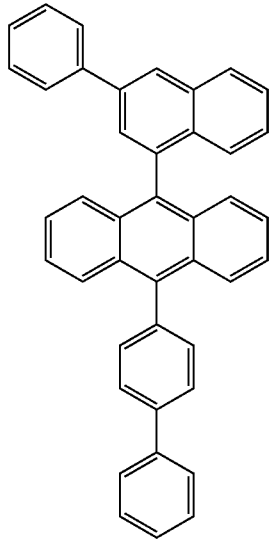

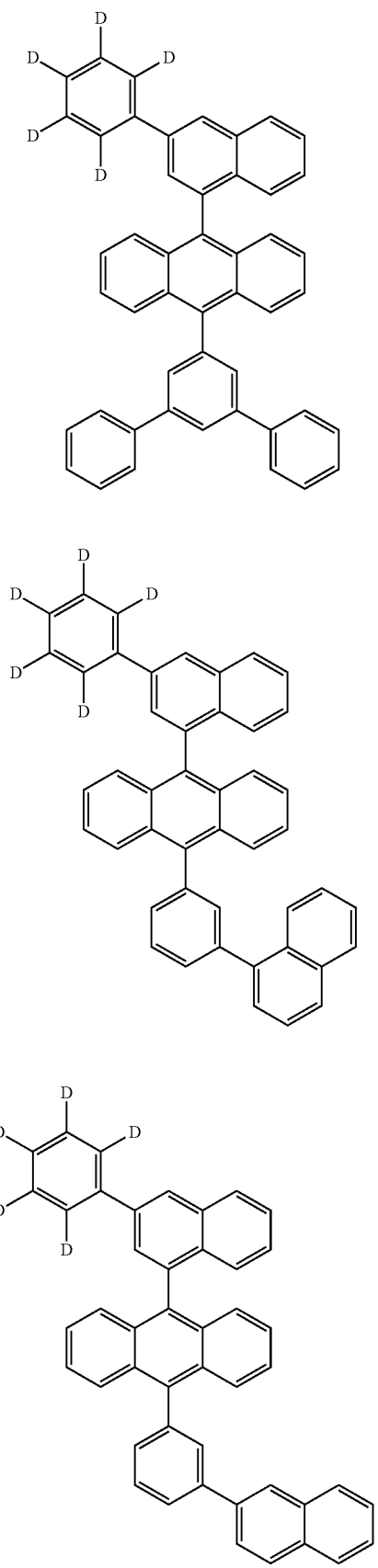
[Cpd. 25]
[Cpd. 26]
[Cpd. 27]
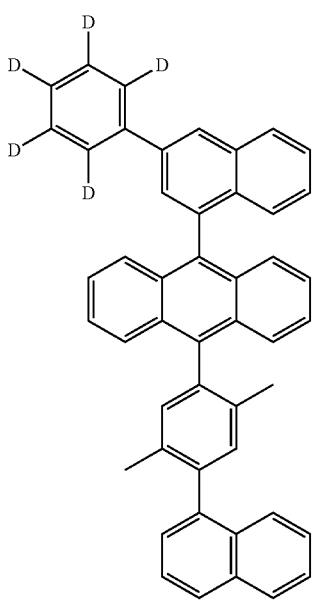
[Cpd. 28]
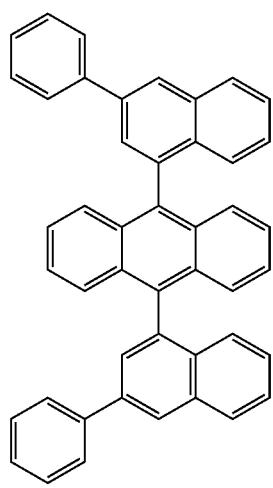
[Cpd. 29]
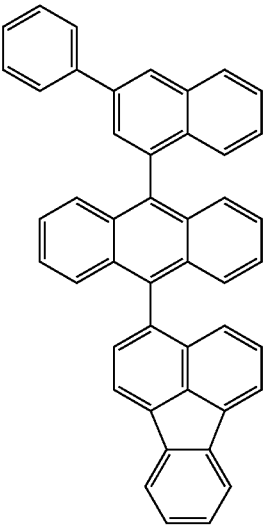
[Cpd. 30]

[Cpd. 31]
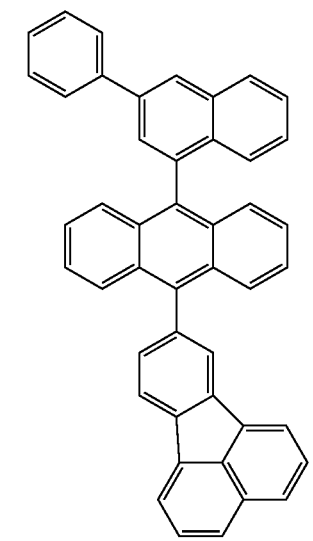
[Cpd. 32]
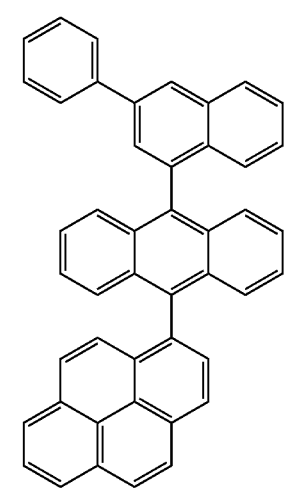
[Cpd. 33]
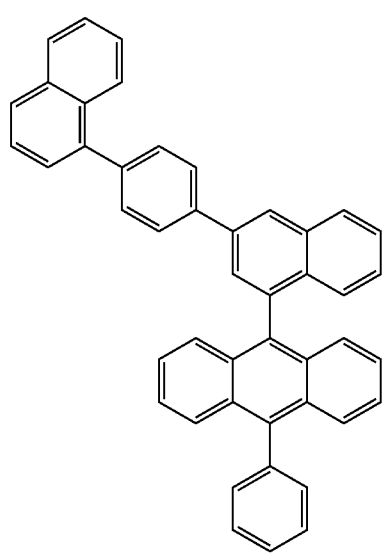
[Cpd. 34]
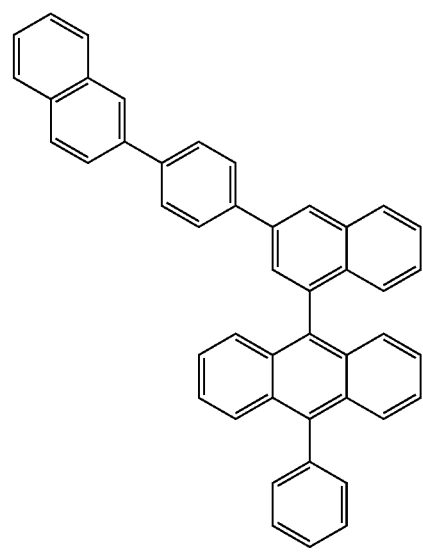
[Cpd. 35]
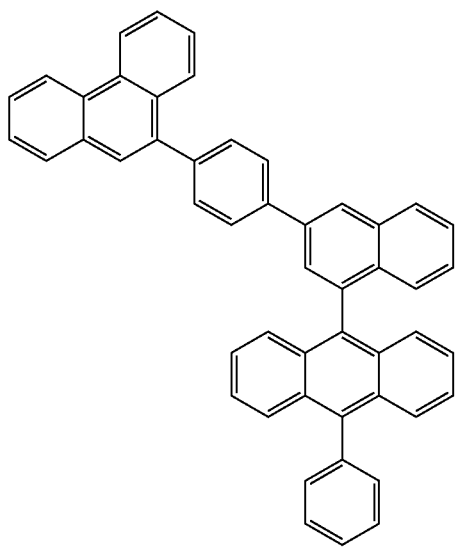
[Cpd. 36]
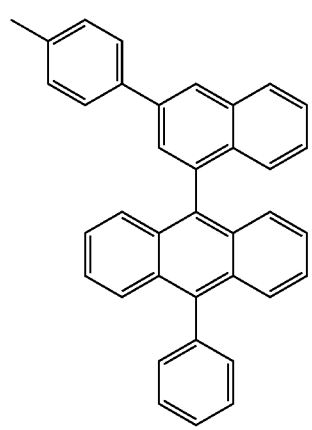

[Cpd. 37]
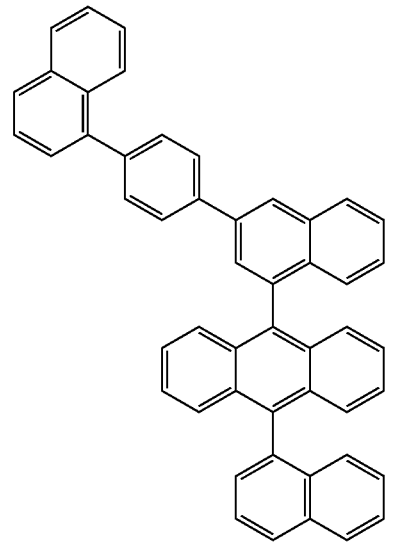
[Cpd. 38]
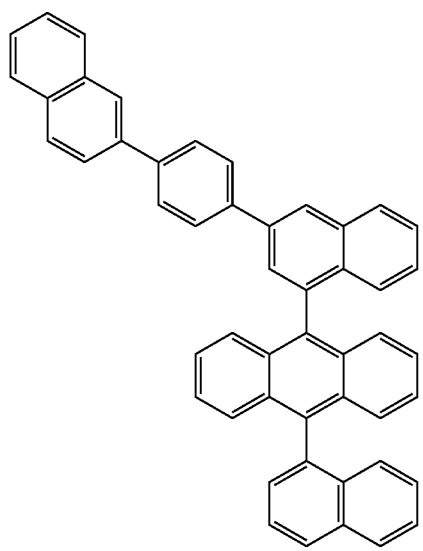
[Cpd. 39]
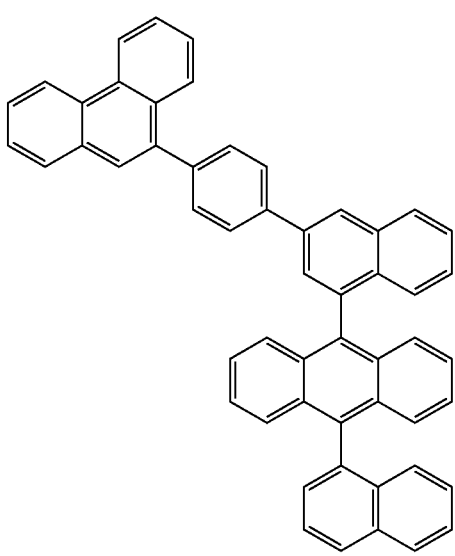
[Cpd. 40]
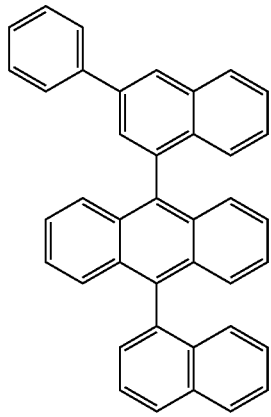
[Cpd. 41]
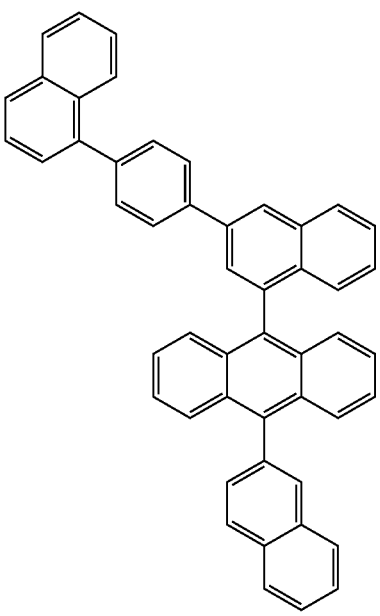
[Cpd. 42]
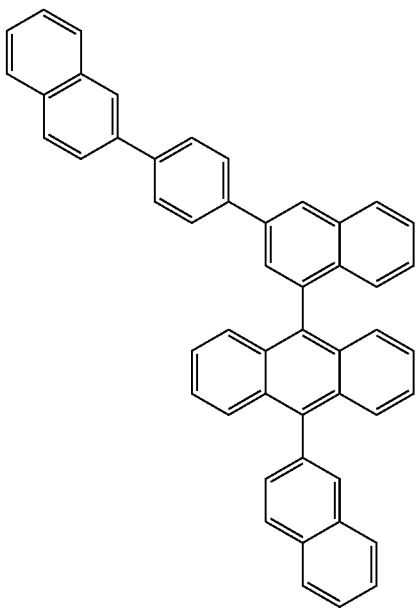

[Cpd. 43]
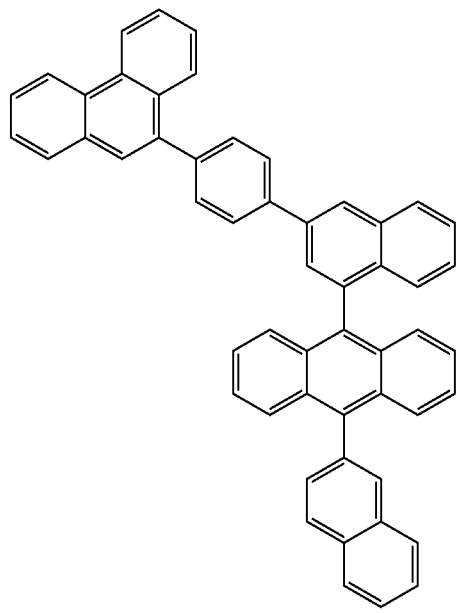
[Cpd. 44]
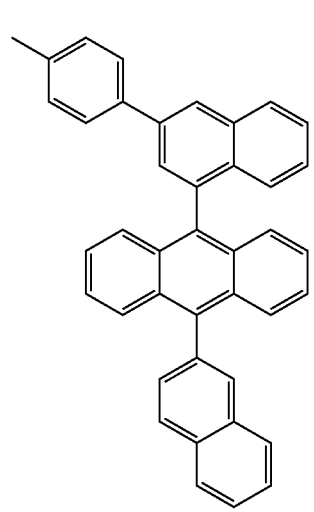
[Cpd. 45]
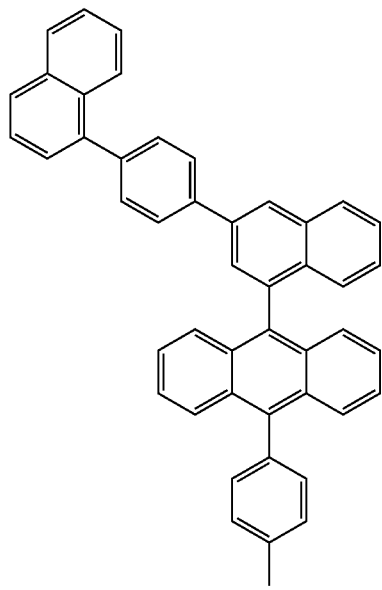
[Cpd. 46]
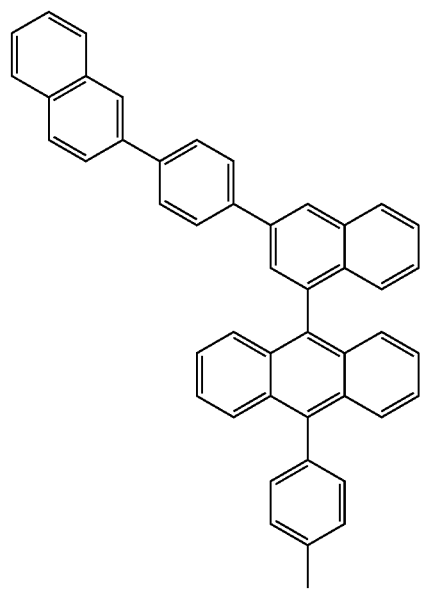

[Cpd. 47]
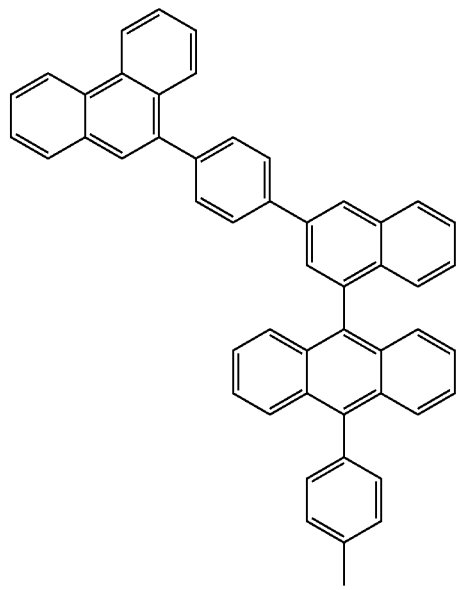
[Cpd. 50]
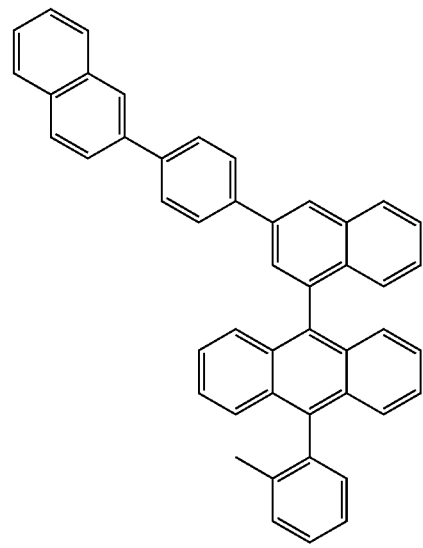
[Cpd. 48]
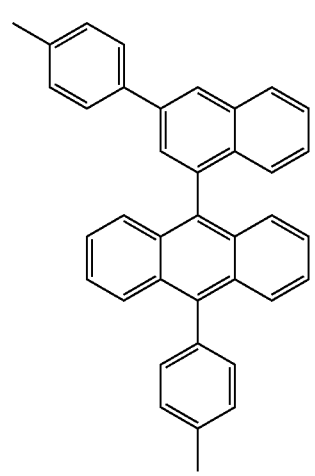
[Cpd. 51]
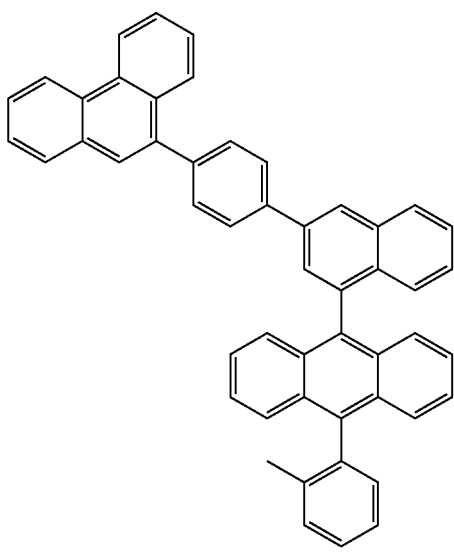
[Cpd. 49]
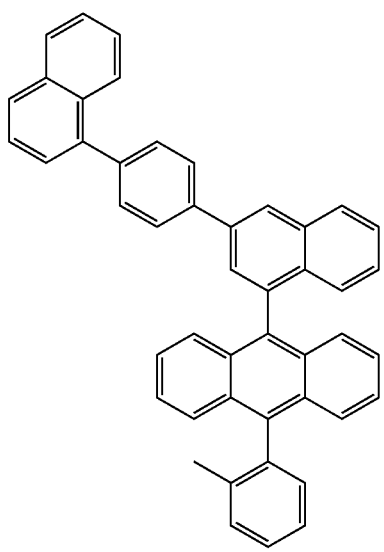
[Cpd. 52]
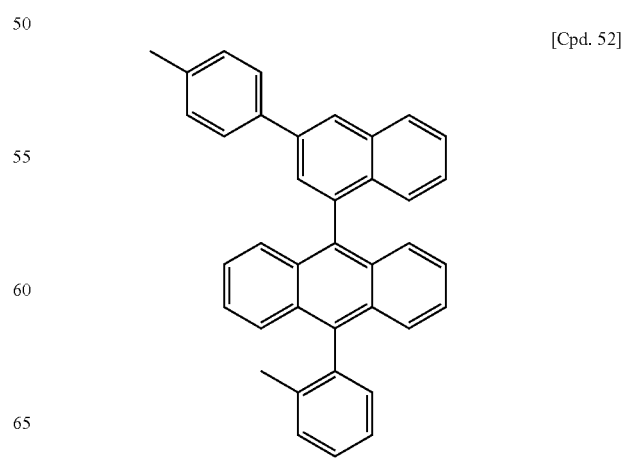

[Cpd. 53]
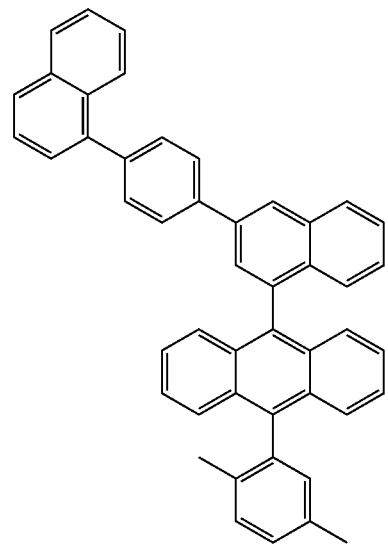
[Cpd. 54]
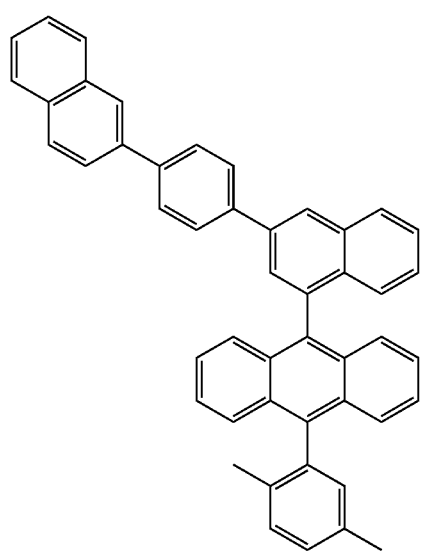
[Cpd. 55]
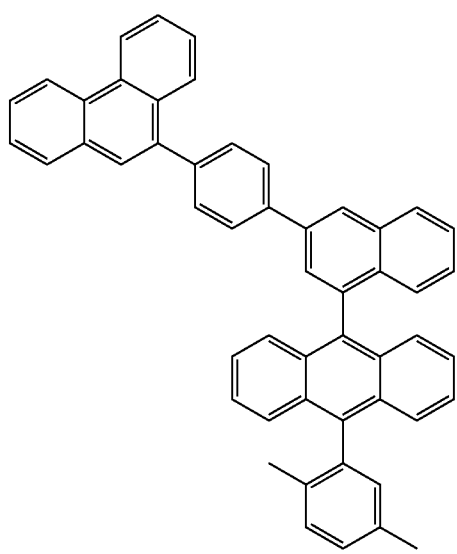
[Cpd. 56]
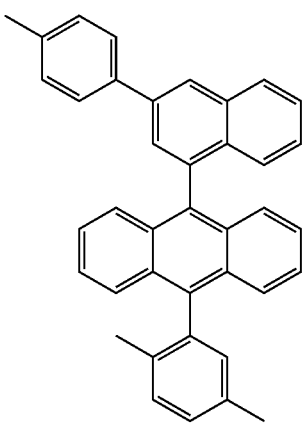
[Cpd. 57]
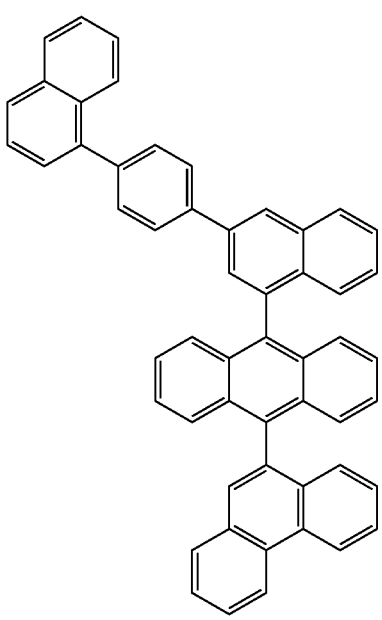
[Cpd. 58]
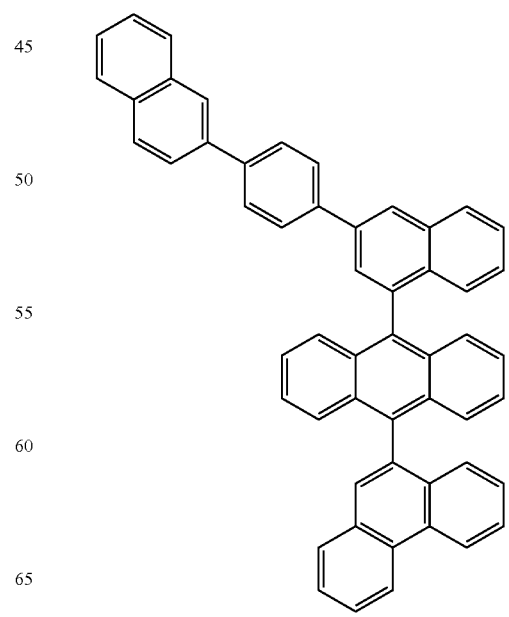

[Cpd. 59]
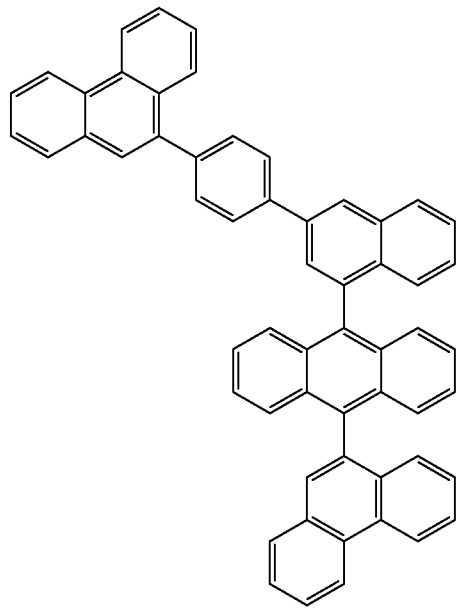
[Cpd. 60]
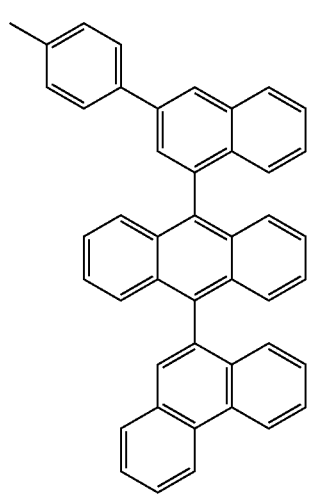
[Cpd. 61]
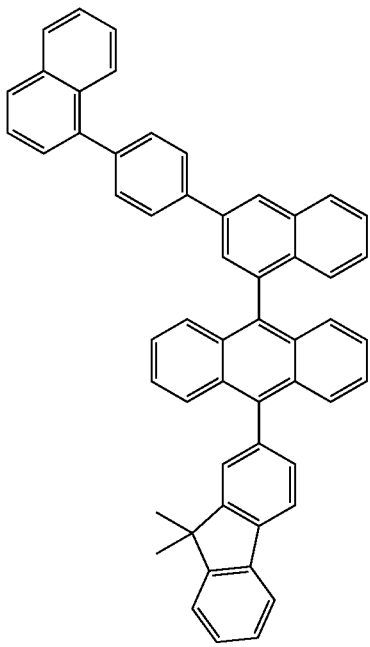
[Cpd. 62]

[Cpd. 63]
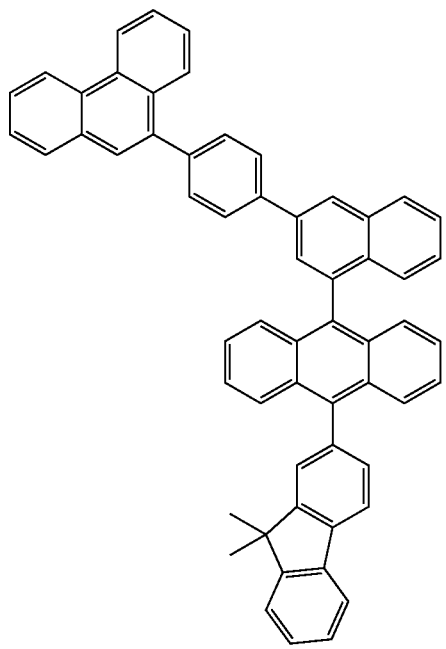
[Cpd. 64]
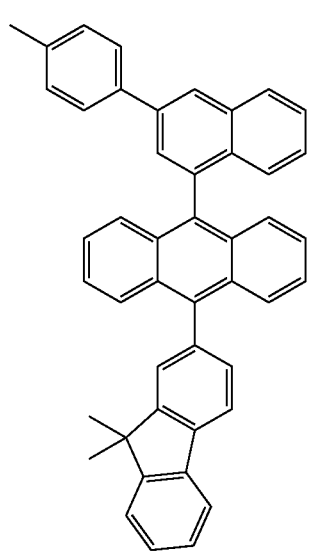
[Cpd. 65]
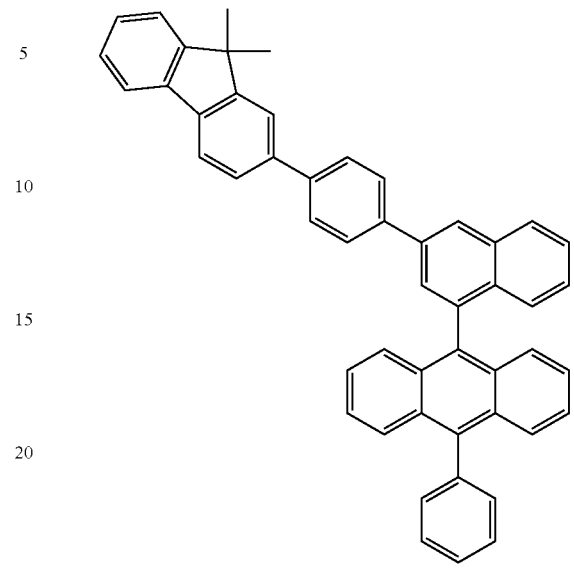
[Cpd. 66]
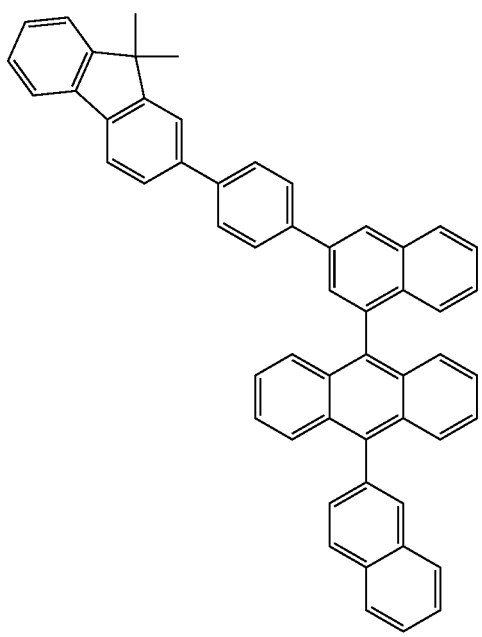

[Cpd. 67]
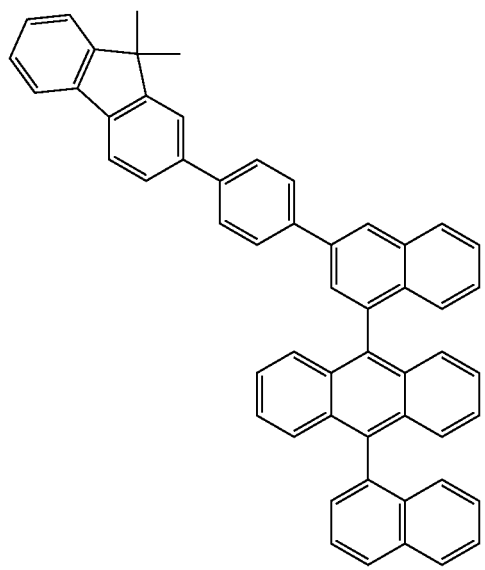
[Cpd. 68]
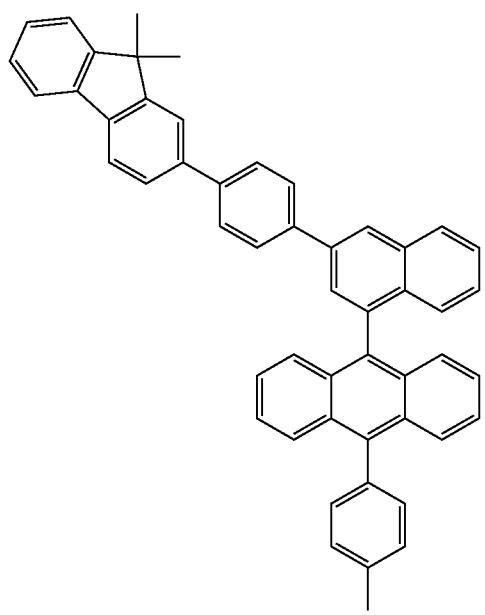
[Cpd. 69]
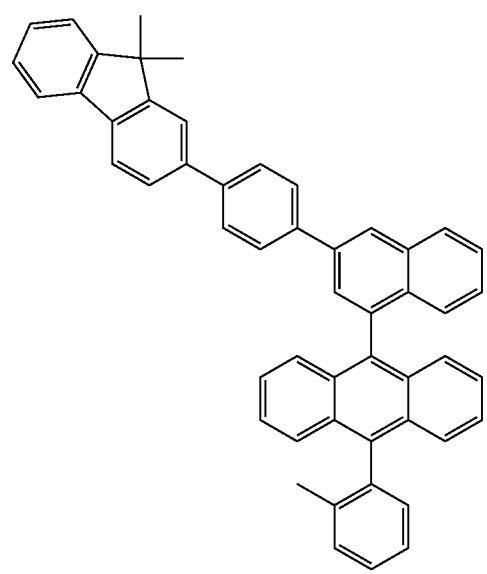
[Cpd. 70]
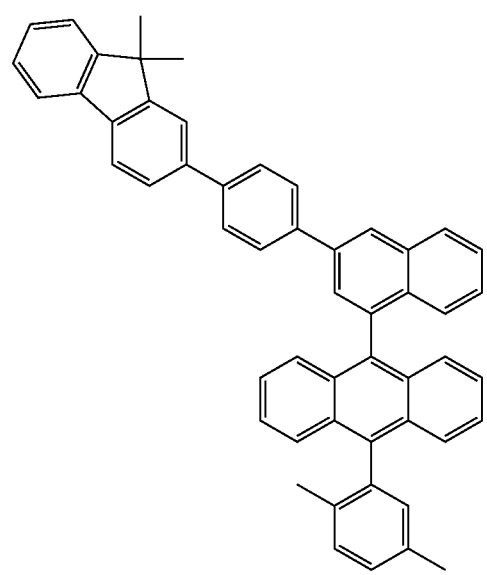

[Cpd. 71]
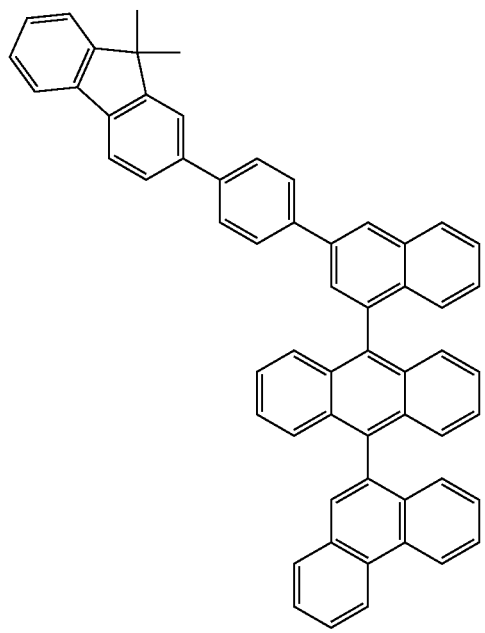
[Cpd. 73]
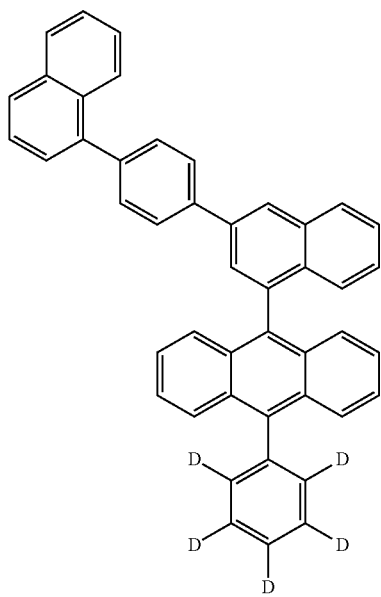
[Cpd. 72]
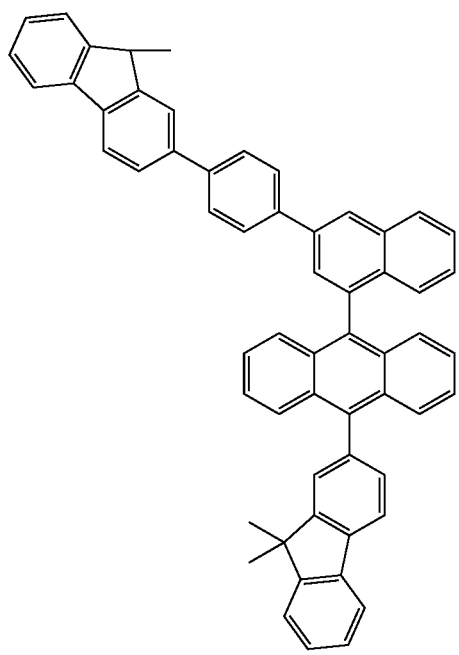
[Cpd. 74]
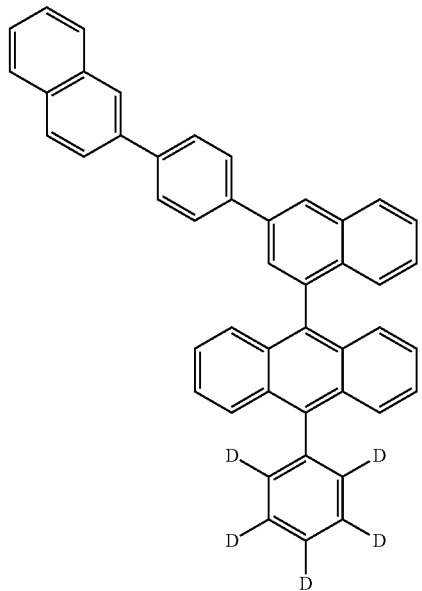

[Cpd. 75]
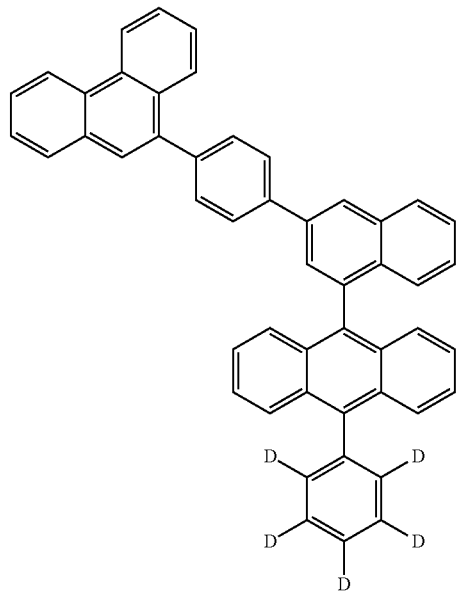
[Cpd. 76]
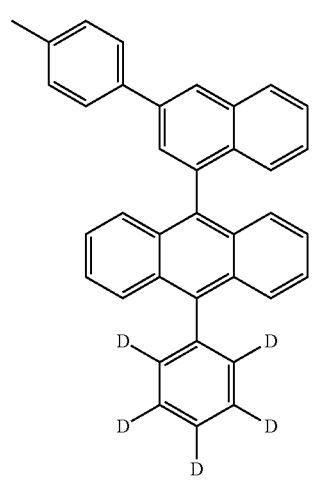
[Cpd. 77]
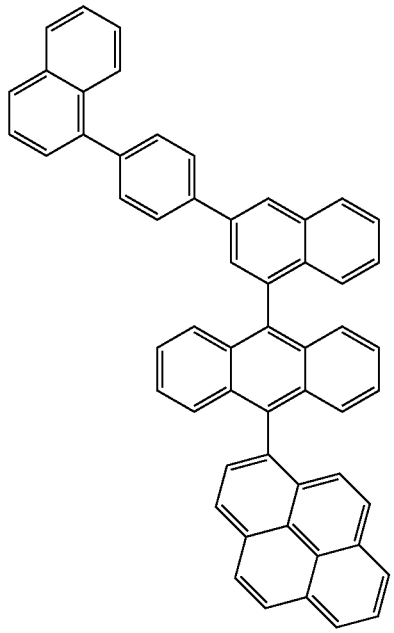
[Cpd. 78]
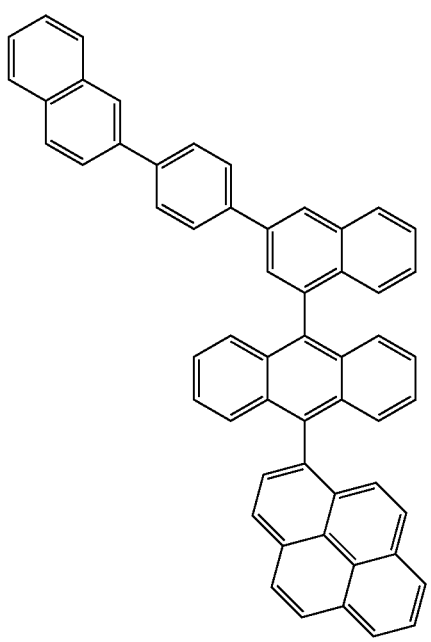

-continued

[Cpd. 79]

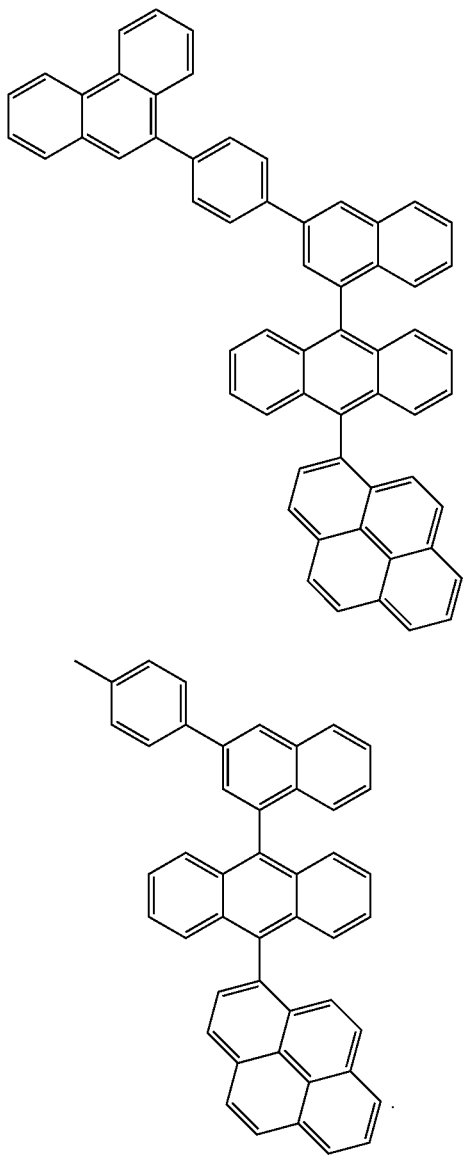

[Cpd. 80]

9. The organic light-emitting diode of claim 1, wherein the organic light-emitting diode comprises at least one of a hole injection layer, a hole transport layer, a functional layer capable of both hole injection and hole transport, an electron transport layer, and an electron injection layer, in addition to the light-emitting layer.

10. The organic light-emitting diode of claim 9, wherein at least one of the layers is formed using a deposition process or a solution process.

11. The organic light-emitting diode of claim 1, wherein organic light-emitting diode is used for a device selected from among a flat display device, a flexible display device, a monochrome or white flat illumination device, and a monochrome or white flexible illumination device.

12. The organic light-emitting diode of claim 1, wherein $R_1$ and $R_2$ together form the mono- or polycyclic aliphatic or aromatic ring in Chemical Formula B, and the mono- or polycyclic aliphatic or aromatic ring is a heterocyclic ring containing a heteroatom selected from the group consisting of N, O, P, Si, S, Ge, Se, and Te as a ring member.

13. The organic light-emitting diode of claim 1, the light-emitting layer is a mixture of the dopant and the host.

14. The organic light-emitting diode of claim 12, wherein the at least one of the amine compounds of Chemical Formula B in the light-emitting layer is represented by compound 91 or 92,

<91>

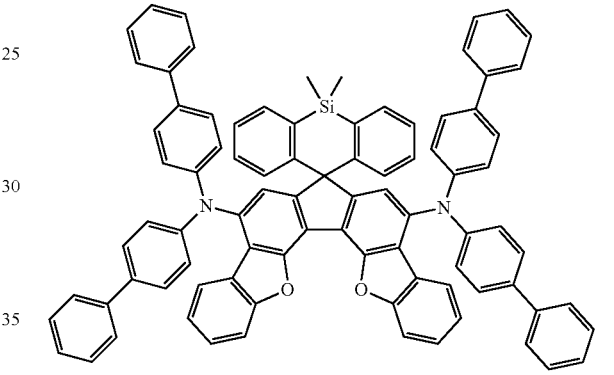

<92>

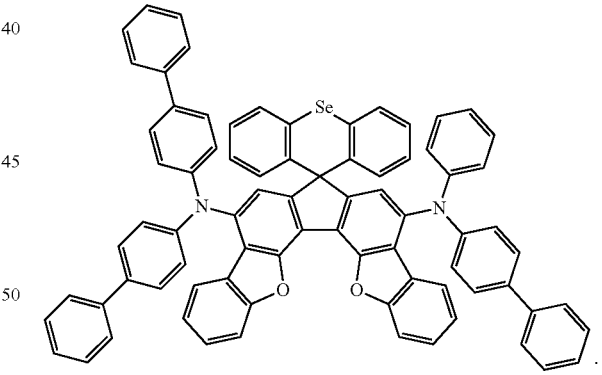

* * * * *